(12) United States Patent
Fleury et al.

(10) Patent No.: US 8,449,890 B2
(45) Date of Patent: *May 28, 2013

(54) NEPRILYSIN INHIBITORS

(75) Inventors: Melissa Fleury, San Francisco, CA (US); Roland Gendron, San Francisco, CA (US); Adam D. Hughes, Belmont, CA (US); Cameron Smith, Burlingame, CA (US)

(73) Assignee: Theravance, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/398,027

(22) Filed: Feb. 16, 2012

(65) Prior Publication Data

US 2012/0213807 A1 Aug. 23, 2012

Related U.S. Application Data

(60) Provisional application No. 61/443,828, filed on Feb. 17, 2011.

(51) Int. Cl.
- A61K 9/00 (2006.01)
- A61K 31/33 (2006.01)
- A61K 33/36 (2006.01)
- A61P 35/00 (2006.01)
- C07C 229/02 (2006.01)
- C07C 271/10 (2006.01)

(52) U.S. Cl.
USPC ........ 424/184.1; 514/274; 514/404; 540/137; 548/374.1; 560/27

(58) Field of Classification Search
USPC ................ 424/184.1; 514/274, 404; 540/137; 548/374.1; 560/27
See application file for complete search history.

(56) References Cited

U.S. PATENT DOCUMENTS

| | | | |
|---|---|---|---|
| 4,189,604 A | 2/1980 | Umezawa et al. | |
| 4,206,232 A | 6/1980 | Ondetti et al. | |
| 4,374,829 A | 2/1983 | Harris et al. | |
| 4,513,009 A | 4/1985 | Roques et al. | |
| 4,722,810 A | 2/1988 | Delaney et al. | |
| 4,906,615 A | 3/1990 | Berger | |
| 4,929,641 A | 5/1990 | Haslanger et al. | |
| 4,939,261 A | 7/1990 | Ksander | |
| 4,975,444 A | 12/1990 | Danilewicz et al. | |
| 5,021,430 A | 6/1991 | Ksander | |
| 5,030,654 A | 7/1991 | Barnish et al. | |
| 5,155,100 A | 10/1992 | Erion et al. | |
| 5,208,255 A | 5/1993 | Duhamel et al. | |
| 5,217,996 A | 6/1993 | Ksander | |
| 5,294,632 A | 3/1994 | Erion et al. | |
| 5,508,272 A | 4/1996 | Robl | |
| 5,599,951 A | 2/1997 | Plaquevent et al. | |
| 5,677,297 A | 10/1997 | Waldeck et al. | |
| 5,977,075 A | 11/1999 | Ksander et al. | |
| 6,602,866 B2 | 8/2003 | Flynn et al. | |
| 6,660,756 B2 | 12/2003 | Challenger et al. | |
| 2010/0113801 A1 | 5/2010 | Hook et al. | |
| 2010/0305131 A1 | 12/2010 | Coppola et al. | |
| 2010/0305145 A1 | 12/2010 | Coppola et al. | |
| 2011/0124695 A1 | 5/2011 | Iwaki et al. | |
| 2012/0122977 A1 | 5/2012 | Coppola et al. | |
| 2012/0157383 A1* | 6/2012 | Gendron et al. | 514/12.4 |
| 2012/0157386 A1* | 6/2012 | Smith et al. | 514/15.4 |
| 2012/0213806 A1* | 8/2012 | Fleury et al. | 424/184.1 |

FOREIGN PATENT DOCUMENTS

| | | | |
|---|---|---|---|
| WO | WO 2010/136474 | * 12/2010 | |
| WO | 2011/088797 A1 | 7/2011 | |

OTHER PUBLICATIONS

Ksander et al., "Dicarboxylic acid dipeptide neutral endopeptidase inhibitors", Journal of Medicinal Chemistry, 38 (10): 1689-1700 (1995).
Misawa et al., "Structure-based design of dipeptide derivatives for the human neutral endopeptidase", Bioorganic & Medicinal Chemistry, 19: 5935-5947 (2011).
U.S. Appl. No. 13/325,425, Gendron et al.
U.S. Appl. No. 13/325,453, Smith et al.
International Search Report for PCT/US2012/025369 dated Apr. 18, 2012.
U.S. Appl. No. 13/398,015, Fleury et al.
U.S. Appl. No. 13/474,987, Gendron et al.
U.S. Appl. No. 13/475,017, Fleury et al.
U.S. Appl. No. 13/475,076, Fleury et al.

* cited by examiner

*Primary Examiner* — Susannah Chung
(74) *Attorney, Agent, or Firm* — Jeffrey A. Hagenah; Shelley Eberle

(57) ABSTRACT

In one aspect, the invention relates to compounds having the formula:

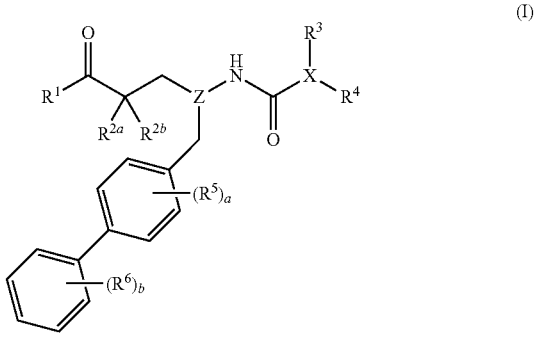

(I)

where $R^1$, $R^{2a}$, $R^{2b}$, $R^3$-$R^6$, a, b, Z, and X are as defined in the specification, or a pharmaceutically acceptable salt thereof. These compounds have neprilysin inhibition activity. In another aspect, the invention relates to pharmaceutical compositions comprising such compounds; methods of using such compounds; and processes and intermediates for preparing such compounds.

26 Claims, No Drawings

NEPRILYSIN INHIBITORS

CROSS-REFERENCE TO RELATED APPLICATIONS

This application claims the benefit of U.S. Provisional Application No. 61/443,828, filed on Feb. 17, 2011; the entire disclosure of which is incorporated herein by reference.

BACKGROUND OF THE INVENTION

1. Field of the Invention

The present invention relates to novel compounds having neprilysin-inhibition activity. The invention also relates to pharmaceutical compositions comprising such compounds, processes and intermediates for preparing such compounds and methods of using such compounds to treat diseases such as hypertension, heart failure, pulmonary hypertension, and renal disease.

2. State of the Art

Neprilysin (neutral endopeptidase, EC 3.4.24.11) (NEP), is an endothelial membrane bound $Zn^{2+}$metallopeptidase found in many organs and tissues, including the brain, kidneys, lungs, gastrointestinal tract, heart, and the peripheral vasculature. NEP degrades and inactivates a number of endogenous peptides, such as enkephalins, circulating bradykinin, angiotensin peptides, and natriuretic peptides, the latter of which have several effects including, for example, vasodilation and natriuresis/diuresis, as well as inhibition of cardiac hypertrophy and ventricular fibrosis. Thus, NEP plays an important role in blood pressure homeostasis and cardiovascular health.

NEP inhibitors, such as thiorphan, candoxatril, and candoxatrilat, have been studied as potential therapeutics. Compounds that inhibit both NEP and angiotensin-I converting enzyme (ACE) are also known, and include omapatrilat, gempatrilat, and sampatrilat. Referred to as vasopeptidase inhibitors, this latter class of compounds is described in Robl et al. (1999) *Exp. Opin. Ther. Patents* 9(12): 1665-1677.

SUMMARY OF THE INVENTION

The present invention provides novel compounds that have been found to possess neprilysin (NEP) enzyme inhibition activity. Accordingly, compounds of the invention are expected to be useful and advantageous as therapeutic agents for treating conditions such as hypertension and heart failure.

One aspect of the invention relates to a compound of formula I:

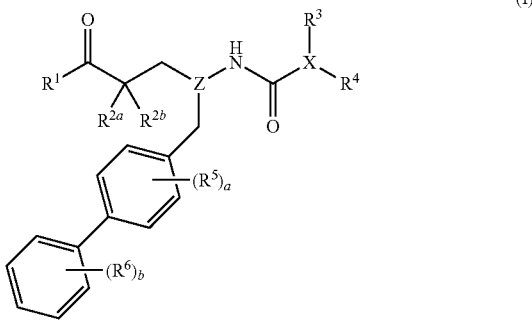

(I)

where:

$R^1$ is selected from $—OR^7$ and $—NR^8R^9$;

$R^{2a}$ is selected from $—OH$, $—OP(O)(OH)_2$, and $—OC(O)CH(R^{37})NH_2$, and $R^{2b}$ is $—CH_3$; or $R^{2a}$ and $R^{2b}$ are both $—CH_3$; or $R^{2a}$ and $R^{2b}$ are taken together to form $—CH_2—CH_2—$; or $R^{2a}$ is taken together with $R^7$ to form $—OCR^{18}R^{19}—$ or is taken together with $R^8$ to form $—OC(O)—$;

Z is selected from $—CH—$ and $—N—$;

X is a $—C_{1-9}$heteroaryl;

$R^3$ is absent or is selected from H; halo; $—C_{0-5}$alkylene-OH; $—NH_2$; $—C_{1-6}$alkyl; $—CF_3$; $—C_{3-7}$cycloalkyl; $—C_{0-2}$alkylene-O—$C_{1-6}$alkyl; $—C(O)R^{20}$; $—C_{0-1}$alkylene-COOR$^{21}$; $—C(O)NR^{22}R^{23}$; $—NHC(O)R^{24}$; $=O$; $—NO_2$; $—C(CH_3)=N(OH)$; phenyl optionally substituted with one or two groups independently selected from halo, $—OH$, $—CF_3$, $—OCH_3$, $—NHC(O)CH_3$, and phenyl; naphthalenyl; pyridinyl; pyrazinyl; pyrazolyl optionally substituted with methyl; thiophenyl optionally substituted with methyl or halo; furanyl; and $—CH_2$-morpholinyl; and $R^3$, when present, is attached to a carbon atom;

$R^4$ is absent or is selected from H; $—OH$; $—C_{1-6}$alkyl; $—C_{1-2}$alkylene-COOR$^{35}$; $—CH_2OC(O)CH(R^{36})NH_2$; $—OCH_2OC(O)CH(R^{36})NH_2$; $—OCH_2OC(O)CH_3$; $—CH_2OP(O)(OH)_2$; $—CH_2CH(OH)CH_2OH$; $—CH[CH(CH_3)_2]—NHC(O)O—C_{1-6}$alkyl; pyridinyl; and phenyl or benzyl optionally substituted with one or more groups selected from halo, $—COOR^{35}$, $—OCH_3$, $—OCF_3$, and $—SCF_3$; and $R^4$, when present, is attached to a carbon or nitrogen atom;

or $R^3$ and $R^4$ are taken together to form -phenylene-O—$(CH_2)_{1-3}$— or -phenylene-O—$CH_2$—CHOH—$CH_2$—;

a is 0 or 1; $R^5$ is selected from halo, $—CH_3$, $—CF_3$, and $—CN$;

b is 0 or an integer from 1 to 3; each $R^6$ is independently selected from halo, $—OH$, $—CH_3$, $—OCH_3$, and $—CF_3$;

$R^7$ is selected from H; $—C_{1-8}$alkyl; $—C_{1-3}$alkylene-$C_{6-10}$aryl; $—C_{1-3}$alkylene-$C_{1-9}$heteroaryl; $—C_{3-7}$cycloalkyl; $—[(CH_2)_2O]_{1-3}CH_3$; $—C_{1-6}$alkylene-OC(O)R$^{10}$; $—C_{1-6}$alkylene-NR$^{12}$R$^{13}$, $—C_{1-6}$alkylene-C(O)R$^{31}$, $—C_{0-6}$alkylenemorpholinyl; $—C_{1-6}$alkylene-SO$_2$—$C_{1-6}$alkyl;

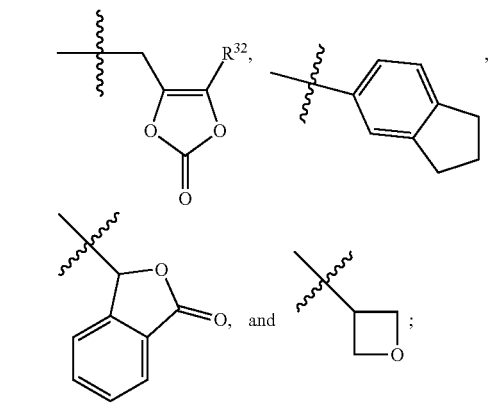

$R^{10}$ is selected from $—C_{1-6}$alkyl, $—O—C_{1-6}$alkyl, $—C_{3-7}$cycloalkyl, $—O—C_{3-7}$cycloalkyl, phenyl, $—O$-phenyl, $—NR^{12}R^{13}$, $—CH[CH(CH_3)_2]—NH_2$, $—CH[CH(CH_3)_2]—NHC(O)O—C_{1-6}$alkyl, and $—CH(NH_2)CH_2COOCH_3$; and $R^{12}$ and $R^{13}$ are independently selected from H, $—C_{1-6}$alkyl, and benzyl, or $R^{12}$ and $R^{13}$ are taken together as $—(CH_2)_{3-6}—$, $—C(O)—(CH_2)_3—$, or $—(CH_2)_2O(CH_2)_2—$;

$R^{31}$ is selected from —O—$C_{1-6}$alkyl, —O-benzyl, and —$NR^{12}R^{13}$; and $R^{32}$ is —$C_{1-6}$alkyl or —$C_{0-6}$alkylene-$C_{6-10}$aryl;

$R^8$ is selected from H, —OH, —OC(O)$R^{14}$, —$CH_2$COOH, —O-benzyl, pyridyl, and —OC(S)$NR^{15}R^{16}$; $R^{14}$ is selected from H, —$C_{1-6}$alkyl, —$C_{6-10}$aryl, —$OCH_2$—$C_{6-10}$aryl, —$CH_2$O—$C_{6-10}$aryl, and —$NR^{15}R^{16}$; and $R^{15}$ and $R^{16}$ are independently selected from H and —$C_{1-4}$alkyl;

$R^9$ is selected from H, —$C_{1-6}$alkyl, and —C(O)$R^{17}$; and $R^{17}$ is selected from H, —$C_{1-6}$alkyl, —$C_{3-7}$cycloalkyl, —$C_{6-10}$aryl, and —$C_{1-9}$heteroaryl;

$R^{18}$ and $R^{19}$ are independently selected from H, —$C_{1-6}$alkyl, and —O—$C_{3-7}$cycloalkyl, or $R^{18}$ and $R^{19}$ are taken together to form =O;

$R^{20}$ is selected from H and —$C_{1-6}$alkyl;

$R^{21}$ and $R^{35}$ are independently selected from H, —$C_{1-6}$alkyl, —$C_{1-3}$alkylene-$C_{6-10}$aryl, —$C_{1-3}$alkylene-$C_{1-9}$heteroaryl, —$C_{3-7}$cycloalkyl, —[($CH_2$)$_2$O]$_{1-3}CH_3$, —$C_{1-6}$alkylene-OC(O)$R^{25}$, —$C_{1-6}$alkylene-$NR^{27}R^{28}$, $C_{1-6}$alkylene-C(O)$R^{33}$, —$C_{0-6}$alkylenemorpholinyl, —$C_{1-6}$alkylene-$SO_2$—$C_{1-6}$alkyl,

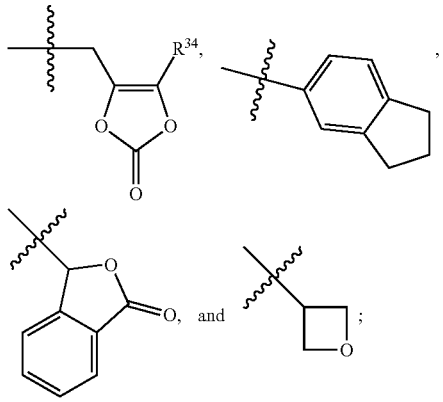

$R^{25}$ is selected from —$C_{1-6}$alkyl, —O—$C_{1-6}$alkyl, —$C_{3-7}$cycloalkyl, —O—$C_{3-7}$cycloalkyl, phenyl, —O-phenyl, —$NR^{27}R^{28}$, —CH[CH($CH_3$)$_2$]—$NH_2$, —CH[CH($CH_3$)$_2$]—NHC(O)O—$C_{1-6}$alkyl, and —CH($NH_2$)$CH_2$COO$CH_3$; and $R^{27}$ and $R^{28}$ are independently selected from H, —$C_{1-6}$alkyl, and benzyl, or $R^{27}$ and $R^{28}$ are taken together as —($CH_2$)$_{3-6}$—, —C(O)—($CH_2$)$_3$—, or —($CH_2$)$_2$O($CH_2$)$_2$—; $R^{33}$ is selected from —O—$C_{1-6}$alkyl, —O-benzyl, and —$NR^{27}R^{28}$; and $R^{34}$ is $C_{1-6}$alkyl or —$C_{0-6}$alkylene-$C_{6-10}$aryl;

$R^{22}$ and $R^{23}$ are independently selected from H, —$C_{1-6}$alkyl, —$CH_2$COOH, —($CH_2$)$_2$OH; —($CH_2$)$_2OCH_3$, —($CH_2$)$_2SO_2NH_2$, —($CH_2$)$_2$N($CH_3$)$_2$, —$C_{0-1}$alkylene-$C_{3-7}$cycloalkyl, and —($CH_2$)$_2$-imidazolyl; or $R^{22}$ and $R^{23}$ are taken together to form a saturated or partially unsaturated —$C_{3-5}$heterocycle optionally substituted with halo, —OH, —COOH, or —$CONH_2$; and optionally containing an oxygen atom in the ring;

$R^{24}$ is selected from —$C_{1-6}$alkyl; —$C_{0-1}$alkylene-O—$C_{1-6}$alkyl; phenyl optionally substituted with halo or —$OCH_3$; and —$C_{1-9}$heteroaryl; and $R^{36}$ is selected from H, —CH($CH_3$)$_2$, phenyl, and benzyl; and $R^{37}$ is selected from H, —CH($CH_3$)$_2$, phenyl, and benzyl;

where each alkyl group in $R^1$, $R^3$, and $R^4$ is optionally substituted with 1 to 8 fluoro atoms; and;

where the methylene linker on the biphenyl is optionally substituted with one or two —$C_{1-6}$alkyl groups or cyclopropyl;

or a pharmaceutically acceptable salt thereof.

Another aspect of the invention relates to pharmaceutical compositions comprising a pharmaceutically acceptable carrier and a compound of the invention. Such compositions may optionally contain other therapeutic agents. Accordingly, in yet another aspect of the invention, a pharmaceutical composition comprises a compound of the invention as the first therapeutic agent, one or more secondary therapeutic agent, and a pharmaceutically acceptable carrier. Another aspect of the invention relates to a combination of active agents, comprising a compound of the invention and a second therapeutic agent. The compound of the invention can be formulated together or separately from the additional agent(s). When formulated separately, a pharmaceutically acceptable carrier may be included with the additional agent(s). Thus, yet another aspect of the invention relates to a combination of pharmaceutical compositions, the combination comprising: a first pharmaceutical composition comprising a compound of the invention and a first pharmaceutically acceptable carrier; and a second pharmaceutical composition comprising a second therapeutic agent and a second pharmaceutically acceptable carrier. In another aspect, the invention relates to a kit containing such pharmaceutical compositions, for example where the first and second pharmaceutical compositions are separate pharmaceutical compositions.

Compounds of the invention possess NEP enzyme inhibition activity, and are therefore expected to be useful as therapeutic agents for treating patients suffering from a disease or disorder that is treated by inhibiting the NEP enzyme or by increasing the levels of its peptide substrates. Thus, one aspect of the invention relates to a method of treating patients suffering from a disease or disorder that is treated by inhibiting the NEP enzyme, comprising administering to a patient a therapeutically effective amount of a compound of the invention. Another aspect of the invention relates to a method of treating hypertension, heart failure, or renal disease, comprising administering to a patient a therapeutically effective amount of a compound of the invention. Still another aspect of the invention relates to a method for inhibiting a NEP enzyme in a mammal comprising administering to the mammal, a NEP enzyme-inhibiting amount of a compound of the invention.

Since compounds of the invention possess NEP inhibition activity, they are also useful as research tools. Accordingly, one aspect of the invention relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay. Still another aspect of the invention relates to a method of studying a biological system or sample comprising a NEP enzyme, the method comprising: (a) contacting the biological system or sample with a compound of the invention; and (b) determining the effects caused by the compound on the biological system or sample.

Yet another aspect of the invention relates to processes and intermediates useful for preparing compounds of the invention. Accordingly, another aspect of the invention relates to a process of preparing compounds of formula I, comprising the step of coupling a compound of formula 1 with a compound of formula 2:

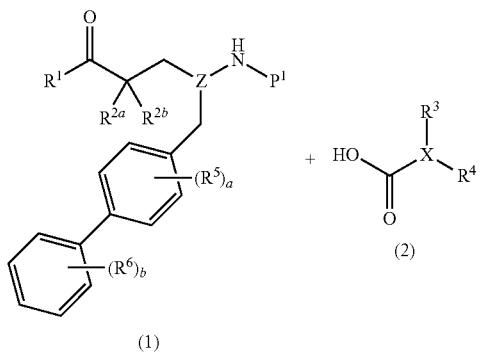

to produce a compound of formula I; where $P^1$ is H or an amino-protecting group selected from t-butoxycarbonyl, trityl, benzyloxycarbonyl, 9-fluorenylmethoxycarbonyl, formyl, trimethylsilyl, and t-butyldimethylsilyl; and where the process further comprises deprotecting the compound of formula 1 when $P^1$ is an amino protecting group; and where $R^1$, $R^{2a}$, $R^{2b}$, $R^3$-$R^6$, a, b, Z, and X are as defined for formula I. Another aspect of the invention relates to a process of preparing a pharmaceutically acceptable salt of a compound of formula I, comprising contacting a compound of formula I in free acid or base form with a pharmaceutically acceptable base or acid. In other aspects, the invention relates to products prepared by any of the processes described herein, as well as novel intermediates used in such process. In one aspect of the invention novel intermediates have formula 1, 9, 10, 11, 12, or a salt thereof, as defined herein.

Yet another aspect of the invention relates to the use of a compound of formula I or a pharmaceutically acceptable salt thereof, for the manufacture of a medicament, especially for the manufacture of a medicament useful for treating hypertension, heart failure, or renal disease. Another aspect of the invention relates to use of a compound of the invention for inhibiting a NEP enzyme in a mammal. Still another aspect of the invention relates to the use of a compound of the invention as a research tool. Other aspects and embodiments of the invention are disclosed herein.

DETAILED DESCRIPTION OF THE INVENTION

Definitions

When describing the compounds, compositions, methods and processes of the invention, the following terms have the following meanings unless otherwise indicated. Additionally, as used herein, the singular forms "a," "an," and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

The term "alkyl" means a monovalent saturated hydrocarbon group which may be linear or branched. Unless otherwise defined, such alkyl groups typically contain from 1 to 10 carbon atoms and include, for example, —$C_{1-4}$alkyl, —$C_{1-5}$alkyl, —$C_{2-5}$alkyl, —$C_{1-6}$alkyl, —$C_{1-8}$alkyl, and —$C_{1-10}$alkyl. Representative alkyl groups include, by way of example, methyl, ethyl, n-propyl, isopropyl, n-butyl, s-butyl, isobutyl, t-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term as subscript. For example, the term "—$C_{1-6}$alkyl" means an alkyl group having from 1 to 6 carbon atoms, and the term "—$C_{3-7}$cycloalkyl" means a cycloalkyl group having from 3 to 7 carbon atoms, respectively, where the carbon atoms are in any acceptable configuration.

The term "alkylene" means a divalent saturated hydrocarbon group that may be linear or branched. Unless otherwise defined, such alkylene groups typically contain from 0 to 10 carbon atoms and include, for example, —$C_{0-1}$alkylene-, —$C_{0-6}$alkylene-, —$C_{1-3}$alkylene-, and —$C_{1-6}$alkylene-. Representative alkylene groups include, by way of example, methylene, ethane-1,2-diyl ("ethylene"), propane-1,2-diyl, propane-1,3-diyl, butane-1,4-diyl, pentane-1,5-diyl and the like. It is understood that when the alkylene term include zero carbons such as —$C_{0-1}$alkylene-, such terms are intended to include the absence of carbon atoms, that is, the alkylene group is not present except for a covalent bond attaching the groups separated by the alkylene term.

The term "aryl" means a monovalent aromatic hydrocarbon having a single ring (i.e., phenyl) or one or more fused rings. Fused ring systems include those that are fully unsaturated (e.g., naphthalene) as well as those that are partially unsaturated (e.g., 1,2,3,4-tetrahydronaphthalene). Unless otherwise defined, such aryl groups typically contain from 6 to 10 carbon ring atoms and include, for example, —$C_{6-10}$aryl. Representative aryl groups include, by way of example, phenyl and naphthalene-1-yl, naphthalene-2-yl, and the like.

The term "cycloalkyl" means a monovalent saturated carbocyclic hydrocarbon group. Unless otherwise defined, such cycloalkyl groups typically contain from 3 to 10 carbon atoms and include, for example, —$C_{3-5}$cycloalkyl, —$C_{3-6}$cycloalkyl and —$C_{3-7}$cycloalkyl. Representative cycloalkyl groups include, by way of example, cyclopropyl, cyclobutyl, cyclopentyl, cyclohexyl and the like.

The term "halo" means fluoro, chloro, bromo and iodo.

The term "heterocycle" is intended to include monovalent unsaturated (aromatic) heterocycles having a single ring or two fused rings as well as monovalent saturated and partially unsaturated groups having a single ring or multiple condensed rings. The heterocycle ring can contain from 3 to 15 total ring atoms, of which 1 to 14 are ring carbon atoms, and 1 to 4 are ring heteroatoms selected from nitrogen, oxygen or sulfur. Typically, however, the heterocycle ring contains from 3 to 10 total ring atoms, of which 1 to 9 are ring carbon atoms, and 1 to 4 are ring heteroatoms. The point of attachment is at any available carbon or nitrogen ring atom. Exemplary heterocycles include, for example, —$C_{1-7}$heterocycle, —$C_{3-5}$heterocycle, —$C_{2-6}$heterocycle, —$C_{3-12}$heterocycle, —$C_{5-9}$heterocycle, —$C_{1-9}$heterocycle, —$C_{1-11}$heterocycle, and —$C_{1-14}$heterocycle.

Monovalent unsaturated heterocycles are also commonly referred to as "heteroaryl" groups. Unless otherwise defined, heteroaryl groups typically contain from 5 to 10 total ring atoms, of which 1 to 9 are ring carbon atoms, and 1 to 4 are ring heteroatoms, and include, for example, —$C_{1-9}$heteroaryl and —$C_{5-9}$heteroaryl. Representative heteroaryl groups include, by way of example, pyrrole (e.g., 3-pyrrolyl and 2H-pyrrol-3-yl), imidazole (e.g., 2-imidazolyl), furan (e.g., 2-furyl and 3-furyl), thiophene (e.g., 2-thienyl), triazole (e.g., 1,2,3-triazolyl and 1,2,4-triazolyl), pyrazole (e.g., 1H-pyrazol-3-yl), oxazole (e.g., 2-oxazolyl), isoxazole (e.g., 3-isoxazolyl), thiazole (e.g., 2-thiazolyl and 4-thiazolyl), and isothiazole (e.g., 3-isothiazolyl), pyridine (e.g., 2-pyridyl, 3-pyridyl, and 4-pyridyl), pyridylimidazole, pyridyltriazole, pyrazine, pyridazine (e.g., 3-pyridazinyl), pyrimidine (e.g., 2-pyrimidinyl), tetrazole, triazine (e.g., 1,3,5-triazinyl), indolyle (e.g., 1H-indol-2-yl, 1H-indol-4-yl and 1H-indol-5-yl), benzofuran (e.g., benzofuran-5-yl), benzothiophene (e.g., benzo[b]thien-2-yl and benzo[b]thien-5-yl), benzimidazole, benzoxazole, benzothiazole, benzotriazole, quinoline (e.g., 2-quinolyl), isoquinoline, quinazolinequinoxaline and the like.

Monovalent saturated heterocycles typically contain from 3 to 10 total ring atoms, of which 2 to 9 are ring carbon atoms, and 1 to 4 are ring heteroatoms, and include, for example —$C_{3-5}$heterocycle. Representative monovalent saturated heterocycles include, by way of example, monovalent species of pyrrolidine, imidazolidine, pyrazolidine, piperidine, 1,4-dioxane, morpholine, thiomorpholine, piperazine, 3-pyrroline and the like. In some instances, moieties may be described as being taken together to form a saturated —$C_{3-5}$heterocycle optionally containing an oxygen atom in the ring. Such groups include:

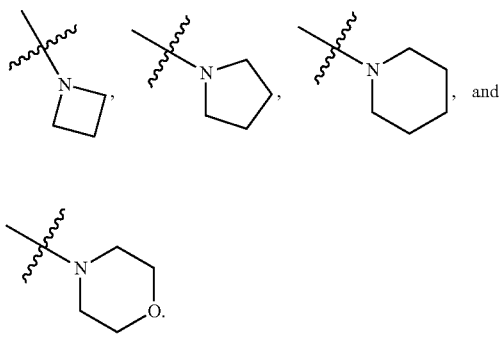

Monovalent partially unsaturated heterocycles typically contain from 3 to 10 total ring atoms, of which 2 to 11 are ring carbon atoms, and 1 to 3 are ring heteroatoms, and include, for example —$C_{3-5}$heterocycle and —$C_{2-12}$heterocycle. Representative monovalent partially unsaturated heterocycles include, by way of example, pyran, benzopyran, benzodioxole (e.g., benzo[1,3]dioxol-5-yl), tetrahydropyridazine, 2,5-dihydro-1H-pyrrole, dihydroimidazole, dihydrotriazole, dihydrooxazole, dihydroisoxazole, dihydrothiazole, dihydroisothiazole, dihydrooxadiazole, dihydrothiadiazole, tetrahydropyridazine, hexahydropyrroloquinoxaline, and dihydrooxadiazabenzo[e]azulene. In some instances, moieties may be described as being taken together to form a partially unsaturated —$C_{3-5}$heterocycle. Such groups include:

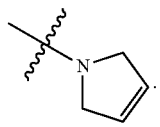

The term "optionally substituted" means that group in question may be unsubstituted or it may be substituted one or several times, such as 1 to 3 times, or 1 to 5 times, or 1 to 8 times. For example, a phenyl group that is "optionally substituted" with halo atoms, may be unsubstituted, or it may contain 1, 2, 3, 4, or 5 halo atoms; and an alkyl group that is "optionally substituted" with fluoro atoms may be unsubstituted, or it may contain 1, 2, 3, 4, 5, 6, 7, or 8 fluoro atoms. Similarly, a group that is "optionally substituted" with one or two —$C_{1-6}$alkyl groups, may be unsubstituted, or it may contain one or two —$C_{1-6}$alkyl groups.

As used herein, the phrase "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug administration.

The term "pharmaceutically acceptable salt" means a salt prepared from a base or an acid which is acceptable for administration to a patient, such as a mammal (for example, salts having acceptable mammalian safety for a given dosage regime). However, it is understood that the salts covered by the invention are not required to be pharmaceutically acceptable salts, such as salts of intermediate compounds that are not intended for administration to a patient. Pharmaceutically acceptable salts can be derived from pharmaceutically acceptable inorganic or organic bases and from pharmaceutically acceptable inorganic or organic acids. In addition, when a compound of formula I contains both a basic moiety, such as an amine, pyridine or imidazole, and an acidic moiety such as a carboxylic acid or tetrazole, zwitterions may be formed and are included within the term "salt" as used herein. Salts derived from pharmaceutically acceptable inorganic bases include ammonium, calcium, copper, ferric, ferrous, lithium, magnesium, manganic, manganous, potassium, sodium, and zinc salts, and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids include salts of aliphatic hydroxyl acids (for example, citric, gluconic, glycolic, lactic, lactobionic, malic, and tartaric acids), aliphatic monocarboxylic acids (for example, acetic, butyric, formic, propionic and trifluoroacetic acids), amino acids (for example, aspartic and glutamic acids), aromatic carboxylic acids (for example, benzoic, p-chlorobenzoic, diphenylacetic, gentisic, hippuric, and triphenylacetic acids), aromatic hydroxyl acids (for example, o-hydroxybenzoic, p-hydroxybenzoic, 1-hydroxynaphthalene-2-carboxylic and 3-hydroxynaphthalene-2-carboxylic acids), ascorbic, dicarboxylic acids (for example, fumaric, maleic, oxalic and succinic acids), glucoronic, mandelic, mucic, nicotinic, orotic, pamoic, pantothenic, sulfonic acids (for example, benzenesulfonic, camphosulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

As used herein, the term "prodrug" is intended to mean an inactive (or significantly less active) precursor of a drug that is converted into its active form in the body under physiological conditions, for example, by normal metabolic processes. Such compounds may not possess pharmacological activity at NEP, but may be administered orally or parenterally and thereafter metabolized in the body to form compounds that are pharmacologically active at NEP. Exemplary prodrugs include esters such as $C_{1-6}$alkylesters and aryl-$C_{1-6}$alkylesters. In one embodiment, the active compound has a free carboxyl and the prodrug is an ester derivative thereof, i.e., the prodrug is an ester such as —C(O)OCH$_2$CH$_3$. Such ester prodrugs are then converted by solvolysis or under physiological conditions to be the free carboxyl compound. The term is also intended to include certain protected derivatives of compounds of formula I that may be made prior to a final deprotection stage. Thus, all protected derivatives and prodrugs of compounds formula I are included within the scope of the invention.

The term "therapeutically effective amount" means an amount sufficient to effect treatment when administered to a patient in need thereof, that is, the amount of drug needed to obtain the desired therapeutic effect. For example, a therapeutically effective amount for treating hypertension is an amount of compound needed to, for example, reduce, suppress, eliminate, or prevent the symptoms of hypertension, or to treat the underlying cause of hypertension. In one embodiment, a therapeutically effective amount is that amount of drug needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising a NEP enzyme, an "effective amount" may be the amount needed to inhibit the enzyme.

The term "treating" or "treatment" as used herein means the treating or treatment of a disease or medical condition (such as hypertension) in a patient, such as a mammal (particularly a human) that includes one or more of the following: (a) preventing the disease or medical condition from occurring, i.e., preventing the reoccurrence of the disease or medical condition or prophylactic treatment of a patient that is pre-disposed to the disease or medical condition; (b) ameliorating the disease or medical condition, i.e., eliminating or causing regression of the disease or medical condition in a patient; (c) suppressing the disease or medical condition, i.e., slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition, as well as test subjects in which compounds of the invention are being evaluated or being used in an assay, for example an animal model.

All other terms used herein are intended to have their ordinary meaning as understood by those of ordinary skill in the art to which they pertain.

In one aspect, the invention relates to compounds of formula I:

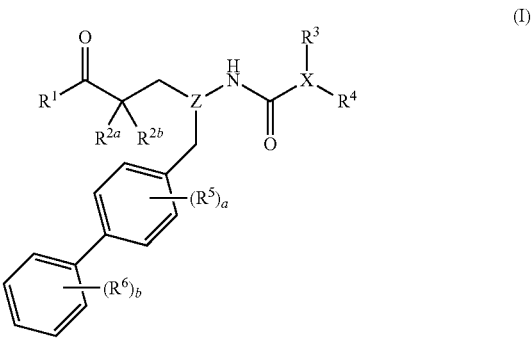

or a pharmaceutically acceptable salt thereof.

As used herein, the term "compound of the invention" includes all compounds encompassed by formula I such as the species embodied in formulas Ia to If, Ia-1 to Ia-4, Ib-1, Ib-2, Ic-1, Ic-2, Id-1, and Id-2, as well as the compounds encompassed by formulas II-VIII, and species thereof. Similarly, reference to compound of a given formula is intended to include all species; for example the term "compound of formula III" is intended to include the species IIIa and IIIb, and so forth. In addition, the compounds of the invention may also contain several basic or acidic groups (for example, amino or carboxyl groups) and therefore, such compounds can exist as a free base, free acid, or in various salt forms. All such salt forms are included within the scope of the invention. Furthermore, the compounds of the invention may also exist as prodrugs. Accordingly, those skilled in the art will recognize that reference to a compound herein, for example, reference to a "compound of the invention" or a "compound of formula I" includes a compound of formula I as well as pharmaceutically acceptable salts and prodrugs of that compound unless otherwise indicated. Further, the term "or a pharmaceutically acceptable salt and/or prodrug thereof" is intended to include all permutations of salts and prodrugs, such as a pharmaceutically acceptable salt of a prodrug. Furthermore, solvates of compounds of formula I are included within the scope of this invention.

The compounds of formula I may contain one or more chiral centers and therefore, these compounds may be prepared and used in various stereoisomeric forms. Accordingly, the invention also relates to racemic mixtures, pure stereoisomers (e.g., enantiomers and diastereoisomers), stereoisomer-enriched mixtures, and the like unless otherwise indicated. When a chemical structure is depicted herein without any stereochemistry, it is understood that all possible stereoisomers are encompassed by such structure. Thus, for example, the terms "compound of formula I," "compounds of formula II," and so forth, are intended to include all possible stereoisomers of the compound. Similarly, when a particular stereoisomer is shown or named herein, it will be understood by those skilled in the art that minor amounts of other stereoisomers may be present in the compositions of the invention unless otherwise indicated, provided that the utility of the composition as a whole is not eliminated by the presence of such other isomers. Individual stereoisomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds of the invention are included within the scope of the invention unless otherwise specified. For example, if X is depicted as ($R^4$ being hydrogen):

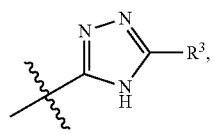

it is understood that the compound may also exist in a tautomeric form such as:

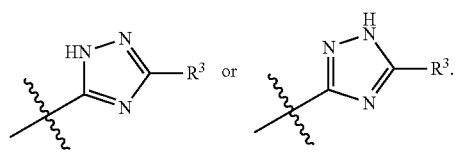

More specifically, compounds of formula I where $R^{2a}$ is —OH or —OP(O)(OH)$_2$, and $R^{2b}$ is —CH$_3$ can contain at least two chiral centers when the "Z" moiety is —CH—; compounds of formula I where $R^{2a}$ and $R^{2b}$ are both —CH$_3$ or where $R^{2a}$ and $R^{2b}$ are taken together to form —CH$_2$—CH$_2$— can contain at least one chiral center when the "Z" moiety is —CH—; and compounds of formula I where $R^{2a}$ is —OH or —OP(O)(OH)$_2$, and $R^{2b}$ is —CH$_3$ can contain at least one chiral center when the "Z" moiety is —N—. These chiral centers are indicated by the symbols * and ** in the following formulas 1a, 1b, 1c, and 1d (illustrated with $R^{2a}$ as —OH):

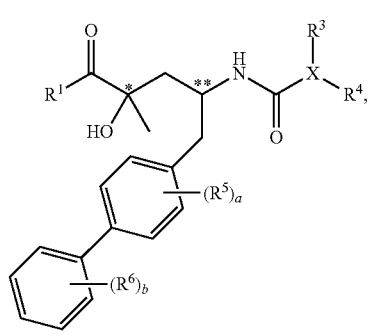

(Ia)

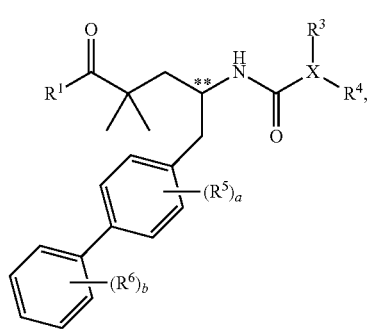

(Ib)

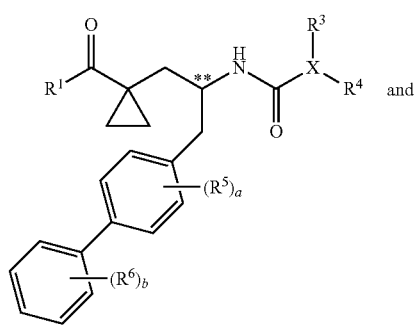

(Ic) and

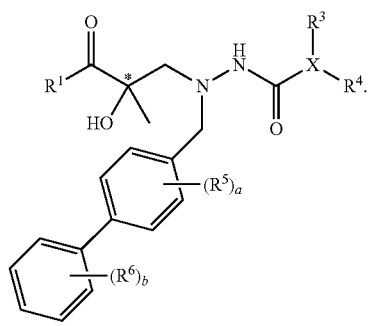

(Id)

In one stereoisomer of the compound of formula Ia, both carbon atoms identified by the * and ** symbols have the (R) configuration. This embodiment of the invention is shown in formula Ia-1:

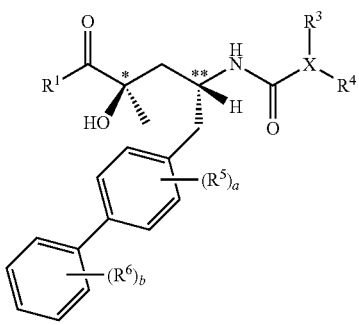

(Ia-1)

In this embodiment, compounds have the (R,R) configuration at the * and ** carbon atoms or are enriched in a stereoisomeric form having the (R,R) configuration at these carbon atoms. In another stereoisomer of the compound of formula Ia, both carbon atoms identified by the * and ** symbols have the (S) configuration. This embodiment of the invention is shown in formula Ia-2:

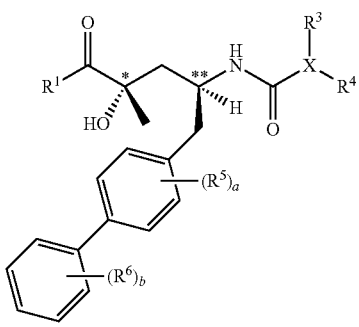

(Ia-2)

In this embodiment, compounds have the (S,S) configuration at the * and ** carbon atoms or are enriched in a stereoisomeric form having the (S,S) configuration at these carbon atoms. In yet another stereoisomer of the compound of formula Ia, the carbon atom identified by the symbol * has the (S) configuration and the carbon atom identified by the symbol ** has the (R) configuration. This embodiment of the invention is shown in formula Ia-3:

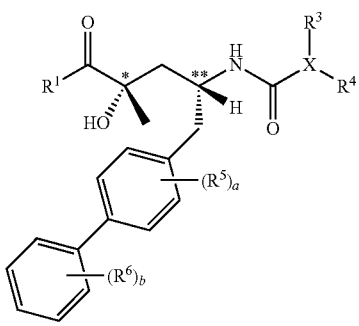

(Ia-3)

In this embodiment, compounds have the (S,R) configuration at the * and ** carbon atoms or are enriched in a stereoisomeric form having the (S,R) configuration at these carbon atoms. In still another stereoisomer of the compound of formula Ia, the carbon atom identified by the symbol * has the (R) configuration and the carbon atom identified by the symbol ** has the (S) configuration. This embodiment of the invention is shown in formula Ia-4:

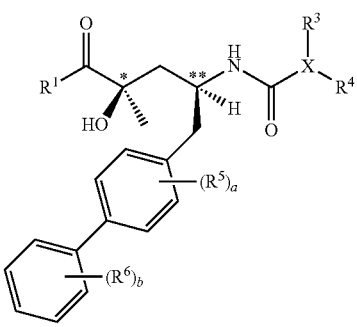

(Ia-4)

In this embodiment, compounds have the (R,S) configuration at the * and ** carbon atoms or are enriched in a stereoisomeric form having the (R,S) configuration at these carbon atoms.

In one stereoisomer of the compounds of formula Ib and Ic, the carbon atom identified by the ** symbol has the (R) configuration. These embodiments of the invention are shown in formulas Ib-1 and Ic-1, respectively:

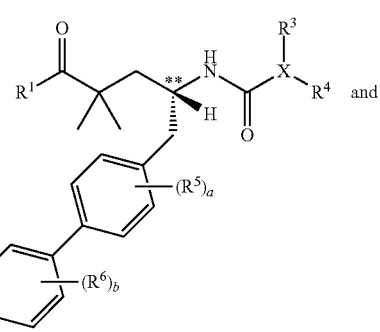

(Ib-1) and

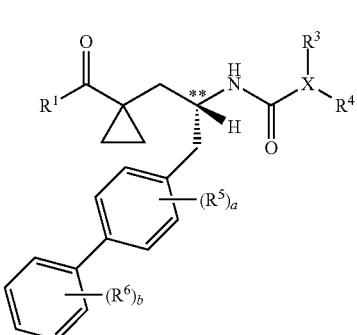

(Ic-1)

In these embodiments, compounds have the (R) configuration at the  carbon atom or are enriched in a stereoisomeric form having the (R) configuration at this carbon atom. In another stereoisomer of the compounds of formula Ib and Ic, the carbon atom identified by the  symbol has the (S) configuration. These embodiments of the invention are shown in formulas Ib-2 and Ic-2, respectively:

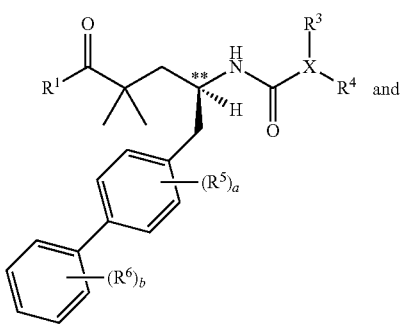

(Ib-2)

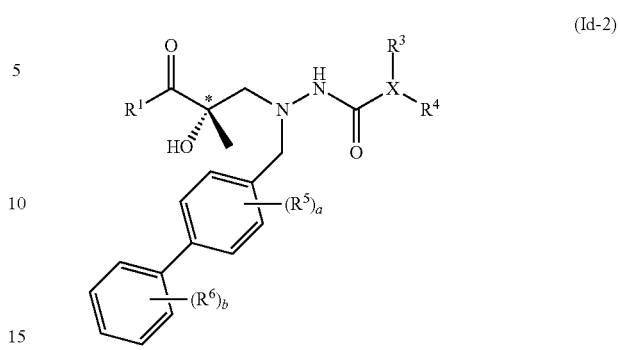

(Id-2)

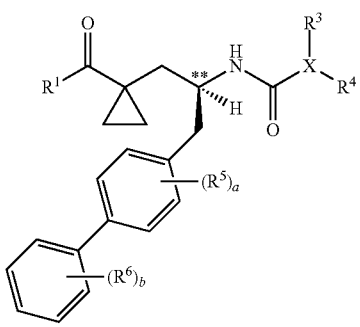

(Ic-2)

In these embodiments, compounds have the (S) configuration at the ** carbon atom or are enriched in a stereoisomeric form having the (S) configuration at this carbon atom.

In one stereoisomer of the compound of formula Id, the carbon atom identified by the * symbol has the (R) configuration. This embodiment of the invention is shown in formula Id-1:

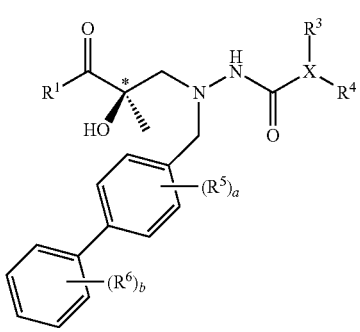

(Id-1)

In this embodiment, compounds have the (R) configuration at the * carbon atom or are enriched in a stereoisomeric form having the (R) configuration at this carbon atom. In another stereoisomer of the compound of formula Id, the carbon atom identified by the * symbol has the (S) configuration. This embodiment of the invention is shown in formula Id-2:

In this embodiment, compounds have the (S) configuration at the * carbon atom or are enriched in a stereoisomeric form having the (S) configuration at this carbon atom.

In some embodiments, in order to optimize the therapeutic activity of the compounds of the invention, e.g., to treat hypertension, it may be desirable that the carbon atoms identified by the * and ** symbols have a particular configuration or are enriched in a stereoisomeric form having such configuration. Thus, in certain aspects, this invention relates to each individual enantiomer or to an enantiomer-enriched mixture of enantiomers comprising predominately one enantiomer or the other enantiomer. In other embodiments, the compounds of the invention are present as racemic mixtures of enantiomers.

The compounds of the invention, as well as those compounds used in their synthesis, may also include isotopically-labeled compounds, that is, where one or more atoms have been enriched with atoms having an atomic mass different from the atomic mass predominately found in nature. Examples of isotopes that may be incorporated into the compounds of formula I, for example, include, but are not limited to, $^2$H, $^3$H, $^{13}$C, $^{14}$C, $^{15}$N, $^{18}$O, $^{17}$O, $^{35}$S, $^{36}$Cl, and $^{18}$F. Of particular interest are compounds of formula I enriched in tritium or carbon-14 which can be used, for example, in tissue distribution studies; compounds of formula I enriched in deuterium especially at a site of metabolism resulting, for example, in compounds having greater metabolic stability; and compounds of formula I enriched in a positron emitting isotope, such as $^{11}$C, $^{18}$F, $^{15}$O and $^{13}$N, which can be used, for example, in Positron Emission Topography (PET) studies.

The nomenclature used herein to name the compounds of the invention is illustrated in the Examples herein. This nomenclature has been derived using the commercially available AutoNom software (MDL, San Leandro, Calif.).

Representative Embodiments

The following substituents and values are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

In one aspect, this invention relates to compounds of formula I:

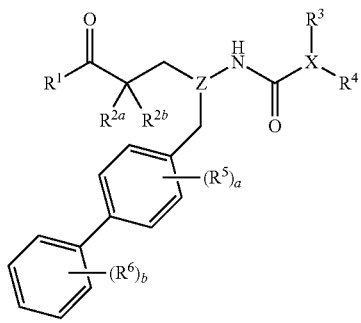

R$^1$ is selected from —OR$^7$ and —NR$^8$R$^9$. The R$^7$ moiety is selected from:

H;

—C$_{1-8}$alkyl, e.g., —CH$_3$, —CH$_2$CH$_3$, —(CH$_2$)$_2$CH$_3$, —CH(CH$_3$)$_2$, —CH$_2$CH(CH$_3$)$_2$, —(CH$_2$)$_3$CH$_3$, —(CH$_2$)$_4$CH$_3$, —(CH$_2$)$_2$CH(CH$_3$)$_2$, —(CH$_2$)$_5$CH$_3$, and —(CH$_2$)$_6$CH$_3$;

—C$_{1-3}$alkylene-C$_{6-10}$aryl, e.g., benzyl;

—C$_{1-3}$alkylene-C$_{1-9}$heteroaryl, e.g., —CH$_2$-pyridinyl and —(CH$_2$)$_2$-pyridinyl;

—C$_{3-7}$cycloalkyl, e.g., cyclopentyl;

—[(CH$_2$)$_2$O]$_{1-3}$CH$_3$, e.g., —(CH$_2$)$_2$OCH$_3$ and —[(CH$_2$)$_2$O]$_2$CH$_3$; —C$_{1-6}$ alkylene-OC(O)R$^{10}$, e.g., —CH$_2$OC(O)CH$_3$, —CH$_2$OC(O)CH$_2$CH$_3$, —CH$_2$OC(O)(CH$_2$)$_2$CH$_3$, —CH$_2$CH(CH$_3$)OC(O)CH$_2$CH$_3$, —CH$_2$OC(O)OCH$_3$, —CH$_2$OC(O)OCH$_2$CH$_3$, —CH(CH$_3$)OC(O)OCH$_2$CH$_3$, —CH(CH$_3$)OC(O)O—CH(CH$_3$)$_2$, —CH$_2$CH(CH$_3$)OC(O)-cyclopentyl, —CH$_2$OC(O)O-cyclopropyl, —CH(CH$_3$)—OC(O)—O-cyclohexyl, —CH$_2$OC(O)O-cyclopentyl, —CH$_2$CH(CH$_3$)OC(O)-phenyl, —CH$_2$OC(O)O-phenyl, —CH$_2$OC(O)—CH[CH(CH$_3$)$_2$]—NH$_2$, —CH$_2$OC(O)—CH[CH(CH$_3$)$_2$]—NHC(O)OCH$_3$, and —CH(CH$_3$)OC(O)—CH(NH$_2$)CH$_2$COOCH$_3$;

—C$_{1-6}$alkylene-NR$^{12}$R$^{13}$, e.g., —(CH$_2$)$_2$—N(CH$_3$)$_2$,

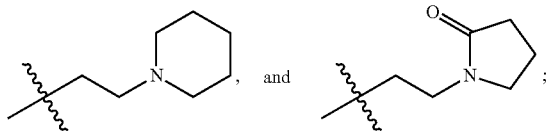 [SMILES: *CCN1CCCCC1 ; *CCN1CCCC1=O]

—C$_{1-6}$alkylene-C(O)R$^{31}$, e.g., —CH$_2$C(O)OCH$_3$, —CH$_2$C(O)O-benzyl, —CH$_2$C(O)—N(CH$_3$)$_2$, and

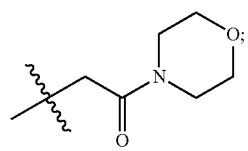 [SMILES: *CC(=O)N1CCOCC1]

—C$_{0-6}$alkylenemorpholinyl, e.g., —(CH$_2$)$_2$-morpholinyl and —(CH$_2$)$_3$-morpholinyl:

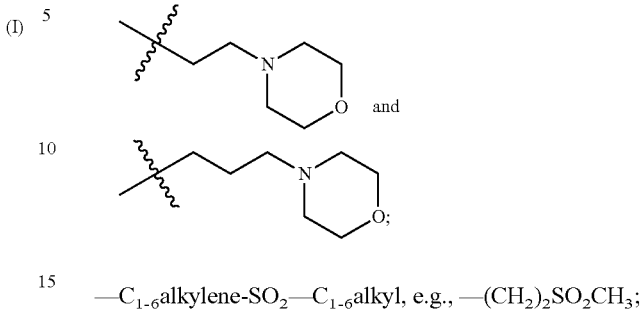

—C$_{1-6}$alkylene-SO$_2$—C$_{1-6}$alkyl, e.g., —(CH$_2$)$_2$SO$_2$CH$_3$;

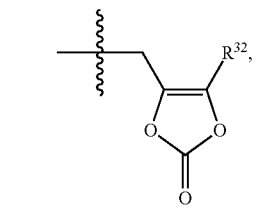

for example,

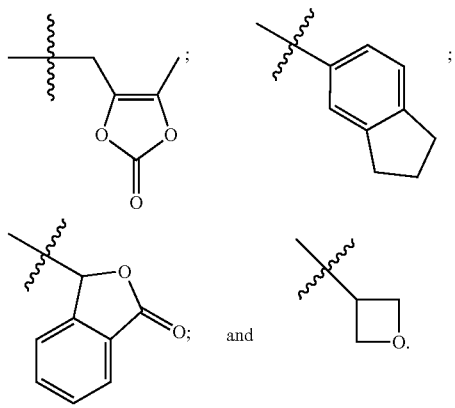

The R$^{10}$ moiety is selected from:

—C$_{1-6}$alkyl, e.g., —CH$_3$ and —CH$_2$CH$_3$;

—O—C$_{1-6}$alkyl, e.g., —OCH$_3$, —O—CH$_2$CH$_3$, and —O—CH(CH$_3$)$_2$;

—C$_{3-7}$cycloalkyl, e.g., cyclopentyl);

—O—C$_{3-7}$cycloalkyl, e.g., —O-cyclopropyl, —O-cyclohexyl, and —O-cyclopentyl;

phenyl;

—O-phenyl;

—NR$^{12}$R$^{13}$;

—CH[CH(CH$_3$)$_2$]—NH$_2$;

—CH[CH(CH$_3$)$_2$]—NHC(O)O—C$_{1-6}$alkyl, e.g., —CH[CH(CH$_3$)$_2$]—NHC(O)OCH$_3$; and

—CH(NH$_2$)CH$_2$COOCH$_3$.

The R$^{12}$ and R$^{13}$ moieties are independently selected from H, —C$_{1-6}$alkyl (e.g., CH$_3$), and benzyl. Alternately, the R$^{12}$ and R$^{13}$ moieties can be taken together as —(CH$_2$)$_{3-6}$—, —C(O)—(CH$_2$)$_3$—, or —(CH$_2$)$_2$O(CH$_2$)$_2$—, for example to form a group such as:

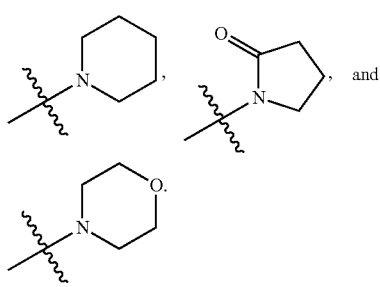

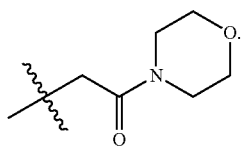 [SMILES: *CC(=O)N1CCOCC1]

The $R^{31}$ moiety is selected from —O—$C_{1-6}$alkyl, e.g., —OCH$_3$, —O-benzyl, and —NR$^{12}$R$^{13}$, e.g., —N(CH$_3$)$_2$, and

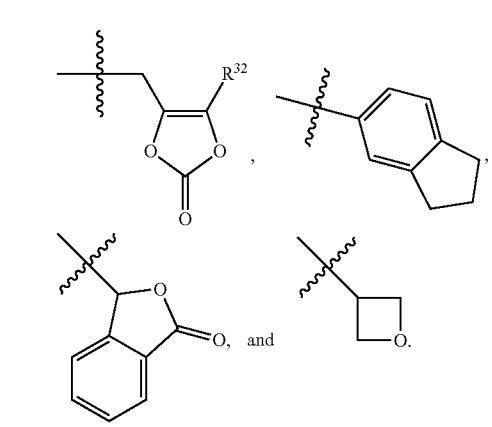

The $R^{32}$ moiety is —$C_{1-6}$alkyl (e.g., —CH$_3$ and —C(CH$_3$)$_3$) or —$C_{0-6}$alkylene-$C_{6-10}$aryl.

The $R^8$ moiety is selected from:
H;
—OH;
—OC(O)R$^{14}$, e.g., —OC(O)CH$_3$, —OC(O)-phenyl, —OC(O)—OCH$_2$-phenyl, —OC(O)—CH$_2$O-phenyl, —OC(O)(NH$_2$), and —OC(O)[N(CH$_3$)$_2$;
—CH$_2$COOH;
—O-benzyl;
pyridyl; and
—OC(S)NR$^{15}$R$^{16}$, e.g., —OC(S)NH$_2$ and —OC(S)N(CH$_3$)$_2$.

The $R^{14}$ moiety is selected from:
H;
—$C_{1-6}$alkyl, e.g., —CH$_3$;
—$C_{6-10}$aryl, e.g., phenyl;
—OCH$_2$—$C_{6-10}$aryl, e.g., —OCH$_2$-phenyl;
—CH$_2$O—$C_{6-10}$aryl, e.g., —CH$_2$O-phenyl; and
—NR$^{15}$R$^{16}$, e.g., —NH$_2$ and N(CH$_3$)$_2$.

The $R^{15}$ and $R^{16}$ moieties are independently selected from H and —$C_{1-4}$alkyl.

The $R^9$ is moiety selected from H, —$C_{1-6}$alkyl (e.g., —CH$_3$), and —C(O)R$^{17}$ (e.g., —C(O)H). The $R^{17}$ moiety is selected from H, —$C_{1-6}$alkyl (e.g., —CH$_2$CH$_3$), —$C_{3-7}$cycloalkyl (e.g., cyclopropyl), —$C_{6-10}$aryl (e.g., phenyl), and —$C_{1-9}$heteroaryl (e.g., pyridine).

In addition, each alkyl group in R$^1$ is optionally substituted with 1 to 8 fluoro atoms. For example, when R$^1$ is —OR$^7$ and R$^7$ is —$C_{1-8}$alkyl, R$^1$ can also be a group such as —OCH(CH$_3$)CF$_3$, —OCH$_2$CF$_2$CF$_3$, —OCH(CF$_3$)$_2$, —O(CH$_2$)$_2$CF$_3$, —OCH(CH$_2$F)$_2$, —OC(CF$_3$)$_2$CH$_3$, and —OCH(CH$_3$)CF$_2$CF$_3$.

In one embodiment, R$^1$ is —OR$^7$, and R$^7$ is H or —$C_{1-8}$alkyl. In other embodiments these compounds have formulas III-VIII.

In one embodiment, R$^1$ is selected from —OR$^7$ and —NR$^8$R$^9$, R$^7$ is H, R$^8$ is H or —OH, and R$^9$ is H. I In other embodiments these compounds have formulas III-VIII.

In another embodiment, R$^1$ is —OR$^7$, where R$^7$ is selected from —$C_{1-8}$alkyl, —$C_{1-3}$alkylene-$C_{6-10}$aryl, —$C_{1-3}$alkylene-$C_{1-9}$heteroaryl, —$C_{3-7}$cycloalkyl, —[(CH$_2$)$_2$O]$_{1-3}$CH$_3$, —$C_{1-6}$alkylene-OC(O)R$^{10}$, —$C_{1-6}$alkylene-NR$^{12}$R$^{13}$, —$C_{1-6}$alkylene-C(O)R$^{31}$, —$C_{0-6}$alkylenemorpholinyl; —$C_{1-6}$alkylene-SO$_2$—$C_{1-6}$alkyl;

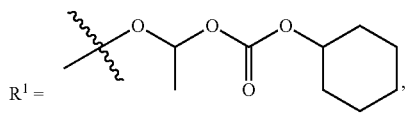 [SMILES: *OC(C)OC(=O)OC1CCCCC1]

In yet another embodiment, R$^1$ is —NR$^8$R$^9$; where R$^8$ is selected from —OC(O)R$^{14}$, —CH$_2$COOH, —O-benzyl, pyridyl, and —OC(S)NR$^{15}$R$^{16}$; and R$^9$ is H. In yet another embodiment, R$^1$ is —NR$^8$R$^9$, where R$^8$ is H or —OH; and R$^9$ is —$C_{1-6}$alkyl or —C(O)R$^{17}$. In yet another embodiment, R$^1$ is —NR$^8$R$^9$, where R$^8$ is selected from —OC(O)R$^{14}$, —CH$_2$COOH, —O-benzyl, pyridyl, and —OC(S)NR$^{15}$R$^{16}$; and R$^9$ is —$C_{1-6}$alkyl or —C(O)R$^{17}$. In other embodiments these compounds have formulas III-VIII. In one aspect of the invention, these compounds may find particular utility as prodrugs or as intermediates in the synthetic procedures described herein. For example, in one embodiment, R$^1$ is —OR$^7$ and R$^7$ is —$C_{1-6}$alkylene-OC(O)R$^{10}$, such as —O—CH(CH$_3$)OC(O)—O-cyclohexyl:

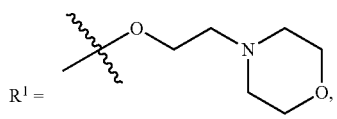 [SMILES: *OCCN1CCOCC1]

making the compound a cilexetil ester; or R$^1$ is —OR$^7$ and R$^7$ is —$C_{0-6}$alkylenemorpholinyl such as —O—(CH$_2$)$_2$-morpholinyl:

R$^1$ = [structure]

making the compound a 2-morpholinoethyl or mofetil ester; or R$^1$ is —OR$^7$ and R$^7$ is

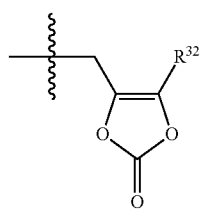

such as —O—CH$_2$-5-methyl-[1,3]dioxol-2-one:

R$^1$ = 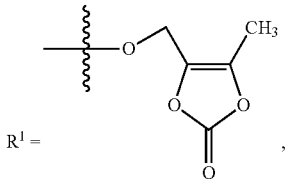, making the compound a medoxomil ester.

In one embodiment, R$^{2a}$ is —OH and R$^{2b}$ is —CH$_3$. In still another embodiment, R$^{2a}$ is —OP(O)(OH)$_2$ and R$^{2b}$ is —CH$_3$. In yet another embodiment, R$^{2a}$ is —OC(O)CH(R$^{37}$)NH$_2$, where R$^{37}$ is selected from H, —CH(CH$_3$)$_2$, phenyl, and benzyl, and R$^{2b}$ is —CH$_3$. In another embodiment, R$^{2a}$ and R$^{2b}$ are both —CH$_3$. In still another embodiment, R$^{2a}$ and R$^{2b}$ are taken together to form —CH$_2$—CH$_2$—. These can be depicted as formulas III, IV, V, VI, and VII respectively:

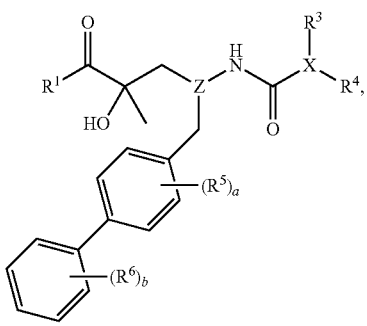 (III)

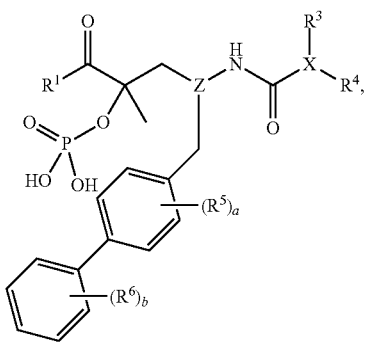 (IV)

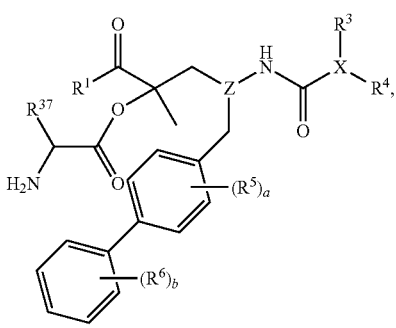 (V)

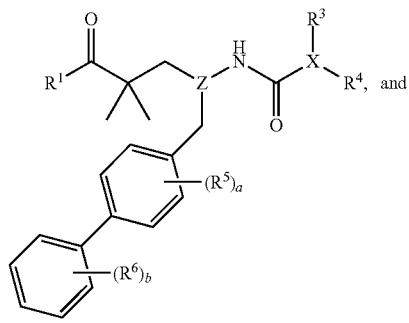 (VI)

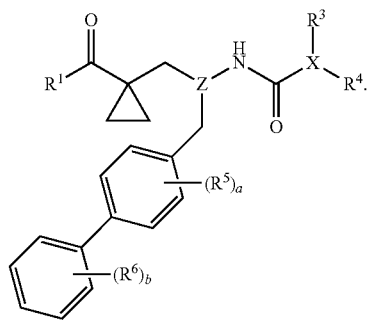 (VII)

In other embodiment, R$^{2a}$ is taken together with R$^7$ to form —OCR$^{18}$R$^{19}$— or is taken together with R$^8$ to form —OC(O)—. When R$^{2a}$ is taken together with R$^7$ to form —OCR$^{18}$R$^{19}$—, this embodiment can be depicted as:

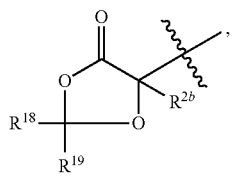

and when R$^{18}$ and R$^{19}$ are taken together to form =O, this embodiment can be depicted as:

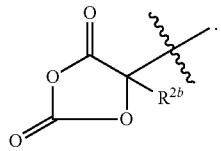

When R$^{2a}$ is taken together with R$^8$ to form —OC(O)—, this embodiment can be depicted as:

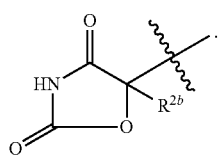

In one aspect of the invention, these compounds may find particular utility as prodrugs or as intermediates in the synthetic procedures described herein. Compounds where $R^{2a}$ is —OP(O)(OH)$_2$ may also find utility as prodrugs.

The "Z" moiety is —CH— or —N—, which can be depicted as formulas Ie and If, respectively:

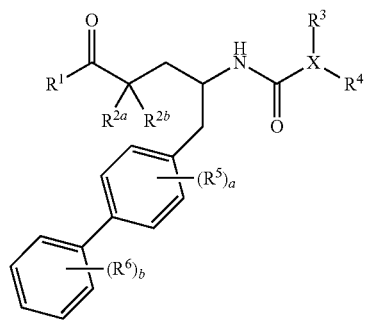
(Ie)

and

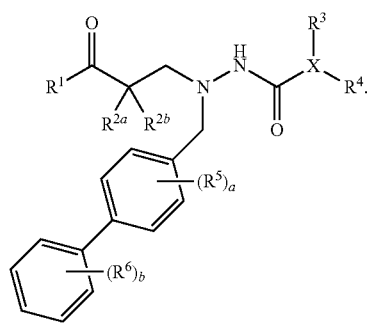
(If)

In one embodiment Z is —CH—, $R^{2a}$ is —OH, and $R^{2b}$ is —CH$_3$. In one embodiment Z is —CH—, $R^{2a}$ is —OP(O)(OH)$_2$, and $R^{2b}$ is —CH$_3$. In one embodiment Z is —CH—, $R^{2a}$ is —OC(O)CH(R$^{37}$)NH$_2$, and $R^{2b}$ is —CH$_3$. In another embodiment Z is —CH— and $R^{2a}$ and $R^{2b}$ are both —CH$_3$. In yet another embodiment Z is —CH— and $R^{2a}$ and $R^{2b}$ are taken together to form —CH$_2$—CH$_2$—. These embodiments can be depicted as formulas IIIa, IVa, Va, VIa, and VIIa, respectively:

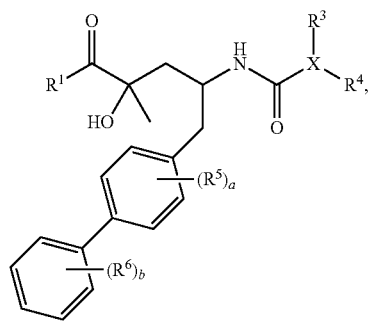
(IIIa)

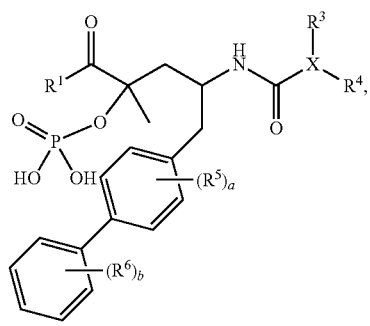
(IVa)

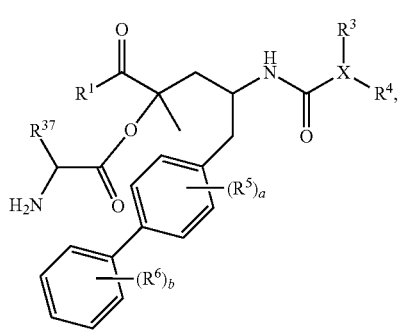
(Va)

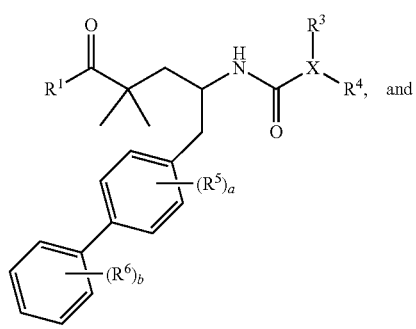
(VIa)

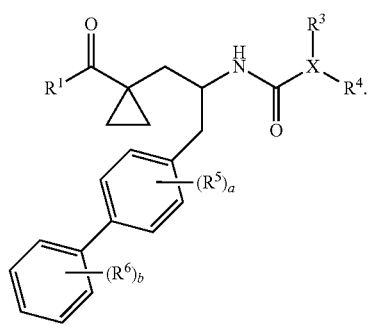
(VIIa)

In another embodiment Z is —N—, $R^{2a}$ is —OH, and $R^{2b}$ is —CH$_3$. In one embodiment Z is —N—, $R^{2a}$ is —OP(O)(OH)$_2$, and $R^{2b}$ is —CH$_3$. In one embodiment Z is —N—, $R^{2a}$ is —OC(O)CH(R$^{37}$)NH$_2$, and $R^{2b}$ is —CH$_3$. In another embodiment Z is —N— and $R^{2a}$ and $R^{2b}$ are both —CH$_3$. In yet another embodiment Z is —N— and $R^{2a}$ and $R^{2b}$ are taken together to form —CH$_2$—CH$_2$—. These embodiments can be depicted as formulas IIIb, IVb, Vb, VIb, and VIIb, respectively:

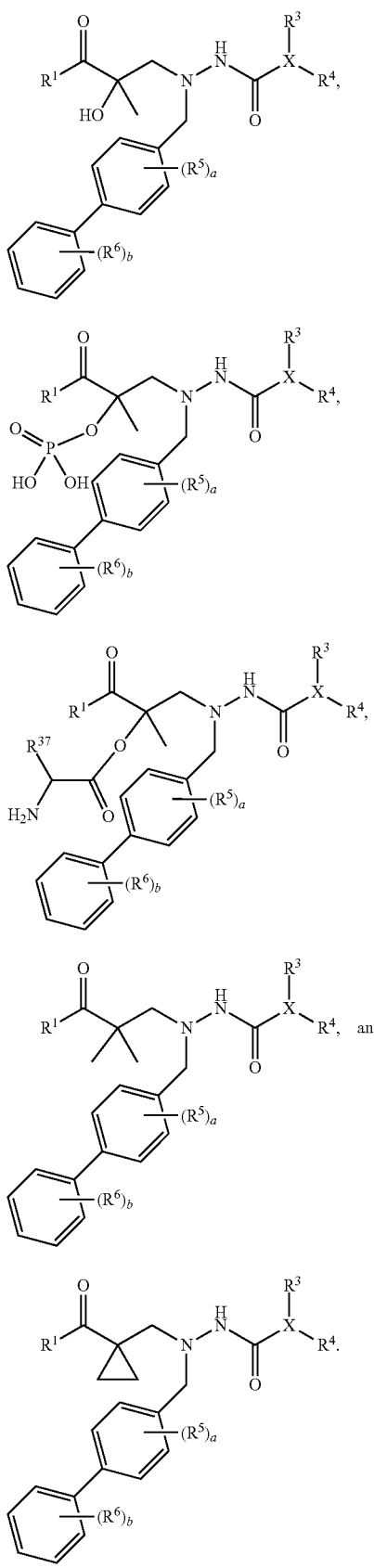

(IIIb)

(IVb)

(Vb)

(VIb)

(VIIb)

The "X" moiety is a —$C_{1-9}$heteroaryl, and the point of attachment is at any available carbon or nitrogen ring atom. Note that in some embodiments, $R^3$ and/or $R^4$ may be absent. When present, $R^3$ is on any available carbon atom. When present, $R^4$ is on any available carbon atom or nitrogen atom. Exemplary —$C_{1-9}$heteroaryl rings include, by way of illustration and not limitation:

pyrazole rings such as:

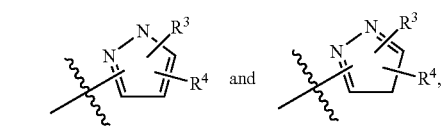

specific examples of which include:

imidazole rings such as:

specific examples of which include:

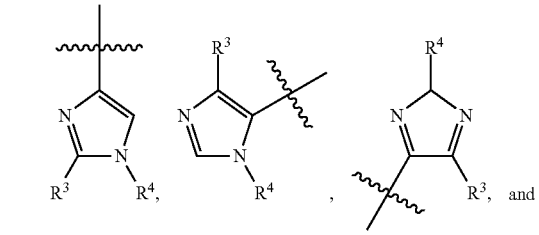

-continued
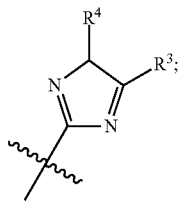
triazole rings, including 1,2,3-triazoles such as:
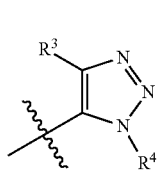 and 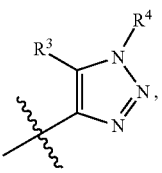,
as well as 1,2,4-triazoles such as:
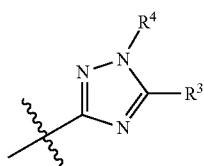 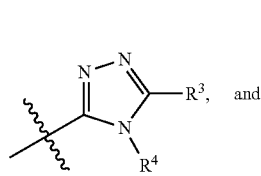 and
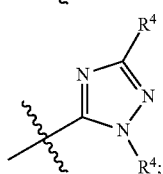
benzotriazole rings such as:
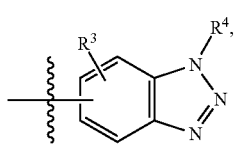
specific examples of which include:
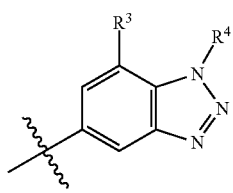
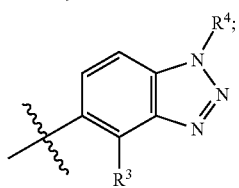
furan rings:
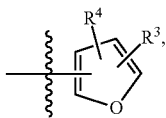
specific examples of which include:
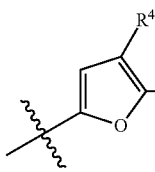 and 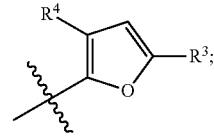;
pyrrole rings:
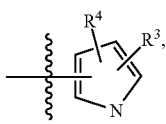
specific examples of which include:
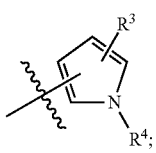
tetrazole rings such as:
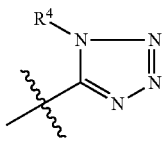 and 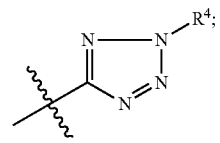;
pyrazine rings:
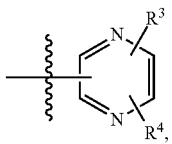
a specific example of which includes:
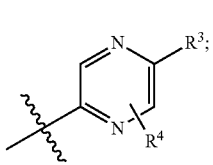

thiophene rings:
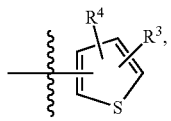
specific examples of which include:
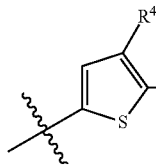 and 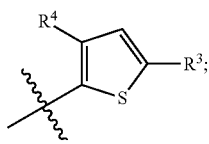
oxazole rings:
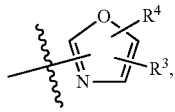
specific examples of which include:
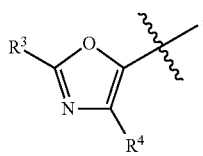, 
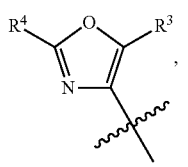, 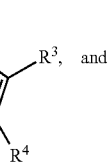 and
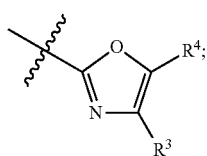
isoxazole rings:
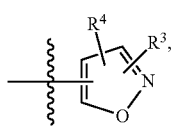
specific examples of which include:
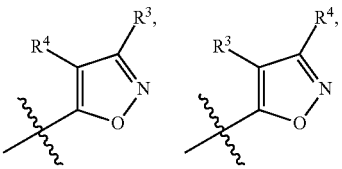
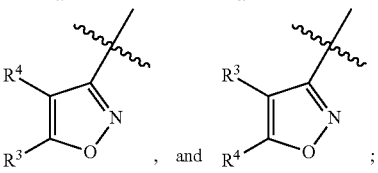, and ;
thiazole rings:
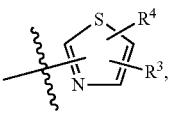
specific examples of which include:
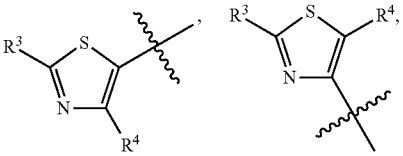
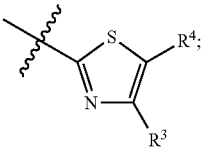
isothiazole rings:
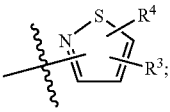
oxadiazole rings, including [1,2,4]oxadiazoles such as:
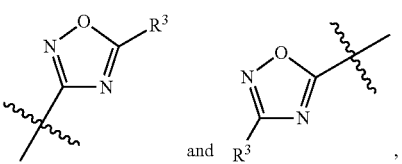
and , as well [1,2,3]oxadiazoles such as:
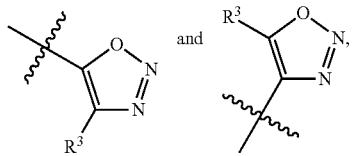
and [1,3,4]oxadiazoles:
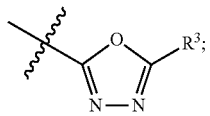
thiadiazole rings, including [1,2,4]thiadiazoles such as:
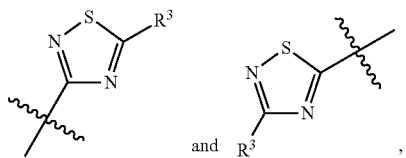
as well as [1,2,3]thiadiazoles such as:
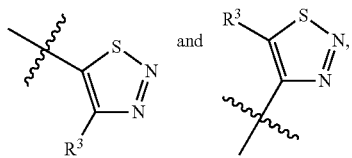
and [1,3,4]thiadiazoles:
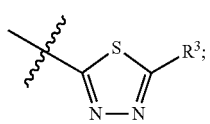
pyridazine rings:
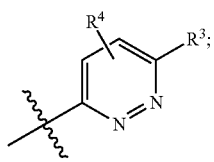
pyridine rings:
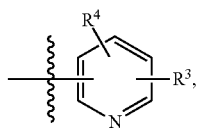
specific examples of which include:
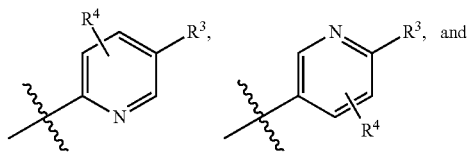
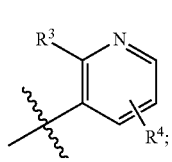
pyrimidine rings:
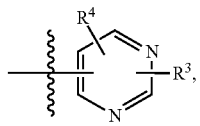
specific examples of which include:
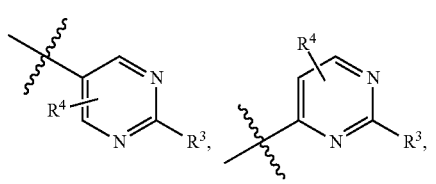
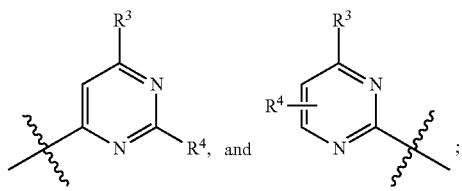
pyran rings such as:
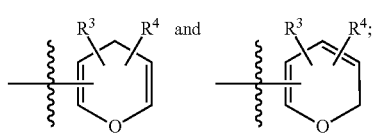

benzimidazole rings such as:
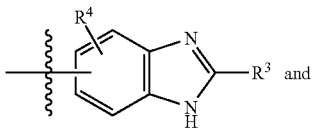
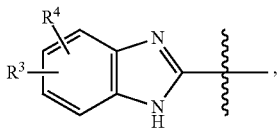
specific examples of which include:
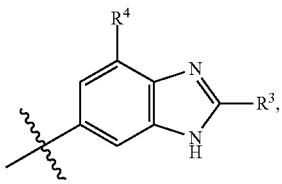
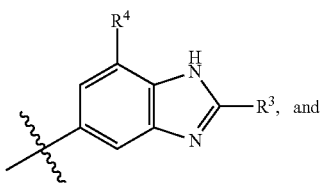
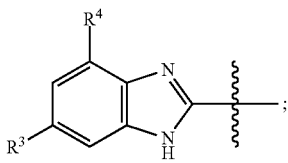
benzoxazole rings such as:
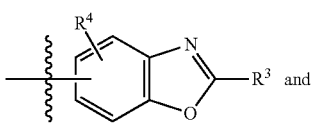
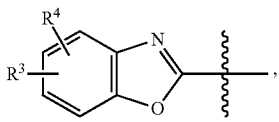
specific examples of which include:
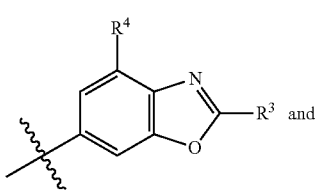
-continued
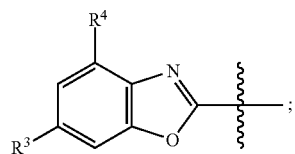
benzothiazole rings such as:
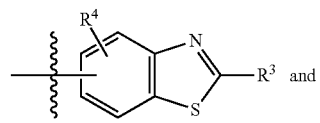
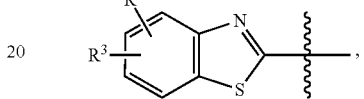
specific examples of which include:
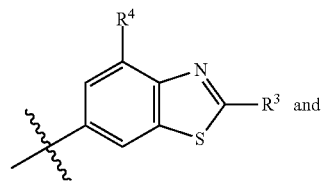
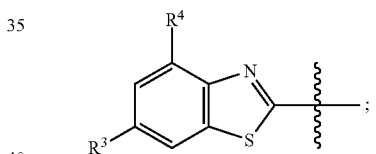
pyridylimidazole rings such as:
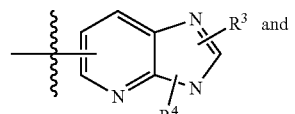
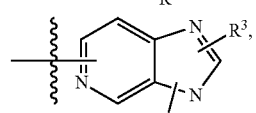
a specific example of which includes:
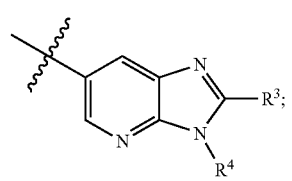

and pyridyltriazole rings such as:

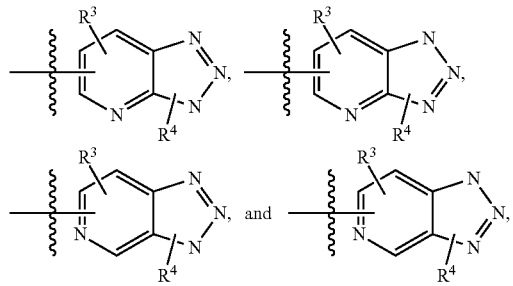

specific examples of which include:

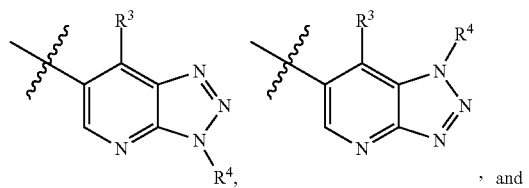

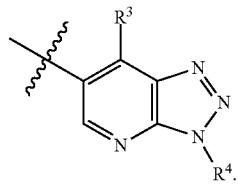

In one particular embodiment, X is selected from pyrazole, imidazole, triazole, benzotriazole, furan, pyrrole, tetrazole, pyrazine, thiophene, oxazole, isoxazole, thiazole, isothiazole, oxadiazole, thiadiazole, pyridazine, pyridine, pyrimidine, pyran, benzimidazole, benzoxazole, benzothiazole, pyridylimidazole, and pyridyltriazole. In other embodiments these compounds have formulas III-VI.

It is understood that some —$C_{1-9}$heteroaryl rings can exist in a tautomeric form, and that such tautomeric forms are part of the invention and are encompassed by the term "heteroaryl." Therefore, if a compound is depicted with a —$C_{1-9}$ heteroaryl ring, it is understood that the compound can also exist in a tautomeric form and vice versa, and that both forms are covered by the invention.

| —$C_{1-9}$heteroaryl ring | exemplary ring | exemplary tautomer(s) |
|---|---|---|
| pyrazole | 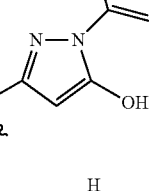 | 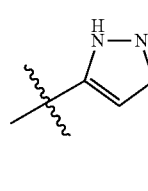 |
| imidazole | 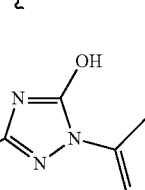 | 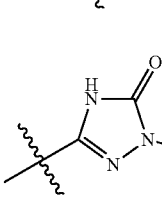 |
| triazole | 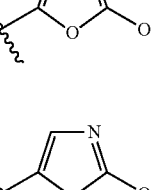 | 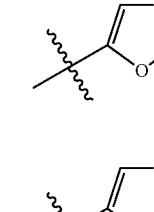 |
| oxazole |  |  |
| thiazole | | |

| —C$_{1-9}$heteroaryl ring | exemplary ring | exemplary tautomer(s) |
|---|---|---|
| isothiazole | | |
| oxdiazole | | |
| thiadiazole | | |
| pyridazine | | |

In one particular embodiment, X is selected from pyrazole, triazole, benzotriazole, tetrazole, oxazole, isoxazole, pyrimidine, and pyridyltriazole. In other embodiments these compounds have formulas III-VII. In still another embodiment X is triazole, and in one specific embodiment, have formula VIII:

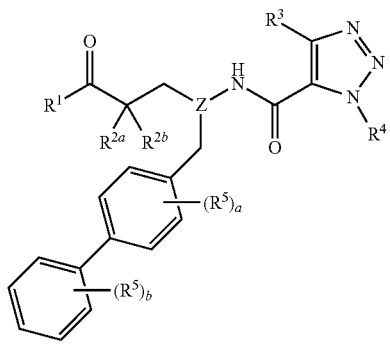

(VIII)

where Z, R$^1$, R$^{2a}$, R$^{2b}$, R$^3$-R$^6$, a, and b are as defined for formula I.

The R$^3$ moiety can be absent. When present, R$^3$ is attached to a carbon atom in the "X" group, and is selected from:

H;
halo, e.g., chloro and fluoro;
—C$_{0-5}$alkylene-OH, e.g., —OH, —CH$_2$OH, —CH(OH)CH$_3$, and —C(CH$_3$)$_2$—OH;
—NH$_2$;
—C$_{1-6}$alkyl, e.g., —CH$_3$, —(CH$_2$)$_2$CH$_3$, —CH(CH$_3$)$_2$, and —(CH$_2$)$_3$—CH$_3$;
—CF$_3$;
—C$_{3-7}$cycloalkyl, e.g., cyclopropyl and cyclohexyl;
—C$_{0-2}$alkylene-O—C$_{1-6}$alkyl, e.g., —OCH$_3$, —OCH$_2$CH$_3$, —CH$_2$—OCH$_3$, and —(CH$_2$)$_2$—OCH$_3$;
—C(O)R$^{20}$, e.g., —C(O)H and —C(O)CH$_3$;
—C$_{0-1}$alkylene-COOR$^{21}$, e.g., —COOH, —CH$_2$—COOH, —C(O)O—CH$_2$CH$_3$, —C(O)O—(CH$_2$)$_2$OCH$_3$—C(O)O—CH$_2$OC(O)CH$_3$, —CH$_2$—C(O)O—CH$_2$OC(O)CH$_3$, —C(O)O—CH$_2$OC(O)O—CH$_3$, —CH$_2$—C(O)O—CH$_2$OC(O)O—CH$_3$, —C(O)O—CH(CH$_3$)OC(O)O—CH$_2$CH$_3$, —C(O)O—CH(CH$_3$)OC(O)O—CH(CH$_3$)$_2$, —C(O)O—CH$_2$CH(CH$_3$)OC(O)-cyclopentyl, —C(O)O—CH$_2$OC(O)O-cyclopropyl, —C(O)O—CH(CH$_3$)—OC(O)—O-cyclohexyl, —C(O)O—CH$_2$OC(O)O-cyclopentyl, —C(O)O—CH$_2$CH(CH$_3$)OC(O)-phenyl, —C(O)O—CH$_2$OC(O)O-phenyl, —C(O)O—CH$_2$-pyridine, —C(O)O—CH$_2$-pyrrolidine, —C(O)O—(CH$_2$)$_2$-morpholinyl, —C(O)O—(CH$_2$)$_3$-morpholinyl, and —C(O)O—(CH$_2$)$_2$—SO$_2$—CH$_3$;
—C(O)NR$^{22}$R$^{23}$, e.g., —C(O)NH$_2$, —C(O)NHCH$_3$, —C(O)N(CH$_3$)$_2$, —C(O)NH—(CH$_2$)$_2$CH$_3$, —C(O)NH—CH$_2$COOH, —C(O)NH—(CH$_2$)$_2$—OH, —C(O)NH—(CH$_2$)$_2$—N(CH$_3$)$_2$, —C(O)NH-cyclopropyl, —C(O)NH—(CH$_2$)$_2$-imidazolyl, —C(O)N(CH$_3$)—CH$_2$CH(CH$_3$)$_2$, and —C(O)N(CH$_3$)[(CH$_2$)$_2$OCH$_3$];
—NHC(O)R$^{24}$, e.g., —NHC(O)—CH$_2$CH$_3$, —NHC(O)—(CH$_2$)$_3$CH$_3$, —NHC(O)O—CH$_2$CH$_3$, —NHC(O)—CH$_2$—OCH$_3$, —NHC(O)-2-methoxyphenyl, —NHC(O)-2-chlorophenyl, and —NHC(O)-2-pyridine;
═O;
—NO$_2$;
—C(CH$_3$)═N(OH);
phenyl optionally substituted with one or two groups independently selected from halo, —OH, —CF$_3$, —OCH$_3$, —NHC(O)CH$_3$, and phenyl (e.g., phenyl, 2-chlorophenyl, 2-fluorophenyl, 2-hydroxyphenyl, 2-trifluoromethylphenyl, 2-methoxyphenyl, 3-chlorophenyl, 3-fluorophenyl, 3-methoxyphenyl, 3-NHC(O)CH$_3$-phenyl, 4-chlorophenyl, 4-fluorophenyl, 4-methoxyphenyl, 4-biphenyl, 2,5-dichlorophenyl, 2,5-dimethoxyphenyl, 2,4-dichlorophenyl, 2-methoxy, 5-fluorophenyl, and 3,4-dichlorophenyl);
naphthalenyl;
pyridinyl;
pyrazinyl;
pyrazolyl optionally substituted with methyl; thiophenyl optionally substituted with methyl or halo (e.g., chloro);
furanyl; and
—CH$_2$-morpholinyl.

The $R^{20}$ moiety is selected from H and —$C_{1-6}$ alkyl (e.g., —$CH_3$). The $R^{21}$ moiety is selected from:
  H;
  —$C_{1-6}$alkyl, e.g., —$CH_3$ and —$CH_2CH_3$;
  —$C_{1-3}$alkylene-$C_{6-10}$aryl;
  —$C_{1-3}$alkylene-$C_{1-9}$heteroaryl, e.g., —$CH_2$-pyridine;
  $C_{3-7}$cycloalkyl;
  —[($CH_2)_2O]_{1-3}CH_3$, e.g., —($CH_2)_2OCH_3$;
  —$C_{1-6}$alkylene-OC(O)$R^{25}$, e.g., —$CH_2OC(O)CH_3$, —$CH_2OC(O)O—CH_3$, —$CH_2OC(O)O—CH_3$, —$CH(CH_3)OC(O)O—CH_2CH_3$, —$CH(CH_3)OC(O)O—CH(CH_3)_2$, —$CH_2CH(CH_3)OC(O)$-cyclopentyl, —$CH_2OC(O)O$-cyclopropyl, —$CH(CH_3)—OC(O)—O$-cyclohexyl, —$CH_2OC(O)$O-cyclopentyl, —$CH_2CH(CH_3)OC(O)$-phenyl, and —$CH_2OC(O)$O-phenyl;
  —$C_{1-6}$alkylene-$NR^{27}R^{28}$, e.g., —$CH_2$-pyrrolidine;
  —$C_{1-6}$alkylene-C(O)$R^{33}$;
  —$C_{0-6}$alkylenemorpholinyl, e.g., —($CH_2)_2$-morpholinyl and —($CH_2)_3$-morpholinyl:

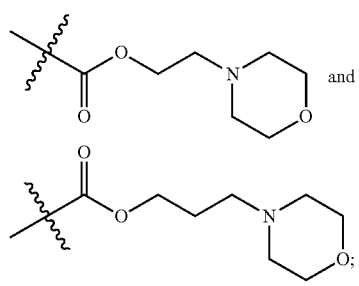

—$C_{1-6}$alkylene-$SO_2$—$C_{1-6}$alkyl, e.g., —($CH_2)_2$—$SO_2$—$CH_3$;

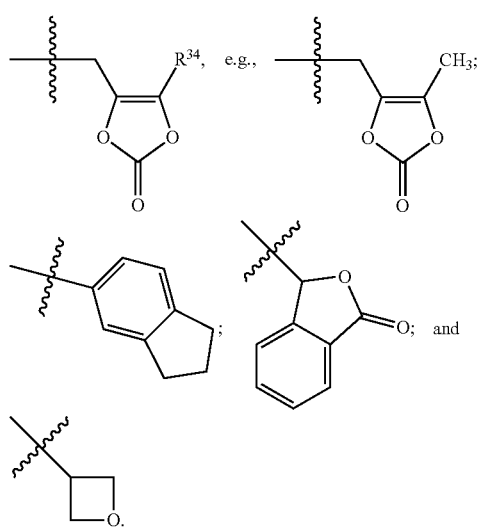

The $R^{22}$ and $R^{23}$ moieties are independently selected from:
  H;
  —$C_{1-6}$alkyl, e.g., —$CH_3$ and —($CH_2)_2CH_3$;
  —$CH_2COOH$;
  —($CH_2)_2OH$;
  —($CH_2)_2OCH_3$;
  —($CH_2)_2SO_2NH_2$;
  ($CH_2)_2N(CH_3)_2$;
  —$C_{0-1}$alkylene-$C_{3-7}$cycloalkyl, e.g., cyclopropyl and —$CH_2$-cyclopropyl; and
  —($CH_2)_2$-imidazolyl.

$R^{22}$ and $R^{23}$ may also be taken together to form a saturated or partially unsaturated —$C_{3-5}$heterocycle optionally substituted with halo, —OH, —COOH, or —$CONH_2$, and optionally containing an oxygen atom in the ring. Saturated —$C_{3-5}$ heterocycles include azetidine, pyrrolidine, piperidine and morpholine, such that exemplary $R^3$ groups include:

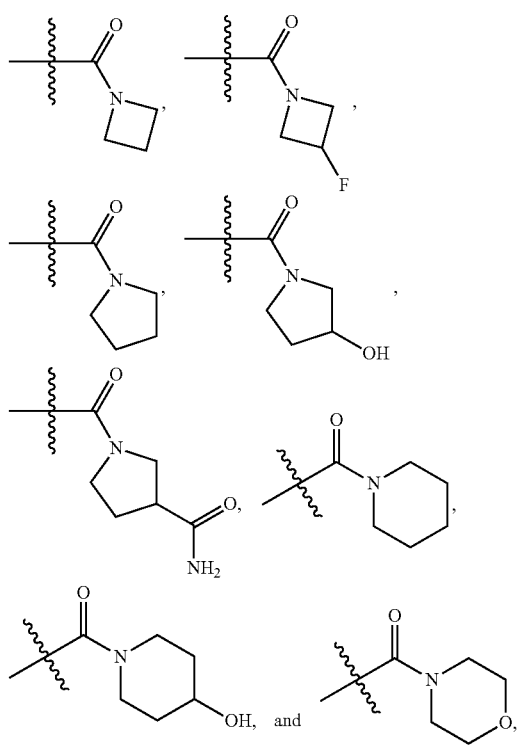

Partially unsaturated —$C_{3-5}$heterocycles include 2,5-dihydro-1H-pyrrole, such that exemplary $R^3$ groups include:

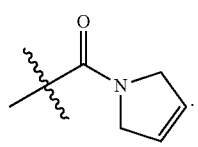 [SMILES: *C(=O)N1CC=CC1]

The $R^{24}$ moiety is selected from:
  —$C_{1-6}$alkyl, e.g., —$CH_2CH_3$ and —($CH_2)_3CH_3$;
  —$C_{0-1}$alkylene-O—$C_{1-6}$alkyl, e.g., —O—$CH_2CH_3$ and —$CH_2$—$OCH_3$;
  phenyl optionally substituted with halo or —$OCH_3$, e.g., -2-chlorophenyl or -2-methoxyphenyl; and
  —$C_{1-9}$heteroaryl, e.g., 2-pyridine.

$R^{25}$ is selected from:
  —$C_{1-6}$alkyl, e.g., —$CH_3$, —$CH_2CH_3$, and —($CH_2)_3CH_3$;
  —O—$C_{1-6}$alkyl, e.g., —$OCH_3$, —$OCH_2CH_3$, and —$OCH(CH_3)_2$;
  —$C_{3-7}$cycloalkyl, e.g., cyclopentyl;
  —O—$C_{3-7}$cycloalkyl, e.g., —O-cyclopropyl, —O-cyclopentyl, and —O-cyclohexyl;
  phenyl;
  —O-phenyl;

—$NR^{27}R^{28}$;
—$CH[CH(CH_3)_2]$—$NH_2$;
—$CH[CH(CH_3)_2]$—$NHC(O)O$—$C_{1-6}$alkyl, e.g., —$CH[CH(CH_3)_2]$—$NHC(O)OCH_3$; and
—$CH(NH_2)CH_2COOCH_3$.

$R^{27}$ and $R^{28}$ are independently selected from H, —$C_{1-6}$alkyl, and benzyl, or $R^{27}$ and $R^{28}$ are taken together as —$(CH_2)_{3-6}$—, —$C(O)$—$(CH_2)_3$—, or —$(CH_2)_2O(CH_2)_2$—; $R^{33}$ is selected from —$O$—$C_{1-6}$alkyl, —$O$-benzyl, and —$NR^{27}R^{28}$; and $R^{34}$ is —$C_{1-6}$alkyl (e.g., —$CH_3$ and —$C(CH_3)_3$) or —$C_{0-6}$alkylene-$C_{6-10}$aryl.

In addition, each alkyl group in $R^3$ is optionally substituted with 1 to 8 fluoro atoms. For example, when $R^3$ is —$C_{0-1}$alkylene-$COOR^{21}$ and $R^{21}$ is —$C_{1-6}$alkyl, $R^3$ can also be a group such as —$COOCH(CH_3)CF_3$, —$COOCH_2CF_2CF_3$, —$COOCH(CF_3)_2$, —$COO(CH_2)_2CF_3$, —$COOCH(CH_2F)_2$, —$COOC(CF_3)_2CH_3$, and —$COOCH(CH_3)CF_2CF_3$.

In one embodiment, $R^3$ is absent or is selected from H, halo, —$C_{0-5}$alkylene-OH, —$C_{0-1}$alkylene-$O$—$C_{1-6}$alkyl, —$C(O)R^{20}$, —$C_{0-1}$alkylene-$COOR^{21}$, —$C(O)NR^{22}R^{23}$, =O, and pyrazinyl; $R^{20}$ is —$C_{1-6}$alkyl; $R^{21}$ is selected from H and —$C_{1-6}$alkyl; $R^{22}$ and $R^{23}$ are independently selected from H, —$C_{1-6}$alkyl, —$(CH_2)_2OCH_3$, and —$(CH_2)_2$-imidazolyl; or $R^{22}$ and $R^{23}$ are taken together to form a saturated —$C_{3-5}$ heterocycle optionally substituted with —OH or —COOH, and optionally containing an oxygen atom in the ring. In other embodiments these compounds have formulas III-VIII.

In one embodiment, $R^3$ is absent or is selected from H; halo; —$C_{0-5}$alkylene-OH; —$NH_2$; —$C_{1-6}$alkyl; —$CF_3$; —$C_{3-7}$cycloalkyl; —$C_{0-2}$alkylene-$O$—$C_{1-6}$alkyl; —$C(O)R^{20}$; —$C_{0-1}$alkylene-$COOR^{21}$; —$C(O)NR^{22}R^{23}$; —$NHC(O)R^{24}$; =O; —$NO_2$; —$C(CH_3)$=$N(OH)$; phenyl optionally substituted with one or two groups independently selected from halo, —OH, —$CF_3$, —$OCH_3$, —$NHC(O)CH_3$, and phenyl; naphthalenyl; pyridinyl; pyrazinyl; pyrazolyl optionally substituted with methyl; thiophenyl optionally substituted with methyl or halo; furanyl; and —$CH_2$-morpholinyl; and $R^{21}$ is H. In other embodiments these compounds have formulas III-VIII.

In another embodiment, $R^3$ is —$C_{0-1}$alkylene-$COOR^{21}$, and $R^{21}$ is selected from —$C_{1-6}$alkyl, —$C_{1-3}$alkylene-$C_{6-10}$aryl, —$C_{1-3}$alkylene-$C_{1-9}$heteroaryl, —$C_{3-7}$cycloalkyl, —$[(CH_2)_2O]_{1-3}CH_3$, —$C_{1-6}$alkylene-$OC(O)R^{25}$; —$C_{1-6}$alkylene-$NR^{27}R^{28}$, —$C_{1-6}$alkylene-$C(O)R^{33}$, —$C_{0-6}$alkylenemorpholinyl, —$C_{1-6}$alkylene-$SO_2$—$C_{1-6}$alkyl,

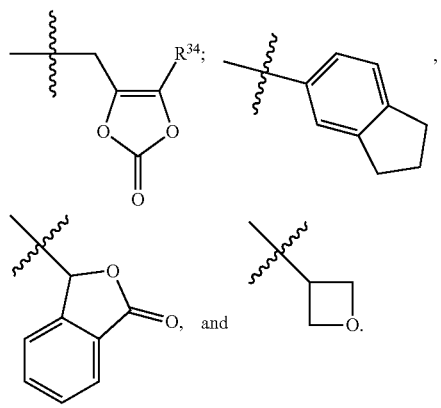

thetic procedures described herein. In other embodiments these compounds have formulas III-VIII.

The $R^4$ moiety can be absent. When present, $R^4$ is attached to a carbon or nitrogen atom in the "X" group, and is selected from:

H;
—OH;
—$C_{1-6}$alkyl, e.g., —$CH_3$;
—$C_{1-2}$alkylene-$COOR^{35}$, e.g., —$CH_2COOH$ and —$(CH_2)_2$—COOH;
—$CH_2OC(O)CH(R^{36})NH_2$, e.g., —$CH_2OC(O)CH[CH(CH_3)_2]NH_2$;
—$OCH_2OC(O)CH(R^{36})NH_2$, e.g., —$OCH_2OC(O)CH[CH(CH_3)_2]NH_2$;
—$OCH_2OC(O)CH_3$;
—$CH_2OP(O)(OH)_2$;
—$CH_2CH(OH)CH_2OH$;
—$CH[CH(CH_3)_2]$—$NHC(O)O$—$C_{1-6}$alkyl;
pyridinyl; and
phenyl or benzyl optionally substituted with one or more groups selected from halo, —$COOR^{35}$, —$OCH_3$, —$OCF_3$, and —$SCF_3$ (e.g., 4-chlorophenyl, 3-methoxyphenyl, 2,4-dichlorophenyl, 3,4-dichlorophenyl, 2-chloro, 5-fluorophenyl, 3-trifluoromethoxy, 4-chlorophenyl, 3-trifluoromethylsulfanyl, 4-chlorophenyl, 2,6-difluoro, 4-chlorophenyl, 2-chlorobenzyl, 3-chlorobenzyl, 4-chlorobenzyl, 3-carboxybenzyl, 4-carboxybenzyl, 3-methoxybenzyl, 2-chloro, 5-fluorobenzyl, 3-chloro, 5-fluorobenzyl, 2-fluoro, 4-chlorobenzyl, 3-chloro, 4-fluorobenzyl, 3-OCF3,4-chlorobenzyl, 3-SCF3,4-chlorobenzyl, 2,6-difluoro, 3-chlorobenzyl, 2,6-difluoro, 4-chlorobenzyl, and 2,3,5,6-tetrafluoro, 4-methoxy benzyl).

The $R^{35}$ moiety is selected from:
H;
—$C_{1-6}$alkyl, e.g., —$CH_3$ and —$CH_2CH_3$;
—$C_{1-3}$alkylene-$C_{6-10}$aryl;
—$C_{1-3}$alkylene-$C_{1-9}$heteroaryl, e.g., —$CH_2$-pyridine;
—$C_{3-7}$cycloalkyl;
—$[(CH_2)_2O]_{1-3}CH_3$, e.g., —$(CH_2)_2OCH_3$;
—$C_{1-6}$alkylene-$OC(O)R^{25}$, e.g., —$CH_2OC(O)CH_3$, —$CH_2OC(O)O$—$CH_3$, —$CH_2OC(O)O$—$CH_3$, —$CH(CH_3)OC(O)O$—$CH_2CH_3$, —$CH(CH_3)OC(O)O$—$CH(CH_3)_2$, —$CH_2CH(CH_3)OC(O)$-cyclopentyl, —$CH_2OC(O)O$-cyclopropyl, —$CH(CH_3)$—$OC(O)$—$O$-cyclohexyl, —$CH_2OC(O)O$-cyclopentyl, —$CH_2CH(CH_3)OC(O)$-phenyl, and —$CH_2OC(O)O$-phenyl;
—$C_{1-6}$alkylene-$NR^{27}R^{28}$, e.g., —$CH_2$-pyrrolidine;
—$C_{1-6}$alkylene-$C(O)R^{33}$;
—$C_{0-6}$alkylenemorpholinyl, e.g., —$(CH_2)_2$-morpholinyl and —$(CH_2)_3$-morpholinyl:

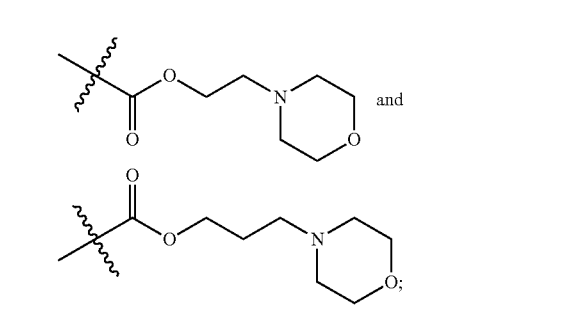

In one aspect of the invention, these compounds may find particular utility as prodrugs or as intermediates in the syn- —$C_{1-6}$alkylene-$SO_2$—$C_{1-6}$alkyl, e.g., —$(CH_2)_2$—$SO_2$—$CH_3$;

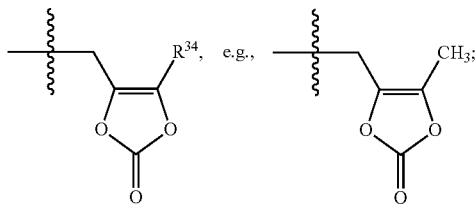

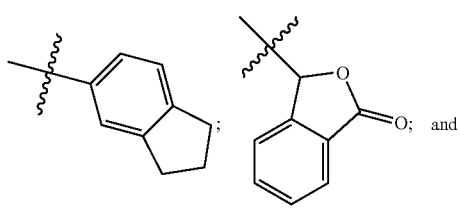

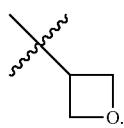

The $R^{25}$, $R^{27}$, $R^{28}$, $R^{33}$, and $R^{34}$ moieties are defined above. The $R^{36}$ moiety is selected from H, —$CH(CH_3)_2$, phenyl, and benzyl.

In addition, each alkyl group in $R^4$ is optionally substituted with 1 to 8 fluoro atoms. For example, when $R^4$ is —$C_{1-2}$alkylene-$COOR^{35}$ and $R^{35}$ is —$C_{1-6}$alkyl, $R^4$ can also be a group such as —$COOCH(CH_3)CF_3$, —$COOCH_2CF_2CF_3$, —$COOCH(CF_3)_2$, —$COO(CH_2)_2CF_3$, —$COOCH(CH_2F)_2$, —$COOC(CF_3)_2CH_3$, and —$COOCH(CH_3)CF_2CF_3$.

The $R^4$ moiety can also be taken together with $R^3$ to form phenylene-O—$(CH_2)_{1-3}$— or -phenylene-O—$CH_2$—CHOH—$CH_2$—. For purposes of illustration only, these embodiments are depicted below with X being pyrazole. It is understood that other X groups can be used also.

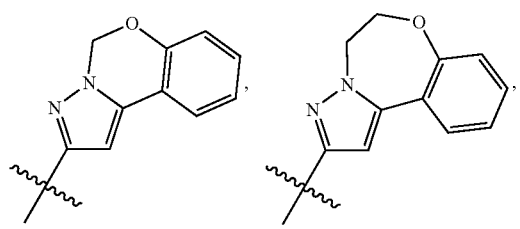

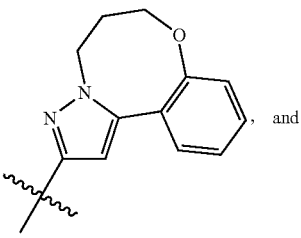

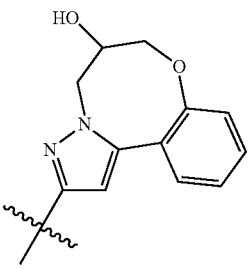

In another particular embodiment, $R^4$ is selected from H and —OH. In other embodiments these compounds have formulas III-VIII.

In one embodiment, $R^4$ is absent or is selected from H; —OH; —$C_{1-6}$alkyl; —$C_{1-2}$alkylene-$COOR^{35}$; —$CH_2OC(O)CH(R^{36})NH_2$, —$CH_2CH(OH)CH_2OH$; pyridinyl; and phenyl or benzyl optionally substituted with one or more groups selected from halo, —$COOR^{35}$, —$OCH_3$, —$OCF_3$, and —$SCF_3$; and $R^{35}$ is H. In other embodiments these compounds have formulas III-VIII.

In another embodiment, $R^4$ is selected from —$OCH_2OC(O)CH_3$; —$CH_2OP(O)(OH)_2$; —$C_{1-2}$alkylene-$COOR^{35}$; and phenyl or benzyl substituted with at least one —$COOR^{35}$ group; where $R^{35}$ is selected from —$C_{1-6}$alkyl, —$C_{1-3}$alkylene-$C_{6-10}$aryl, —$C_{1-3}$alkylene-$C_{1-9}$heteroaryl, —$C_{3-7}$cycloalkyl, —$[(CH_2)_2O]_{1-3}CH_3$, —$C_{1-6}$alkylene-$OC(O)R^{25}$; —$C_{1-6}$alkylene-$NR^{27}R^{28}$, —$C_{1-6}$alkylene-$C(O)R^{33}$, —$C_{0-6}$alkylenemorpholinyl, —$C_{1-6}$alkylene-$SO_2$—$C_{1-6}$alkyl,

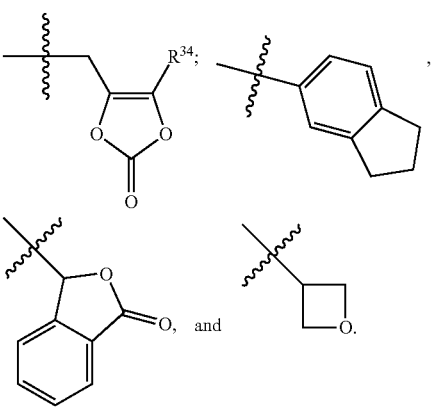

In one aspect of the invention, these compounds may find particular utility as prodrugs or as intermediates in the synthetic procedures described herein. In other embodiments these compounds have formulas III-VIII.

The numbering for the R⁵ and R⁶ groups is as follows:

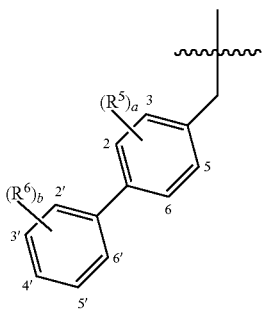

The integer "a" is 0 or 1. The R⁵ moiety, when present, is selected from halo, —CH₃, —CF₃, and —CN. In one embodiment, a is 0. In another embodiment, a is 1, and R⁵ is halo, such as 3-chloro or 3-fluoro. The integer "b" is 0 or an integer from 1 to 3. The R⁶ moiety, when present, is independently selected from halo, —OH, —CH₃, —OCH₃, and —CF₃. In one embodiment, b is 0. In another embodiment, b is 1 and R⁶ is selected from halo, —OH, —CH₃, —OCH₃, and —CF₃, such 2'-chloro, 3'-chloro, 2'-fluoro, 3'-fluoro, 2'-hydroxy, 3'-hydroxy, 3'-methyl, 2'-methoxy, or 3'-trifluoromethyl. In another embodiment, b is 1 and R⁶ is selected from halo, —OH, and —OCH₃, such 2'-chloro, 3'-chloro, 2'-fluoro, 3'-fluoro, 2'-hydroxy, or 2'-methoxy. In one embodiment, b is 2 and R⁶ is 2'-fluoro-5'-chloro, 2',5'-dichloro, 2',5'-difluoro, 2'-methyl-5'-chloro, 3'-fluoro-5'-chloro, 3'-hydroxy-5'-chloro, 3',5'-dichloro, 3',5'-difluoro, 2'-methoxy-5'-chloro, 2'-methoxy-5'-fluoro, 2'-hydroxy-5'-fluoro, 2'-fluoro-3'-chloro, 2'-hydroxy-5'-chloro, or 2'-hydroxy-3'-chloro; and in another embodiment, b is 2 and each R⁶ is independently selected from halo and —CH₃, for example, 2'-fluoro-5'-chloro, 2',5'-difluoro, 2',5'-dichloro, 3',5'-dichloro, and 2'-methyl-5'-chloro. In another embodiment, b is 3 and each R⁶ is independently halo or —CH₃, such as 2'-methyl-3',5'-dichloro or 2'-fluoro-3'-methyl-5'-chloro. In yet another embodiment, a is 1 and b is 1 and R⁵ and R⁶ are independently halo, for example, 3-chloro and 3' chloro. In other embodiments these compounds have formulas III-VIII. Of particular interest are compounds of the formulas:

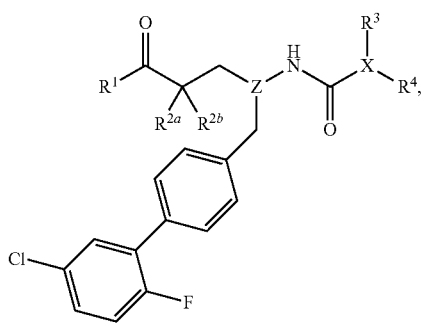

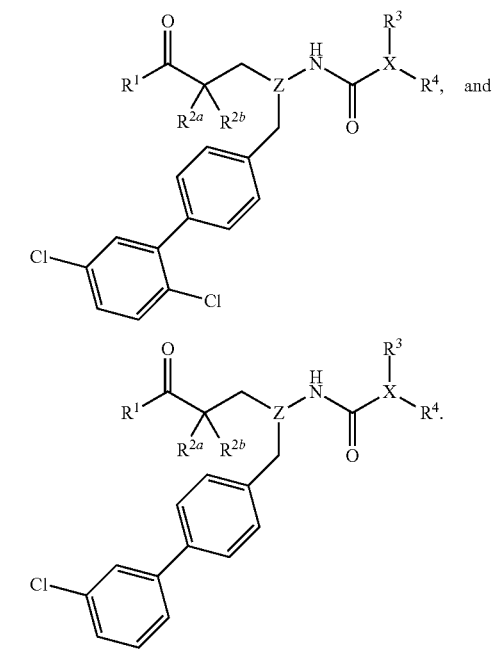

The methylene linker on the biphenyl is optionally substituted with one or two —C₁₋₆alkyl groups or cyclopropyl. For example, in one embodiment, the methylene linker on the biphenyl is unsubstituted; in another embodiment, the methylene linker on the biphenyl is substituted with one —C₁₋₆ alkyl group (e.g., —CH₃); and in yet another embodiment, the methylene linker on the biphenyl is substituted with two —C₁₋₆alkyl groups (e.g., two —CH₃ groups); in another embodiment, the methylene linker on the biphenyl is substituted with a cyclopropyl group. These embodiments are depicted, respectively, as:

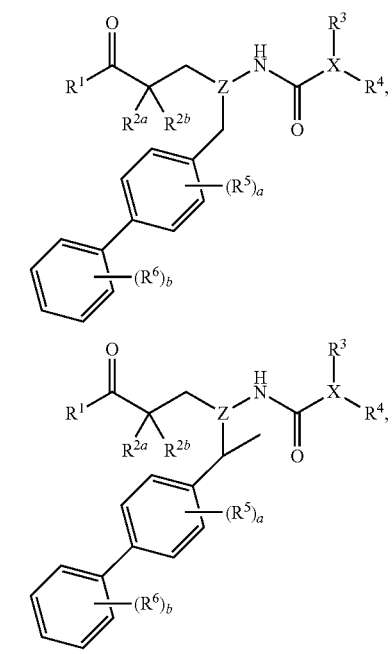

-continued

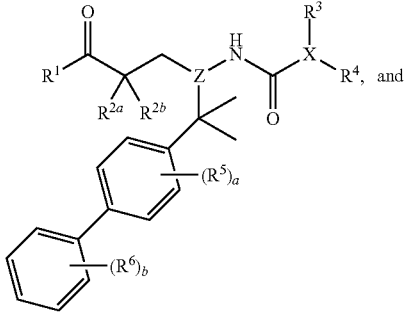

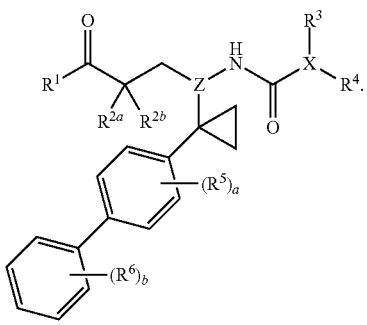

In another embodiment, $R^1$ is —$OR^7$; $R^7$ is H or —$C_{1-6}$alkyl; X is selected from pyrazole, triazole, benzotriazole, tetrazole, oxazole, isoxazole, pyrimidine, and pyridyltriazole; $R^3$ is absent or is selected from H, halo, —$C_{0-5}$alkylene-OH, —$C_{0-1}$alkylene-O—$C_{1-6}$alkyl, —$C(O)R^{20}$, —$C_{0-1}$alkylene-COOR$^{21}$, —$C(O)NR^{22}R^{23}$, =O, and pyrazinyl; $R^{20}$ is —$C_{1-6}$alkyl; $R^{21}$ is H or —$C_{1-6}$alkyl; $R^{22}$ and $R^{23}$ are independently selected from H, —$C_{1-6}$alkyl, —$(CH_2)_2OCH_3$, and —$(CH_2)_2$-imidazolyl; or $R^{22}$ and $R^{23}$ are taken together to form a saturated —$C_{3-5}$heterocycle optionally substituted with —OH or —COOH, and optionally containing an oxygen atom in the ring; $R^4$ is selected from H and —OH; a is 0; b is 0; or b is 1 and $R^6$ is selected from halo, —OH, and —$OCH_3$; or b is 2 and each $R^6$ is independently selected from halo and —$CH_3$; and Z, $R^{2a}$, and $R^{2b}$ are as defined for formula I.

In still another embodiment, $R^1$ is —$OR^7$, $R^{2a}$ is —OH and $R^{2b}$ is —$CH_3$; or $R^{2a}$ and $R^{2b}$ are both —$CH_3$; or $R^{2a}$ and $R^{2b}$ are taken together to form —$CH_2$—$CH_2$—; X is selected from pyrazole, triazole, isoxazole, and pyrimidine; $R^3$ is selected from H, —$C_{0-5}$alkylene-OH, and —$C_{0-1}$alkylene-COOR$^{21}$; $R^{21}$ is H or —$C_{1-6}$alkyl; $R^4$ is selected from H and —OH; a is 0; and b is 0; or b is 1 and $R^6$ is halo; or b is 2 and each $R^6$ is independently selected from halo and —$CH_3$; and $R^7$ is as defined for formula I.

A particular group of compounds of formula I are those disclosed in U.S. Provisional Application No. 61/443,828, filed on Feb. 17, 2011. This group includes compounds of formula II:

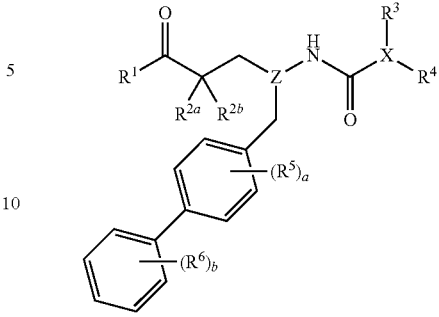

where: $R^1$ is selected from —$OR^7$ and —$NR^8R^9$; $R^7$ is selected from H; —$C_{1-6}$alkyl; —$C_{1-3}$alkylene-$C_{6-10}$aryl; —$C_{1-3}$alkylene-$C_{1-9}$heteroaryl; —$C_{3-7}$cycloalkyl; —$[(CH_2)_2 O]_{1-3}CH_3$; —$C_{1-6}$alkylene-OC(O)R$^{10}$; —$CH_2$-pyridine; —$CH_2$-pyrrolidine; —$C_{0-6}$alkylenemorpholine; —$C_{1-6}$alkylene-$SO_2$—$C_{1-6}$alkyl;

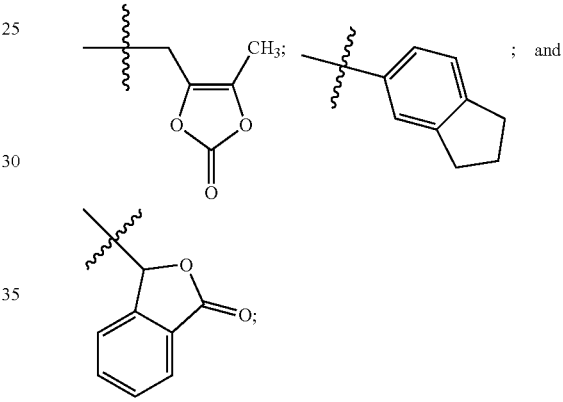

where $R^{10}$ is selected from —$C_{1-6}$alkyl, —O—$C_{1-6}$alkyl, —$C_{3-7}$cycloalkyl, —O—$C_{3-7}$cycloalkyl, phenyl, —O-phenyl, —$NR^{12}R^{13}$, and —$CH(NH_2)CH_2COOCH_3$; and $R^{12}$ and $R^{13}$ are independently selected from H, —$C_{1-6}$alkyl, and benzyl, or $R^{12}$ and $R^{13}$ are taken together as —$(CH_2)_{3-6}$—; $R^8$ is selected from H; —OH; —$OC(O)R^{14}$; —$CH_2COOH$; —O-benzyl; pyridyl; and —$OC(S)NR^{15}R^{16}$; where $R^{14}$ is selected from H, —$C_{1-6}$alkyl, —$C_{6-10}$aryl, —$OCH_2$—$C_{6-10}$aryl, —$CH_2O$—$C_{6-10}$aryl, and —$NR^{15}R^{16}$; and $R^{15}$ and $R^{16}$ are independently selected from H and —$C_{1-4}$alkyl; $R^9$ is selected from H; —$C_{1-6}$alkyl; and —$C(O)R^{17}$; where $R^{17}$ is selected from H; —$C_{1-6}$alkyl; —$C_{3-7}$cycloalkyl; —$C_{6-10}$aryl; and —$C_{1-9}$heteroaryl; $R^{2a}$ is —OH and $R^{2b}$ is —$CH_3$; or $R^{2a}$ and $R^{2b}$ are both —$CH_3$; or $R^{2a}$ and $R^{2b}$ are taken together to form —$CH_2$—$CH_2$—; Z is selected from —CH— and —N—; X is a —$C_{1-9}$heteroaryl or a partially unsaturated —$C_{3-5}$heterocycle; $R^3$ is absent or is selected from H; halo; —$C_{0-5}$alkylene-OH; —$NH_2$; —$C_{1-6}$alkyl; —$CF_3$; —$C_{3-7}$cycloalkyl; —$C_{0-1}$alkylene-O—$C_{1-6}$alkyl; —$C(O)R^{20}$; —$C_{0-1}$alkylene-C(O)OR$^{21}$; —$C(O)NR^{22}R^{23}$; —$NHC(O)R^{24}$; phenyl optionally substituted with one group selected from halo, —$CF_3$, —$OCH_3$, —$NHC(O)CH_3$, and phenyl; napthyl; pyridine; pyrazine; pyrazole optionally substituted with methyl; thiophene optionally substituted with methyl; and furan; and $R^3$, when present, is attached to a carbon atom; $R^{20}$ is selected from H and —$C_{1-6}$alkyl; $R^{21}$ is selected from H; —$C_{1-6}$alkyl; —$C_{1-3}$alkylene-$C_{6-10}$aryl; —$C_{1-3}$alkylene-$C_{1-9}$heteroaryl;

—$C_{3-7}$cycloalkyl; —$[(CH_2)_2O]_{1-3}CH_3$; —$C_{1-6}$alkylene-OC(O)$R^{25}$; —$CH_2$-pyridine; —$CH_2$-pyrrolidine; —$C_{0-6}$alkylenemorpholine; —$C_{1-6}$alkylene-$SO_2$—$C_{1-6}$alkyl;

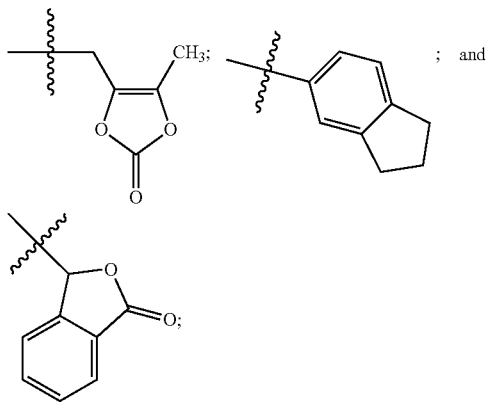

where $R^{25}$ is selected from —$C_{1-6}$alkyl, —O—$C_{1-6}$alkyl, —$C_{3-7}$cycloalkyl, —O—$C_{3-7}$cycloalkyl, phenyl, —O-phenyl, —$NR^{27}R^{28}$, and —$CH(NH_2)CH_2COOCH_3$; and $R^{27}$ and $R^{28}$ are independently selected from H, —$C_{1-6}$alkyl, and benzyl, or $R^{27}$ and $R^{28}$ are taken together as —$(CH_2)_{3-6}$—; $R^{22}$ and $R^{23}$ are independently selected from H; —$C_{1-6}$alkyl; —$CH_2COOH$; —$(CH_2)_2OH$; —$(CH_2)_2OCH_3$; —$(CH_2)_2SO_2NH_2$; —$(CH_2)_2N(CH_3)_2$; —$C_{3-7}$cycloalkyl; and —$(CH_2)_2$-imidazole; or $R^{22}$ and $R^{23}$ are taken together to form a saturated or partially unsaturated —$C_{3-5}$heterocycle optionally substituted with —OH, —COOH, or —$CONH_2$; and optionally containing an oxygen atom in the ring; $R^{24}$ is selected from —$C_{1-6}$alkyl; —$C_{0-1}$alkylene-O—$C_{1-6}$alkyl; phenyl optionally substituted with —$OCH_3$; and —$C_{1-9}$heteroaryl; $R^4$ is absent or is selected from H; —$C_{1-6}$alkyl; and phenyl or benzyl substituted with one or more groups selected from halo, —COOH, —$OCH_3$, —$OCF_3$, and —$SCF_3$; and $R^4$, when present, is attached to a carbon or nitrogen atom; a is 0 or 1; $R^5$ is halo, —$CH_3$, or —$CF_3$; and b is 0 or 1; $R^6$ is halo; or a pharmaceutically acceptable salt thereof.

In addition, particular compounds of formula I that are of interest include those set forth in the Examples below, as well as pharmaceutically acceptable salts thereof.

General Synthetic Procedures

Compounds of the invention can be prepared from readily available starting materials using the following general methods, the procedures set forth in the Examples, or by using other methods, reagents, and starting materials that are known to those of ordinary skill in the art. Although the following procedures may illustrate a particular embodiment of the invention, it is understood that other embodiments of the invention can be similarly prepared using the same or similar methods or by using other methods, reagents and starting materials known to those of ordinary skill in the art. It will also be appreciated that where typical or preferred process conditions (for example, reaction temperatures, times, mole ratios of reactants, solvents, pressures, etc.) are given, other process conditions can also be used unless otherwise stated. In some instances, reactions were conducted at room temperature and no actual temperature measurement was taken. It is understood that room temperature can be taken to mean a temperature within the range commonly associated with the ambient temperature in a laboratory environment, and will typically be in the range of about 18° C. to about 30° C. In other instances, reactions were conducted at room temperature and the temperature was actually measured and recorded. While optimum reaction conditions will typically vary depending on various reaction parameters such as the particular reactants, solvents and quantities used, those of ordinary skill in the art can readily determine suitable reaction conditions using routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions and reagents for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Fourth Edition, Wiley, New York, 2006, and references cited therein.

Carboxy-protecting groups are suitable for preventing undesired reactions at a carboxy group, and examples include, but are not limited to, methyl, ethyl, t-butyl, benzyl (Bn), p-methoxybenzyl (PMB), 9-fluorenylmethyl (Fm), trimethylsilyl (TMS), t-butyldimethylsilyl (TBDMS), diphenylmethyl (benzhydryl, DPM) and the like. Amino-protecting groups are suitable for preventing undesired reactions at an amino group, and examples include, but are not limited to, t-butoxycarbonyl (BOC), trityl (Tr), benzyloxycarbonyl (Cbz), 9-fluorenylmethoxycarbonyl (Fmoc), formyl, trimethylsilyl (TMS), t-butyldimethylsilyl (TBDMS), and the like. Hydroxyl-protecting groups are suitable for preventing undesired reactions at a hydroxyl group, and examples include, but are not limited to $C_{1-6}$alkyls, silyl groups including tri$C_{1-6}$alkylsilyl groups, such as trimethylsilyl (TMS), triethylsilyl (TES), and tert-butyldimethylsilyl (TBDMS); esters (acyl groups) including $C_{1-6}$alkanoyl groups, such as formyl, acetyl, and pivaloyl, and aromatic acyl groups such as benzoyl; arylmethyl groups such as benzyl (Bn), p-methoxybenzyl (PMB), 9-fluorenylmethyl (Fm), and diphenylmethyl (benzhydryl, DPM); and the like.

Standard deprotection techniques and reagents are used to remove the protecting groups, and may vary depending upon which group is used. For example, sodium or lithium hydroxide is commonly used when the carboxy-protecting group is methyl, an acid such as TFA or HCl is commonly used when the carboxy-protecting group is ethyl or t-butyl, and $H_2$/Pd/C may be used when the carboxy-protecting group is benzyl. A BOC amino-protecting group can be removed using an acidic reagent such as TFA in DCM or HCl in 1,4-dioxane, while a Cbz amino-protecting group can be removed by employing catalytic hydrogenation conditions such as $H_2$ (1 atm) and 10% Pd/C in an alcoholic solvent ("$H_2$/Pd/C"). $H_2$/Pd/C is commonly used when the hydroxyl-protecting group is benzyl, while NaOH is commonly used when the hydroxyl-protecting group is an acyl group.

Suitable bases for use in these schemes include, by way of illustration and not limitation, potassium carbonate, calcium carbonate, sodium carbonate, triethylamine, pyridine, 1,8-diazabicyclo-[5.4.0]undec-7-ene (DBU), N,N-diisopropylethylamine (DIPEA), 4-methylmorpholine, sodium hydroxide, potassium hydroxide, potassium t-butoxide, and metal hydrides.

Suitable inert diluents or solvents for use in these schemes include, by way of illustration and not limitation, tetrahydrofuran (THF), acetonitrile (MeCN), N,N-dimethylformamide (DMF), N,N-dimethylacetamide (DMA), dimethyl sulfoxide (DMSO), toluene, dichloromethane (DCM), chloroform (CHCl$_3$), carbon tetrachloride (CCl$_4$), 1,4-dioxane, methanol, ethanol, water, and the like.

Suitable carboxylic acid/amine coupling reagents include benzotriazol-1-yloxytris(dimethylamino)phosphonium hexafluorophosphate (BOP), benzotriazol-1-yloxytripyrrolidinophosphonium hexafluorophosphate (PyBOP), N,N,N',N'-tetramethyl-O-(7-azabenzotriazol-1-yl)uronium hexafluorophosphate (HATU), 1,3-dicyclohexylcarbodiimide (DCC), N-(3-dimethylaminopropyl)-N'-ethylcarbodiimide (EDCI), carbonyldiimidazole (CDI), 1-hydroxybenzotriazole (HOBt), and the like. Coupling reactions are conducted in an inert diluent in the presence of a base such as DIPEA, and are performed under conventional amide bond-forming conditions.

All reactions are typically conducted at a temperature within the range of about −78 C to 100° C., for example at room temperature. Reactions may be monitored by use of thin layer chromatography (TLC), high performance liquid chromatography (HPLC), and/or LCMS until completion. Reactions may be complete in minutes, or may take hours, typically from 1-2 hours and up to 48 hours. Upon completion, the resulting mixture or reaction product may be further treated in order to obtain the desired product. For example, the resulting mixture or reaction product may be subjected to one or more of the following procedures: concentrating or partitioning (for example, between EtOAc and water or between 5% THF in EtOAc and 1M phosphoric acid); extraction (for example, with EtOAc, CHCl$_3$, DCM, chloroform); washing (for example, with saturated aqueous NaCl, saturated NaHCO$_3$, Na$_2$CO$_3$ (5%), CHCl$_3$ or 1M NaOH); drying (for example, over MgSO$_4$, over Na$_2$SO$_4$, or in vacuo); filtering; crystallizing (for example, from EtOAc and hexane); being concentrated (for example, in vacuo); and/or purification (e.g., silica gel chromatography, flash chromatography, preparative HPLC, reverse phase-HPLC, or crystallization).

Compounds of formula I, as well as their salts, can be prepared as shown in Scheme I:

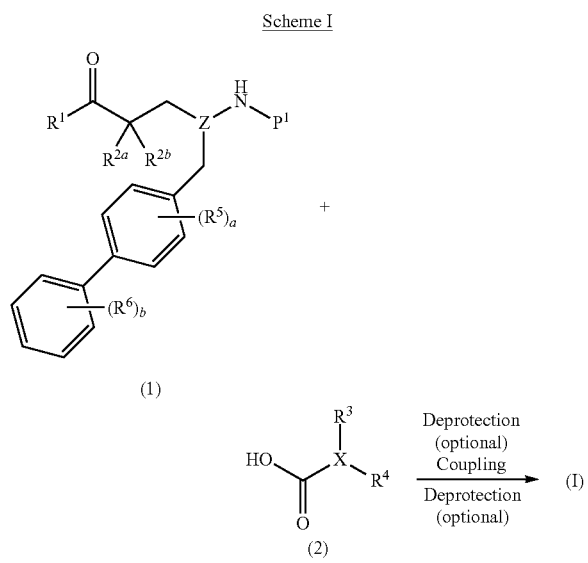

The process comprises the step of coupling compound 1 with compound 2, where R$^1$, R$^{2a}$, R$^{2b}$, R$^3$-R$^6$, X, Z, a, and b are as defined for formula I, and P$^1$ is H or a suitable amino-protecting group, examples of which include, t-butoxycarbonyl, trityl, benzyloxycarbonyl, 9-fluorenylmethoxycarbonyl, formyl, trimethylsilyl, and t-butyldimethylsilyl. When P$^1$ is an amino protecting group, the process further comprises deprotecting the compound of formula 1, before or in situ with the coupling step.

In instances where R$^1$ is a group such as —OCH$_3$ or —OCH$_2$CH$_3$, the coupling step may be followed by a deprotection step to provide a compound of formula I where R$^1$ is a group such as —OH. Thus, one method of preparing compounds of the invention involves coupling compounds 1 and 2, with an optional deprotection step to form a compound of formula I or a pharmaceutically acceptable salt thereof.

Methods of preparing compound 1 are described in the Examples. Compound 2 is generally commercially available or can be prepared using procedures that are known in the art.

Compounds of formula I, as well as their salts, can also be prepared as shown in Scheme II:

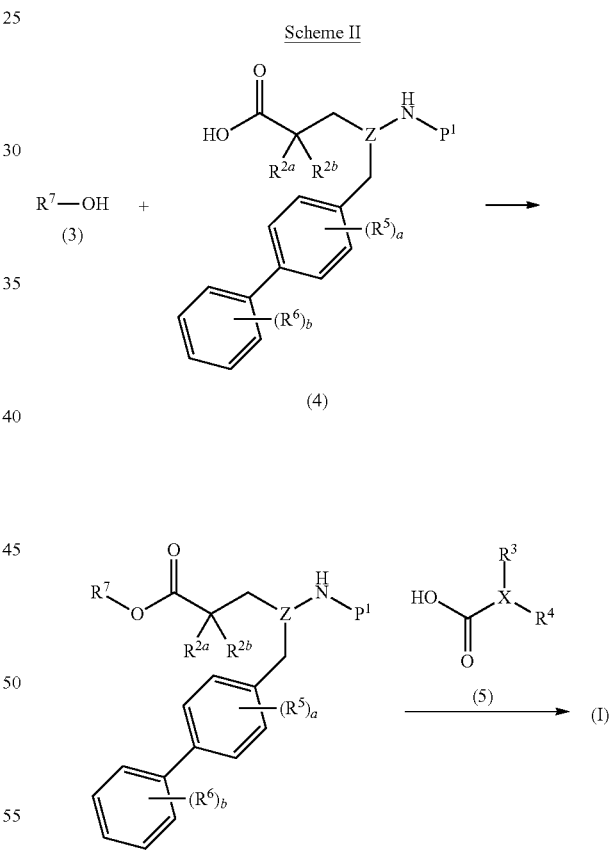

In this method, compound 3 is coupled with compound 4, the amine is deprotected and the intermediate is then coupled to 5 to form a compound of formula I or a pharmaceutically acceptable salt thereof. Methods of preparing compound 4 are described in the Examples. Compounds 3 and 5 are generally commercially available or can be prepared using procedures that are known in the art.

Compounds of formula I, as well as their salts, can also be prepared as shown in Scheme III:

Scheme III

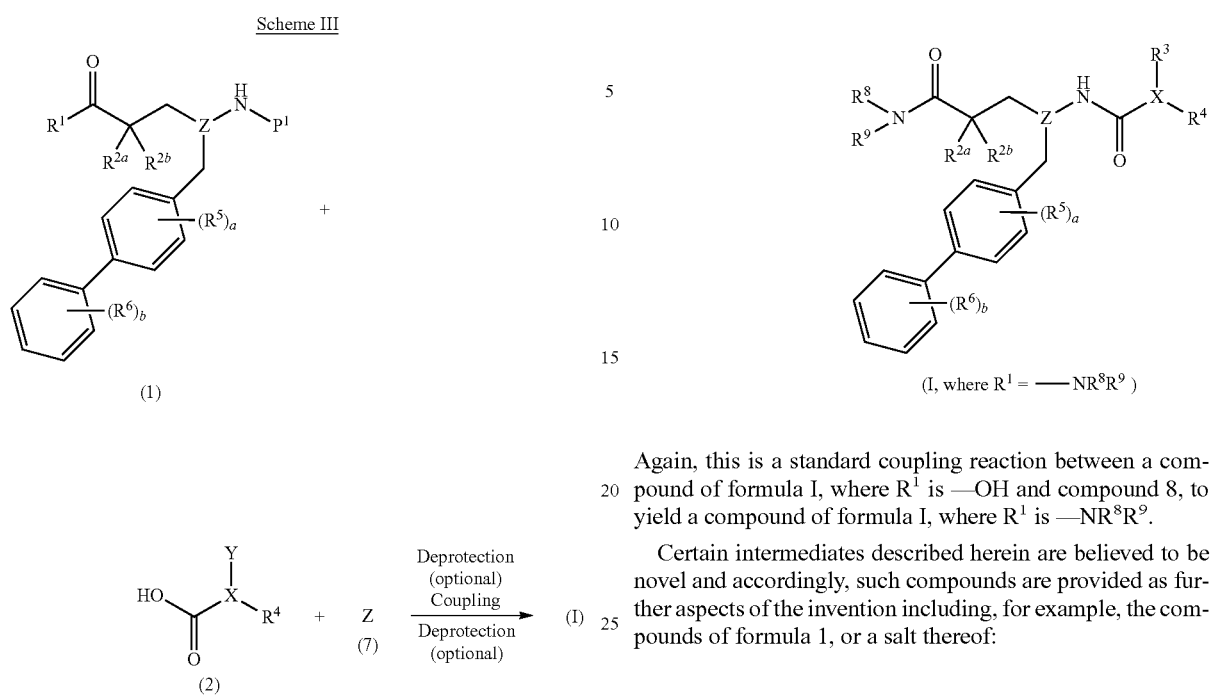

In the first step, compound 1 is coupled with compound 6 and compound 6 is coupled to compound 7, where Y and Z react in situ to form the $R^3$ moiety. For example, when $R^3$ is —C(O)NR$^{22}$R$^{23}$, Y is —COOH and Z is HNR$^{22}$R$^{23}$. Alternately, compound 6 is first coupled to compound 7, and the resulting compound is then coupled with compound 1. As with Scheme I, in instances where $R^1$ is a group such as —OCH$_3$ or —OCH$_2$CH$_3$, the coupling step may be followed by a deprotection step to provide a compound of formula I where $R^1$ is a group such as —OH. Thus, one method of preparing compounds of the invention involves coupling compounds 1, 2 and 3, with an optional deprotection step to form a compound of formula I or a pharmaceutically acceptable salt thereof. Compounds 6 and 7 are generally commercially available or can be prepared using procedures that are known in the art.

Compounds of formula I, as well as their salts, can also be prepared as shown in Scheme IV:

Scheme IV

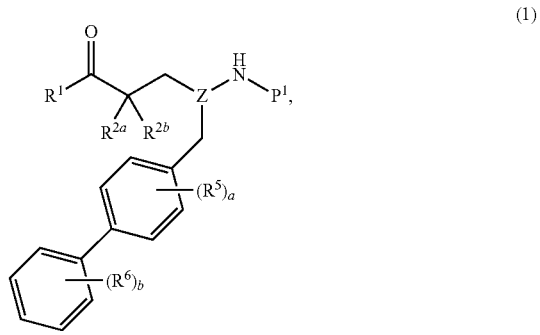

Again, this is a standard coupling reaction between a compound of formula I, where $R^1$ is —OH and compound 8, to yield a compound of formula I, where $R^1$ is —NR$^8$R$^9$.

Certain intermediates described herein are believed to be novel and accordingly, such compounds are provided as further aspects of the invention including, for example, the compounds of formula 1, or a salt thereof:

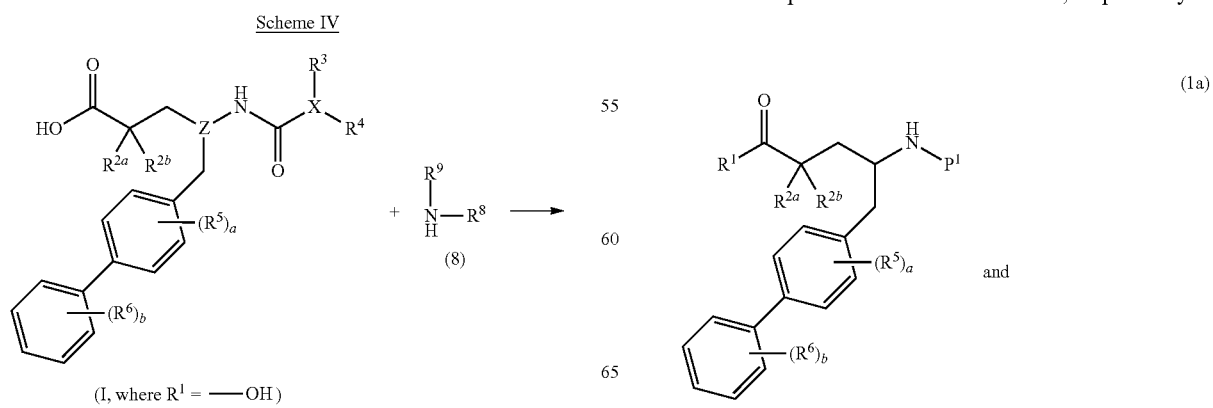

where $P^1$ is H or an amino-protecting group selected from t-butoxycarbonyl, trityl, benzyloxycarbonyl, 9-fluorenylmethoxycarbonyl, formyl, trimethylsilyl, and t-butyldimethylsilyl; and $R^1$, $R^{2a}$, $R^{2b}$, $R^5$, $R^6$, Z, a and b are as defined for formula I. In one specific embodiment Z is —CH— and in another specific embodiment Z is —N—. These embodiments can be depicted as formulas 1a and 1b, respectively:

-continued (1b)
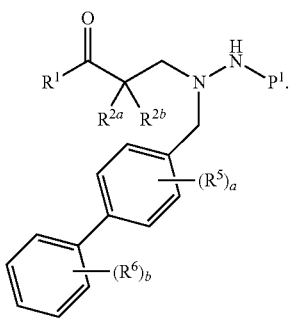

Another intermediate of the invention has formula 9 or a salt thereof:

(9)
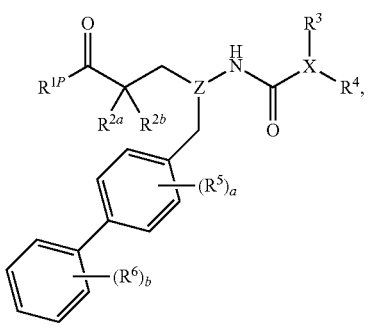

where $R^{1P}$ is selected from —O—$P^3$, —NH$P^2$, and —NH(O—$P^4$); where $P^2$ is an amino-protecting group selected from t-butoxycarbonyl, trityl, benzyloxycarbonyl, 9-fluorenylmethoxycarbonyl, formyl, trimethylsilyl, and t-butyldimethylsilyl; $P^3$ is a carboxy-protecting group selected from methyl, ethyl, t-butyl, benzyl, p-methoxybenzyl, 9-fluorenylmethyl, trimethylsilyl, t-butyldimethylsilyl, and diphenylmethyl; $P^4$ is a hydroxyl-protecting group selected from —$C_{1-6}$ alkyl, tri$C_{1-6}$alkylsilyl, —$C_{1-6}$alkanoyl, benzoyl, benzyl, p-methoxybenzyl, 9-fluorenylmethyl, and diphenylmethyl; and $R^{2a}$, $R^{2b}$, $R^3$, $R^4$, $R^5$, $R^6$, a, b, Z, and X are as defined for formula I. Another intermediate of the invention has formula 10 or a salt thereof:

(10)
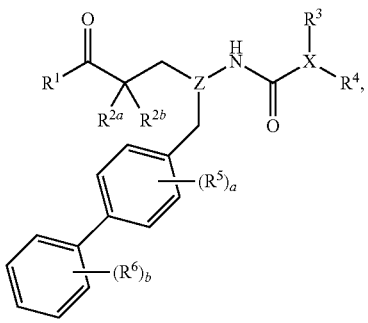

where $R^{3P}$ is selected from —$C_{0-5}$alkylene-O—$P^4$, —$C_{0-1}$alkylene-COO—$P^3$, and phenyl substituted with —O—$P^4$; $P^3$ is a carboxy-protecting group selected from methyl, ethyl, t-butyl, benzyl, p-methoxybenzyl, 9-fluorenylmethyl, trimethylsilyl, t-butyldimethylsilyl, and diphenylmethyl; $P^4$ is a hydroxyl-protecting group selected from —$C_{1-6}$alkyl, tri$C_{1-6}$alkylsilyl, —$C_{1-6}$alkanoyl, benzoyl, benzyl, p-methoxybenzyl, 9-fluorenylmethyl, and diphenylmethyl; and $R^1$, $R^{2a}$, $R^{2b}$, $R^4$, $R^5$, $R^6$, a, b, Z, and X are as defined for formula I. Still another intermediate of the invention has formula 11 or a salt thereof:

(11)
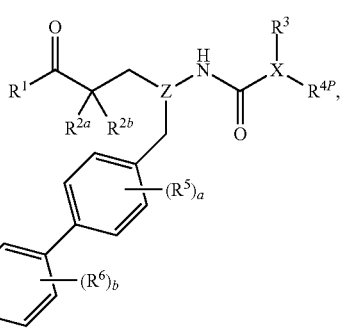

where $R^{4P}$ is selected from —O—$P^4$; —$C_{1-2}$alkylene-COO—$P^3$; and phenyl or benzyl substituted with —COO—$P^3$; $P^3$ is a carboxy-protecting group selected from methyl, ethyl, t-butyl, benzyl, p-methoxybenzyl, 9-fluorenylmethyl, trimethylsilyl, t-butyldimethylsilyl, and diphenylmethyl; $P^4$ is a hydroxyl-protecting group selected from —$C_{1-6}$alkyl, tri$C_{1-6}$alkylsilyl, —$C_{1-6}$alkanoyl, benzoyl, benzyl, p-methoxybenzyl, 9-fluorenylmethyl, and diphenylmethyl; and $R^1$, $R^{2a}$, $R^{2b}$, $R^3$, $R^5$, $R^6$, a, b, Z, and X are as defined for formula I. Yet another intermediate of the invention has formula 12 or a salt thereof:

(12)
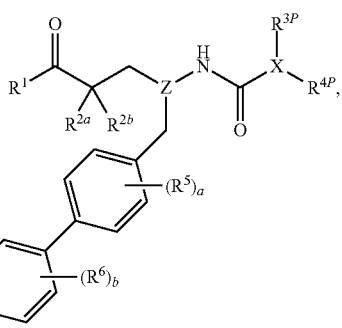

where $R^{3P}$ is selected from —$C_{0-5}$alkylene-O—$P^4$, —$C_{0-1}$alkylene-COO—$P^3$, and phenyl substituted with —O—$P^4$; $R^{4P}$ is selected from —O—$P^4$; —$C_{1-2}$alkylene-COO—$P^3$; and phenyl or benzyl substituted with —COO—$P^3$; $P^3$ is a carboxy-protecting group selected from methyl, ethyl, t-butyl, benzyl, p-methoxybenzyl, 9-fluorenylmethyl, trimethylsilyl, t-butyldimethylsilyl, and diphenylmethyl; $P^4$ is a hydroxyl-protecting group selected from —$C_{1-6}$alkyl, tri$C_{1-6}$alkylsilyl, —$C_{1-6}$alkanoyl, benzoyl, benzyl, p-methoxybenzyl, 9-fluorenylmethyl, and diphenylmethyl; and $R^1$, $R^{2a}$, $R^{2b}$, $R^5$, $R^6$, a, b, Z, and X are as defined for formula I. Thus, another method of preparing compounds of the invention involves deprotecting a compound of formula 1, 9, 10, 11, 12, or a salt thereof.

Further details regarding specific reaction conditions and other procedures for preparing representative compounds of the invention or intermediates thereof are described in the Examples set forth below.

Utility

Compounds of the invention possess neprilysin (NEP) inhibition activity, that is, the compounds are able to inhibit enzyme-catalytic activity. In another embodiment, the compounds do not exhibit significant inhibitory activity of the angiotensin-converting enzyme. One measure of the ability of a compound to inhibit NEP activity is the inhibition constant ($pK_i$). The $pK_i$ value is the negative logarithm to base 10 of the dissociation constant ($K_i$), which is typically reported in molar units. Compounds of the invention of particular interest are those having a $pK_i$ at NEP greater than or equal to 6.0, particularly those having a $pK_i$ greater than or equal to 7.0, and even more particularly those having a $pK_i$ greater than or equal to 8.0. In one embodiment, compounds of interest have a $pK_i$ in the range of 6.0-6.9; in another embodiment, compounds of interest have a $pK_i$ in the range of 7.0-7.9; in yet another embodiment, compounds of interest have a $pK_i$ in the range of 8.0-8.9; and in still another embodiment, compounds of interest have a $pK_i$ in the range of greater than or equal to 9.0. Such values can be determined by techniques that are well known in the art, as well as in the assays described herein.

Another measure of the ability of a compound to inhibit NEP activity is the apparent inhibition constant ($IC_{50}$), which is the molar concentration of compound that results in half-maximal inhibition of substrate conversion by the NEP enzyme. The $pIC_{50}$ value is the negative logarithm to base 10 of the $IC_{50}$. Compounds of the invention that are of particular interest, include those that exhibit a $pIC_{50}$ for NEP greater than or equal to about 5.0. Compounds of interest also include those having a $pIC_{50}$ for NEP ≧ about 6.0 or a $pIC_{50}$ for NEP ≧ about 7.0. In another embodiment, compounds of interest have a $pIC_{50}$ for NEP within the range of about 7.0-10.0.

It is noted that in some cases, compounds of the invention may possess weak NEP inhibition activity. In such cases, those of skill in the art will recognize that these compounds still have utility as research tools.

Exemplary assays to determine properties of compounds of the invention, such as the NEP inhibiting activity, are described in the Examples and include by way of illustration and not limitation, assays that measure NEP inhibition (described in Assay 1). Useful secondary assays include assays to measure ACE inhibition (also described in Assay 1) and aminopeptidase P (APP) inhibition (described in Sulpizio et al. (2005) *JPET* 315:1306-1313). A pharmacodynamic assay to assess the in vivo inhibitory potencies for ACE and NEP in anesthetized rats is described in Assay 2 (see also Seymour et al. (1985) *Hypertension* 7(Suppl I):I-35-I-42 and Wigle et al. (1992) *Can. J. Physiol. Pharmacol.* 70:1525-1528), where ACE inhibition is measured as the percent inhibition of the angiotensin I pressor response and NEP inhibition is measured as increased urinary cyclic guanosine 3',5'-monophosphate (cGMP) output. There are many in vivo assays that can be used to ascertain further utilities of the compounds of the invention. The conscious spontaneously hypertensive rat (SHR) model is a renin dependent hypertension model, and is described in Assay 3. See also Intengan et al. (1999) *Circulation* 100(22):2267-2275 and Badyal et al. (2003) *Indian Journal of Pharmacology* 35:349-362. The conscious desoxycorticosterone acetate-salt (DOCA-salt) rat model is a volume dependent hypertension model that is useful for measuring NEP activity, and is described in Assay 4. See also Trapani et al. (1989) *J. Cardiovasc. Pharmacol.* 14:419-424, Intengan et al. (1999) *Hypertension* 34(4):907-913, and Badyal et al. (2003) supra). The DOCA-salt model is particularly useful for evaluating the ability of a test compound to reduce blood pressure as well as to measure a test compound's ability to prevent or delay a rise in blood pressure. The Dahl salt-sensitive (DSS) hypertensive rat model is a model of hypertension that is sensitive to dietary salt (NaCl), and is described in Assay 5. See also Rapp (1982) *Hypertension* 4:753-763. The rat monocrotaline model of pulmonary arterial hypertension described, for example, in Kato et al. (2008) *J. Cardiovasc. Pharmacol.* 51(1):18-23, is a reliable predictor of clinical efficacy for the treatment of pulmonary arterial hypertension. Heart failure animal models include the DSS rat model for heart failure and the aorto-caval fistula model (AV shunt), the latter of which is described, for example, in Norling et al. (1996) *J. Amer. Soc. Nephrol.* 7:1038-1044. Other animal models, such as the hot plate, tail-flick and formalin tests, can be used to measure the analgesic properties of compounds of the invention, as well as the spinal nerve ligation (SNL) model of neuropathic pain. See, for example, Malmberg et al. (1999) *Current Protocols in Neuroscience* 8.9.1-8.9.15.

Compounds of the invention are expected to inhibit the NEP enzyme in any of the assays listed above, or assays of a similar nature. Thus, the aforementioned assays are useful in determining the therapeutic utility of compounds of the invention, for example, their utility as antihypertensive agents or antidiarrheal agents. Other properties and utilities of compounds of the invention can be demonstrated using other in vitro and in vivo assays well-known to those skilled in the art. Compounds of formula I may be active drugs as well as prodrugs. Thus, when discussing the activity of compounds of the invention, it is understood that any such prodrugs may not exhibit the expected activity in an assay, but are expected to exhibit the desired activity once metabolized.

Compounds of the invention are expected to be useful for the treatment and/or prevention of medical conditions responsive to NEP inhibition. Thus it is expected that patients suffering from a disease or disorder that is treated by inhibiting the NEP enzyme or by increasing the levels of its peptide substrates, can be treated by administering a therapeutically effective amount of a compound of the invention. For example, by inhibiting NEP, the compounds are expected to potentiate the biological effects of endogenous peptides that are metabolized by NEP, such as the natriuretic peptides, bombesin, bradykinins, calcitonin, endothelins, enkephalins, neurotensin, substance P and vasoactive intestinal peptide. Thus, these compounds are expected to have other physiological actions, for example, on the renal, central nervous, reproductive and gastrointestinal systems.

In one embodiment of the invention, patients suffering from a disease or disorder that is treated by inhibiting the NEP enzyme, are treated by administering a compound of the invention that is in its active form, i.e., a compound of formula I where $R^1$ is selected from —$OR^7$ and —$NR^8R^9$, $R^7$ is H, $R^8$ is H or —OH, $R^9$ is H, and $R^{2a}$, $R^{2b}$, $R^3$-$R^6$, a, b, Z, and X are as defined for formula I.

In another embodiment, patients are treated by administering a compound that is metabolized in vitro to form a compound of formula I where $R^1$ is selected from —$OR^7$ and —$NR^8R^9$, $R^7$ is H, $R^8$ is H or —OH, $R^9$ is H, and $R^{2a}$, $R^{2b}$, $R^3$-$R^6$, a, b, Z, and X are as defined for formula I.

In another embodiment, patients are treated by administering a compound of the invention that is in its prodrug form at the $R^1$ group, i.e., a compound of formula I where:

$R^1$ is —$OR^7$; and $R^7$ is selected from —$C_{1-8}$alkyl, —$C_{1-3}$alkylene-$C_{6-10}$aryl, —$C_{1-3}$alkylene-$C_{1-9}$heteroaryl, —$C_{3-7}$cycloalkyl, —$[(CH_2)_2O]_{1-3}CH_3$, —$C_{1-6}$alkylene-$OC(O)R^{10}$, —$C_{1-6}$alkylene-$NR^{12}R^{13}$, —$C_{1-6}$alkylene-$C(O)R^{31}$, —$C_{0-6}$alkylenemorpholinyl, —$C_{1-6}$alkylene-$SO_2$—$C_{1-6}$alkyl,

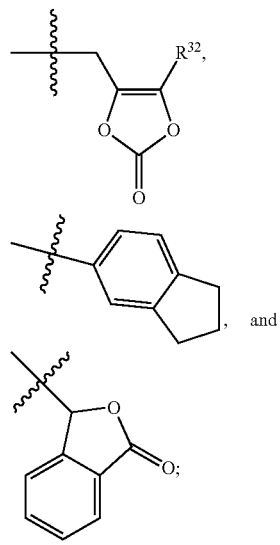

or $R^1$ is —$NR^8R^9$; $R^8$ is selected from —$OC(O)R^{14}$, —$CH_2COOH$, —O-benzyl, pyridyl, and —$OC(S)NR^{15}R^{16}$; and $R^9$ is H; or $R^1$ is —$NR^8R^9$; $R^8$ is selected from —$OC(O)R^{14}$, —$CH_2COOH$, —O-benzyl, pyridyl, and —$OC(S)NR^{15}R^{16}$; and $R^9$ is —$C_{1-6}$alkyl or —$C(O)R^{17}$;

$R^1$ is —$NR^8R^9$; $R^8$ is selected from H or —OH; and $R^9$ is —$C_{1-6}$alkyl or —$C(O)R^{17}$;

$R^1$ is —$OR^7$ and $R^{2a}$ is taken together with $R^7$ to form —$OCR^{18}R^{19}$—; or $R^1$ is —$NR^8R^9$ and $R^{2a}$ is taken together with $R^8$ to form —OC(O)—.

and $R^{2b}$, $R^{10}$, $R^{12}$-$R^{17}$, $R^{31}$, $R^{32}$, $R^3$-$R^6$, a, b, Z, and X are as defined for formula I. In an exemplary embodiment, patients are treated by administering a compound of the invention that is in its prodrug form at the $R^1$ group and has formula III, IV, or V.

Cardiovascular Diseases

By potentiating the effects of vasoactive peptides like the natriuretic peptides and bradykinin, compounds of the invention are expected to find utility in treating and/or preventing medical conditions such as cardiovascular diseases. See, for example, Rogues et al. (1993) Pharmacol. Rev. 45:87-146 and Dempsey et al. (2009) Amer. J. of Pathology 174(3):782-796. Cardiovascular diseases of particular interest include hypertension and heart failure. Hypertension includes, by way of illustration and not limitation: primary hypertension, which is also referred to as essential hypertension or idiopathic hypertension; secondary hypertension; hypertension with accompanying renal disease; severe hypertension with or without accompanying renal disease; pulmonary hypertension, including pulmonary arterial hypertension; and resistant hypertension. Heart failure includes, by way of illustration and not limitation: congestive heart failure; acute heart failure; chronic heart failure, for example with reduced left ventricular ejection fraction (also referred to as systolic heart failure) or with preserved left ventricular ejection fraction (also referred to as diastolic heart failure); and acute and chronic decompensated heart failure. Thus, one embodiment of the invention relates to a method for treating hypertension, particularly primary hypertension or pulmonary arterial hypertension, comprising administering to a patient a therapeutically effective amount of a compound of the invention.

For treatment of primary hypertension, the therapeutically effective amount is typically the amount that is sufficient to lower the patient's blood pressure. This would include both mild-to-moderate hypertension and severe hypertension. When used to treat hypertension, the compound may be administered in combination with other therapeutic agents such as aldosterone antagonists, aldosterone synthase inhibitors, angiotensin-converting enzyme inhibitors and dual-acting angiotensin-converting enzyme/neprilysin inhibitors, angiotensin-converting enzyme 2 (ACE2) activators and stimulators, angiotensin-II vaccines, anti-diabetic agents, anti-lipid agents, anti-thrombotic agents, $AT_1$ receptor antagonists and dual-acting $AT_1$ receptor antagonist/neprilysin inhibitors, $\beta_1$-adrenergic receptor antagonists, dual-acting $\beta$-adrenergic receptor antagonist/$\alpha_1$-receptor antagonists, calcium channel blockers, diuretics, endothelin receptor antagonists, endothelin converting enzyme inhibitors, neprilysin inhibitors, natriuretic peptides and their analogs, natriuretic peptide clearance receptor antagonists, nitric oxide donors, non-steroidal anti-inflammatory agents, phosphodiesterase inhibitors (specifically PDE-V inhibitors), prostaglandin receptor agonists, renin inhibitors, soluble guanylate cyclase stimulators and activators, and combinations thereof. In one particular embodiment of the invention, a compound of the invention is combined with an $AT_1$ receptor antagonist, a calcium channel blocker, a diuretic, or a combination thereof, and used to treat primary hypertension. In another particular embodiment of the invention, a compound of the invention is combined with an $AT_1$ receptor antagonist, and used to treat hypertension with accompanying renal disease. When used to treat resistant hypertension, the compound may be administered in combination with other therapeutic agents such as aldosterone synthase inhibitors.

For treatment of pulmonary arterial hypertension, the therapeutically effective amount is typically the amount that is sufficient to lower the pulmonary vascular resistance. Other goals of therapy are to improve a patient's exercise capacity. For example, in a clinical setting, the therapeutically effective amount can be the amount that improves a patient's ability to walk comfortably for a period of 6 minutes (covering a distance of approximately 20-40 meters). When used to treat pulmonary arterial hypertension the compound may be administered in combination with other therapeutic agents such as α-adrenergic receptor antagonists, $\beta_1$-adrenergic receptor antagonists, $\beta_2$-adrenergic receptor agonists, angiotensin-converting enzyme inhibitors, anticoagulants, calcium channel blockers, diuretics, endothelin receptor antagonists, PDE-V inhibitors, prostaglandin analogs, selective serotonin reuptake inhibitors, and combinations thereof. In one particular embodiment of the invention, a compound of the invention is combined with a PDE-V inhibitor or a selective serotonin reuptake inhibitor and used to treat pulmonary arterial hypertension.

Another embodiment of the invention relates to a method for treating heart failure, in particular congestive heart failure (including both systolic and diastolic congestive heart failure), comprising administering to a patient a therapeutically effective amount of a compound of the invention. Typically, the therapeutically effective amount is the amount that is sufficient to lower blood pressure and/or improve renal functions. In a clinical setting, the therapeutically effective amount can be the amount that is sufficient to improve cardiac hemodynamics, like for instance reduction in wedge pressure, right atrial pressure, filling pressure, and vascular resistance. In one embodiment, the compound is administered as an intravenous dosage form. When used to treat heart failure, the compound may be administered in combination with other therapeutic agents such as adenosine receptor antagonists, advanced glycation end product breakers, aldosterone antagonists, $AT_1$ receptor antagonists, $\beta_1$-adrenergic receptor antagonists, dual-acting β-adrenergic receptor antagonist/$\alpha_1$-receptor antagonists, chymase inhibitors, digoxin, diuretics, endothelin converting enzyme (ECE) inhibitors, endothelin receptor antagonists, natriuretic peptides and their analogs, natriuretic peptide clearance receptor antagonists, nitric oxide donors, prostaglandin analogs, PDE-V inhibitors, soluble guanylate cyclase activators and stimulators, and vasopressin receptor antagonists. In one particular embodiment of the invention, a compound of the invention is combined with an aldosterone antagonist, a $\beta_1$-adrenergic receptor antagonist, an $AT_1$ receptor antagonist, or a diuretic, and used to treat congestive heart failure.

Diarrhea

As NEP inhibitors, compounds of the invention are expected to inhibit the degradation of endogenous enkephalins and thus such compounds may also find utility for the treatment of diarrhea, including infectious and secretory/watery diarrhea. See, for example, Baumer et al. (1992) *Gut* 33:753-758; Farthing (2006) *Digestive Diseases* 24:47-58; and Marçais-Collado (1987) *Eur. J. Pharmacol.* 144(2):125-132. When used to treat diarrhea, compounds of the invention may be combined with one or more additional antidiarrheal agents.

Renal Diseases

By potentiating the effects of vasoactive peptides like the natriuretic peptides and bradykinin, compounds of the invention are expected to enhance renal function (see Chen et al. (1999) *Circulation* 100:2443-2448; Lipkin et al. (1997) *Kidney Int.* 52:792-801; and Dussaule et al. (1993) *Clin. Sci.* 84:31-39) and find utility in treating and/or preventing renal diseases. Renal diseases of particular interest include diabetic nephropathy, chronic kidney disease, proteinuria, and particularly acute kidney injury or acute renal failure (see Sharkovska et al. (2011) *Clin. Lab.* 57:507-515 and Newaz et al. (2010) *Renal Failure* 32:384-390). When used to treat renal disease, the compound may be administered in combination with other therapeutic agents such as angiotensin-converting enzyme inhibitors, $AT_1$ receptor antagonists, and diuretics.

Preventative Therapy

By potentiating the effects of the natriuretic peptides, compounds of the invention are also expected to be useful in preventative therapy, due to the antihypertrophic and antifibrotic effects of the natriuretic peptides (see Potter et al. (2009) *Handbook of Experimental Pharmacology* 191:341-366), for example in preventing the progression of cardiac insufficiency after myocardial infarction, preventing arterial restenosis after angioplasty, preventing thickening of blood vessel walls after vascular operations, preventing atherosclerosis, and preventing diabetic angiopathy.

Glaucoma

By potentiating the effects of the natriuretic peptides, compounds of the invention are expected to be useful to treat glaucoma. See, for example, Diestelhorst et al. (1989) *International Ophthalmology* 12:99-101. When used to treat glaucoma, compounds of the invention may be combined with one or more additional antiglaucoma agents.

Pain Relief

As NEP inhibitors, compounds of the invention are expected to inhibit the degradation of endogenous enkephalins and thus such compounds may also find utility as analgesics. See, for example, Rogues et al. (1980) *Nature* 288:286-288 and Thanawala et al. (2008) *Current Drug Targets* 9:887-894. When used to treat pain, the compounds of the invention may be combined with one or more additional antinociceptive drugs such as aminopeptidase N or dipeptidyl peptidase III inhibitors, non-steroidal anti-inflammatory agents, monoamine reuptake inhibitors, muscle relaxants, NMDA receptor antagonists, opioid receptor agonists, $5\text{-HT}_{1D}$ serotonin receptor agonists, and tricyclic antidepressants.

Other Utilities

Due to their NEP inhibition properties, compounds of the invention are also expected to be useful as antitussive agents, as well as find utility in the treatment of portal hypertension associated with liver cirrhosis (see Sansoe et al. (2005) *J. Hepatol.* 43:791-798), cancer (see Vesely (2005) *J. Investigative Med.* 53:360-365), depression (see Noble et al. (2007) *Exp. Opin. Ther. Targets* 11:145-159), menstrual disorders, preterm labor, pre-eclampsia, endometriosis, reproductive disorders (for example, male and female infertility, polycystic ovarian syndrome, implantation failure), and male and female sexual dysfunction, including male erectile dysfunction and female sexual arousal disorder. More specifically, the compounds of the invention are expected to be useful in treating female sexual dysfunction (see Pryde et al. (2006) *J. Med. Chem.* 49:4409-4424), which is often defined as a female patient's difficulty or inability to find satisfaction in sexual expression. This covers a variety of diverse female sexual disorders including, by way of illustration and not limitation, hypoactive sexual desire disorder, sexual arousal disorder, orgasmic disorder and sexual pain disorder. When used to treat such disorders, especially female sexual dysfunction, compounds of the invention may be combined with one or more of the following secondary agents: PDE-V inhibitors, dopamine agonists, estrogen receptor agonists and/or antagonists, androgens, and estrogens. Due to their NEP inhibition properties, compounds of the invention are also expected to have anti-inflammatory properties, and are expected to have utility as such, particularly when used in combination with statins.

Recent studies suggest that NEP plays a role in regulating nerve function in insulin-deficient diabetes and diet induced obesity. Coppey et al. (2011) *Neuropharmacology* 60:259-266. Therefore, due to their NEP inhibition properties, compounds of the invention are also expected to be useful in providing protection from nerve impairment caused by diabetes or diet induced obesity.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

Research Tools

Since compounds of the invention possess NEP enzyme inhibition activity, such compounds are also useful as research tools for investigating or studying biological systems or samples having a NEP enzyme, for example to study diseases where the NEP enzyme or its peptide substrates plays a role. Any suitable biological system or sample having a NEP enzyme may be employed in such studies which may be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest. In one particular embodiment of the invention, NEP enzyme activity in a mammal is inhibited by administering a NEP-inhibiting amount of a compound of the invention. Compounds of the invention can also be used as research tools by conducting biological assays using such compounds.

When used as a research tool, a biological system or sample comprising a NEP enzyme is typically contacted with a NEP enzyme-inhibiting amount of a compound of the invention. After the biological system or sample is exposed to the compound, the effects of inhibiting the NEP enzyme are determined using conventional procedures and equipment, such as by measuring receptor binding in a binding assay or measuring ligand-mediated changes in a functional assay. Exposure encompasses contacting cells or tissue with the compound, administering the compound to a mammal, for example by i.p., p.o, i.v., s.c., or inhaled administration, and so forth. This determining step can involve measuring a response (a quantitative analysis) or can involve making an observation (a qualitative analysis). Measuring a response involves, for example, determining the effects of the compound on the biological system or sample using conventional procedures and equipment, such as enzyme activity assays and measuring enzyme substrate or product mediated changes in functional assays. The assay results can be used to determine the activity level as well as the amount of compound necessary to achieve the desired result, that is, a NEP enzyme-inhibiting amount. Typically, the determining step will involve determining the effects of inhibiting the NEP enzyme.

Additionally, compounds of the invention can be used as research tools for evaluating other chemical compounds, and thus are also useful in screening assays to discover, for example, new compounds having NEP-inhibiting activity. In this manner, a compound of the invention is used as a standard in an assay to allow comparison of the results obtained with a test compound and with compounds of the invention to identify those test compounds that have about equal or superior activity, if any. For example, $pK_i$ data for a test compound or a group of test compounds is compared to the $pK_i$ data for a compound of the invention to identify those test compounds that have the desired properties, for example, test compounds having a $pK_i$ value about equal or superior to a compound of the invention, if any. This aspect of the invention includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include a NEP enzyme inhibition assay.

Pharmaceutical Compositions and Formulations

Compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compounds of the invention may be administered, for example orally, in multiple doses per day (for example, two, three, or four times daily), in a single daily dose or a single weekly dose. It will be understood that any form of the compounds of the invention, (that is, free base, free acid, pharmaceutically acceptable salt, solvate, etc.) that is suitable for the particular mode of administration can be used in the pharmaceutical compositions discussed herein.

Accordingly, in one embodiment, the invention relates to a pharmaceutical composition comprising a pharmaceutically acceptable carrier and a compound of the invention. The compositions may contain other therapeutic and/or formulating agents if desired. When discussing compositions, the "compound of the invention" may also be referred to herein as the "active agent," to distinguish it from other components of the formulation, such as the carrier. Thus, it is understood that the term "active agent" includes compounds of formula I as well as pharmaceutically acceptable salts, solvates and prodrugs of that compound.

The pharmaceutical compositions of the invention typically contain a therapeutically effective amount of a compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

In one embodiment, the pharmaceutical compositions are suitable for oral administration. Suitable compositions for oral administration may be in the form of capsules, tablets, pills, lozenges, cachets, dragees, powders, granules; solutions or suspensions in an aqueous or non-aqueous liquid; oil-in-water or water-in-oil liquid emulsions; elixirs or syrups; and the like; each containing a predetermined amount of the active agent.

When intended for oral administration in a solid dosage form (capsules, tablets, pills and the like), the composition will typically comprise the active agent and one or more pharmaceutically acceptable carriers, such as sodium citrate or dicalcium phosphate. Solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants may also be present in the pharmaceutical compositions. Exemplary coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like. Examples of pharmaceutically acceptable antioxidants include: water-soluble antioxidants, such as ascorbic acid, cysteine hydrochloride, sodium bisulfate, sodium metabisulfate sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like.

Compositions may also be formulated to provide slow or controlled release of the active agent using, by way of example, hydroxypropyl methyl cellulose in varying proportions or other polymer matrices, liposomes and/or microspheres. In addition, the pharmaceutical compositions of the invention may contain opacifying agents and may be formulated so that they release the active agent only, or preferentially, in a certain portion of the gastrointestinal tract, optionally, in a delayed manner. Examples of embedding compositions which can be used include polymeric substances and waxes. The active agent can also be in microencapsulated form, optionally with one or more of the above-described excipients.

Suitable liquid dosage forms for oral administration include, by way of illustration, pharmaceutically acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (for example, cottonseed, groundnut, corn, germ, olive, castor and sesame oils), glycerol, tetrahydrofuryl alcohol, polyethylene glycols and fatty acid esters of sorbitan, and mixtures thereof. Suspensions may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical compositions of the invention may be packaged in a unit dosage form. The term "unit dosage form" refers to a physically discrete unit suitable for dosing a patient, that is, each unit containing a predetermined quantity of the active agent calculated to produce the desired therapeutic effect either alone or in combination with one or more additional units. For example, such unit dosage forms may be capsules, tablets, pills, and the like.

In another embodiment, the compositions of the invention are suitable for inhaled administration, and will typically be in the form of an aerosol or a powder. Such compositions are generally administered using well-known delivery devices, such as a nebulizer, dry powder, or metered-dose inhaler. Nebulizer devices produce a stream of high velocity air that causes the composition to spray as a mist that is carried into a patient's respiratory tract. An exemplary nebulizer formulation comprises the active agent dissolved in a carrier to form a solution, or micronized and combined with a carrier to form a suspension of micronized particles of respirable size. Dry powder inhalers administer the active agent as a free-flowing powder that is dispersed in a patient's air-stream during inspiration. An exemplary dry powder formulation comprises the active agent dry-blended with an excipient such as lactose, starch, mannitol, dextrose, polylactic acid, polylactide-co-glycolide, and combinations thereof. Metered-dose inhalers discharge a measured amount of the active agent using compressed propellant gas. An exemplary metered-dose formulation comprises a solution or suspension of the active agent in a liquefied propellant, such as a chlorofluorocarbon or hydrofluoroalkane. Optional components of such formulations include co-solvents, such as ethanol or pentane, and surfactants, such as sorbitan trioleate, oleic acid, lecithin, glycerin, and sodium lauryl sulfate. Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. Alternatively, a suspension formulation can be prepared by spray drying a coating of surfactant on micronized particles of the active agent. The formulation is then loaded into an aerosol canister, which forms a portion of the inhaler.

Compounds of the invention can also be administered parenterally (for example, by subcutaneous, intravenous, intramuscular, or intraperitoneal injection). For such administration, the active agent is provided in a sterile solution, suspension, or emulsion. Exemplary solvents for preparing such formulations include water, saline, low molecular weight alcohols such as propylene glycol, polyethylene glycol, oils, gelatin, fatty acid esters such as ethyl oleate, and the like. Parenteral formulations may also contain one or more anti-oxidants, solubilizers, stabilizers, preservatives, wetting agents, emulsifiers, and dispersing agents. Surfactants, additional stabilizing agents or pH-adjusting agents (acids, bases or buffers) and anti-oxidants are particularly useful to provide stability to the formulation, for example, to minimize or avoid hydrolysis of ester and amide linkages that may be present in the compound. These formulations may be rendered sterile by use of a sterile injectable medium, a sterilizing agent, filtration, irradiation, or heat. In one particular embodiment, the parenteral formulation comprises an aqueous cyclodextrin solution as the pharmaceutically acceptable carrier. Suitable cyclodextrins include cyclic molecules containing six or more α-D-glucopyranose units linked at the 1,4 positions by α linkages as in amylase, β-cyclodextrin or cycloheptaamylose. Exemplary cyclodextrins include cyclodextrin derivatives such as hydroxypropyl and sulfobutyl ether cyclodextrins such as hydroxypropyl-β-cyclodextrin and sulfobutyl ether β-cyclodextrin. Exemplary buffers for such formulations include carboxylic acid-based buffers such as citrate, lactate and maleate buffer solutions.

Compounds of the invention can also be administered transdermally using known transdermal delivery systems and excipients. For example, the compound can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Secondary Agents

The compounds of the invention may be useful as the sole treatment of a disease or may be combined with one or more additional therapeutic agents in order to obtain the desired therapeutic effect. Thus, in one embodiment, pharmaceutical compositions of the invention contain other drugs that are co-administered with a compound of the invention. For example, the composition may further comprise one or more drugs (also referred to as "secondary agents(s)"). Such therapeutic agents are well known in the art, and include adenosine receptor antagonists, α-adrenergic receptor antagonists, $\beta_1$-adrenergic receptor antagonists, $\beta_2$-adrenergic receptor agonists, dual-acting β-adrenergic receptor antagonist/$\alpha_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof. Specific examples of these agents are detailed herein.

Accordingly, in yet another aspect of the invention, a pharmaceutical composition comprises a compound of the invention, a second active agent, and a pharmaceutically acceptable carrier. Third, fourth etc. active agents may also be included in the composition. In combination therapy, the amount of compound of the invention that is administered, as well as the amount of secondary agents, may be less than the amount typically administered in monotherapy.

Compounds of the invention may be physically mixed with the second active agent to form a composition containing both agents; or each agent may be present in separate and distinct compositions which are administered to the patient simultaneously or at separate times. For example, a compound of the invention can be combined with a second active agent using conventional procedures and equipment to form a combination of active agents comprising a compound of the invention and a second active agent. Additionally, the active agents may be combined with a pharmaceutically acceptable carrier to form a pharmaceutical composition comprising a compound of the invention, a second active agent and a pharmaceutically acceptable carrier. In this embodiment, the components of the composition are typically mixed or blended to create a physical mixture. The physical mixture is then administered in a therapeutically effective amount using any of the routes described herein.

Alternatively, the active agents may remain separate and distinct before administration to the patient. In this embodiment, the agents are not physically mixed together before administration but are administered simultaneously or at separate times as separate compositions. Such compositions can be packaged separately or may be packaged together in a kit. When administered at separate times, the secondary agent will typically be administered less than 24 hours after administration of the compound of the invention, ranging anywhere from concurrent with administration of the compound of the invention to about 24 hours post-dose. This is also referred to as sequential administration. Thus, a compound of the invention can be orally administered simultaneously or sequentially with another active agent using two tablets, with one tablet for each active agent, where sequential may mean being administered immediately after administration of the compound of the invention or at some predetermined time later (for example, one hour later or three hours later). It is also contemplated that the secondary agent may be administered more than 24 hours after administration of the compound of the invention. Alternatively, the combination may be administered by different routes of administration, that is, one orally and the other by inhalation.

In one embodiment, the kit comprises a first dosage form comprising a compound of the invention and at least one additional dosage form comprising one or more of the secondary agents set forth herein, in quantities sufficient to carry out the methods of the invention. The first dosage form and the second (or third, etc.) dosage form together comprise a therapeutically effective amount of active agents for the treatment or prevention of a disease or medical condition in a patient.

Secondary agent(s), when included, are present in a therapeutically effective amount such that they are typically administered in an amount that produces a therapeutically beneficial effect when co-administered with a compound of the invention. The secondary agent can be in the form of a pharmaceutically acceptable salt, solvate, optically pure stereoisomer, and so forth. The secondary agent may also be in the form of a prodrug, for example, a compound having a carboxylic acid group that has been esterified. Thus, secondary agents listed herein are intended to include all such forms, and are commercially available or can be prepared using conventional procedures and reagents.

In one embodiment, compounds of the invention are administered in combination with an adenosine receptor antagonist, representative examples of which include, but are not limited to, naxifylline, rolofylline, SLV-320, theophylline, and tonapofylline.

In one embodiment, compounds of the invention are administered in combination with an α-adrenergic receptor antagonist, representative examples of which include, but are not limited to, doxazosin, prazosin, tamsulosin, and terazosin.

Compounds of the invention may also be administered in combination with a $β_1$-adrenergic receptor antagonist ("$β_1$-blockers"). Representative $β_1$-blockers include, but are not limited to, acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, bubridine, butofilolol, carazolol, carteolol, carvedilol, celiprolol, cetamolol, cloranolol, dilevalol, epanolol, esmolol, indenolol, labetolol, levobunolol, mepindolol, metipranolol, metoprolol such as metoprolol succinate and metoprolol tartrate, moprolol, nadolol, nadoxolol, nebivalol, nipradilol, oxprenolol, penbutolol, perbutolol, pindolol, practolol, pronethalol, propranolol, sotalol, sufinalol, talindol, tertatolol, tilisolol, timolol, toliprolol, xibenolol, and combinations thereof. In one particular embodiment, the $β_1$-antagonist is selected from atenolol, bisoprolol, metoprolol, propranolol, sotalol, and combinations thereof. Typically, the $β_1$-blocker will be administered in an amount sufficient to provide from about 2-900 mg per dose.

In one embodiment, compounds of the invention are administered in combination with a $β_2$-adrenergic receptor agonist, representative examples of which include, but are not limited to, albuterol, bitolterol, fenoterol, formoterol, indacaterol, isoetharine, levalbuterol, metaproterenol, pirbuterol, salbutamol, salmefamol, salmeterol, terbutaline, vilanterol, and the like Typically, the $β_2$-adrenergic receptor agonist will be administered in an amount sufficient to provide from about 0.05-500 μg per dose.

In one embodiment, compounds of the invention are administered in combination with an advanced glycation end product (AGE) breaker, examples of which include, by way of illustration and not limitation, alagebrium (or ALT-711), and TRC4149.

In another embodiment, compounds of the invention are administered in combination with an aldosterone antagonist, representative examples of which include, but are not limited to, eplerenone, spironolactone, and combinations thereof. Typically, the aldosterone antagonist will be administered in an amount sufficient to provide from about 5-300 mg per day.

In one embodiment, compounds of the invention are administered in combination with an aminopeptidase N or dipeptidyl peptidase III inhibitor, examples of which include, by way of illustration and not limitation, bestatin and PC18 (2-amino-4-methylsulfonyl butane thiol, methionine thiol).

Compounds of the invention can also be administered in combination with an angiotensin-converting enzyme (ACE) inhibitor. Representative ACE inhibitors include, but are not limited to, accupril, alacepril, benazepril, benazeprilat, captopril, ceranapril, cilazapril, delapril, enalapril, enalaprilat, fosinopril, fosinoprilat, imidapril, lisinopril, moexipril, monopril, moveltopril, pentopril, perindopril, quinapril, quinaprilat, ramipril, ramiprilat, saralasin acetate, spirapril, temocapril, trandolapril, zofenopril, and combinations thereof.

In a particular embodiment, the ACE inhibitor is selected from: benazepril, captopril, enalapril, lisinopril, ramipril, and combinations thereof. Typically, the ACE inhibitor will be administered in an amount sufficient to provide from about 1-150 mg per day. In another embodiment, compounds of the invention are administered in combination with a dual-acting angiotensin-converting enzyme/neprilysin (ACE/NEP) inhibitor, examples of which include, but are not limited to:

AVE-0848 ((4S,7S,12bR)-7-[3-methyl-2(S)-sulfanylbutyramido]-6-oxo-1,2,3,4,6,7,8,12b-octahydropyrido[2,1-a][2]-benzazepine-4-carboxylic acid); AVE-7688 (ilepatril) and its parent compound; BMS-182657 (2-[2-oxo-3(S)-[3-phenyl-2 (S)-sulfanylpropionamido]-2,3,4,5-tetrahydro-1H-1-benzazepin-1-yl]acetic acid); CGS-35601 (N-[1-[4-methyl-2(S)-sulfanylpentanamido]cyclopentylcarbonyl]-L-tryptophan); fasidotril; fasidotrilate; enalaprilat; ER-32935 ((3R,6S,9aR)-6-[3(S)-methyl-2(S)-sulfanylpentanamido]-5-oxoperhydrothiazolo[3,2-a]azepine-3-carboxylic acid); gempatrilat; MDL-101264 ((4S,7S,12bR)-7-[2(S)-(2-morpholinoacetylthio)-3-phenylpropionamido]-6-oxo-1,2,3,4,6,7,8, 12b-octahydropyrido[2,1-a][2]benzazepine-4-carboxylic acid); MDL-101287 ([4S-[4α,7α(R*),12bβ]]-7-[2-(carboxymethyl)-3-phenylpropionamido]-6-oxo-1,2,3,4,6,7,8, 12b-octahydropyrido[2,1-a][2]benzazepine-4-carboxylic acid); omapatrilat; RB-105 (N-[2(S)-(mercaptomethyl)-3 (R)-phenylbutyl]-L-alanine); sampatrilat; SA-898 ((2R, 4R)—N-[2-(2-hydroxyphenyl)-3-(3-mercaptopropionyl) thiazolidin-4-ylcarbonyl]-L-phenylalanine); Sch-50690 (N-[1(S)-carboxy-2-[N2-(methanesulfonyl)-L-lysylamino] ethyl]-L-valyl-L-tyrosine); and combinations thereof, may also be included. In one particular embodiment, the ACE/NEP inhibitor is selected from: AVE-7688, enalaprilat, fasidotril, fasidotrilate, omapatrilat, sampatrilat, and combinations thereof.

In one embodiment, compounds of the invention are administered in combination with an angiotensin-converting enzyme 2 (ACE2) activator or stimulator.

In one embodiment, compounds of the invention are administered in combination with an angiotensin-II vaccine, examples of which include, but are not limited to ATR12181 and CYT006-AngQb.

In one embodiment, compounds of the invention are administered in combination with an anticoagulant, representative examples of which include, but are not limited to: coumarins such as warfarin; heparin; and direct thrombin inhibitors such as argatroban, bivalirudin, dabigatran, and lepirudin.

In yet another embodiment, compounds of the invention are administered in combination with an anti-diabetic agent. Representative anti-diabetic agents include injectable drugs as well as orally effective drugs, and combinations thereof. Examples of injectable drugs include, but are not limited to, insulin and insulin derivatives. Examples of orally effective drugs include, but are not limited to: biguanides such as metformin; glucagon antagonists; α-glucosidase inhibitors such as acarbose and miglitol; dipeptidyl peptidase IV inhibitors (DPP-IV inhibitors) such as alogliptin, denagliptin, linagliptin, saxagliptin, sitagliptin, and vildagliptin; meglitinides such as repaglinide; oxadiazolidinediones; sulfonylureas such as chlorpropamide, glimepiride, glipizide, glyburide, and tolazamide; thiazolidinediones such as pioglitazone and rosiglitazone; and combinations thereof.

In another embodiment, compounds of the invention are administered in combination with antidiarrheal treatments. Representative treatment options include, but are not limited to, oral rehydration solutions (ORS), loperamide, diphenoxylate, and bismuth sabsalicylate.

In yet another embodiment, a compound of the invention is administered in combination with an anti-glaucoma agent. Representative anti-glaucoma agents include, but are not limited to: α-adrenergic agonists such as brimonidine; β₁-adrenergic receptor antagonists; topical β₁-blockers such as betaxolol, levobunolol, and timolol; carbonic anhydrase inhibitors such as acetazolamide, brinzolamide, or dorzolamide; cholinergic agonists such as cevimeline and DMXB-anabaseine; epinephrine compounds; miotics such as pilocarpine; and prostaglandin analogs.

In yet another embodiment, compounds of the invention are administered in combination with an anti-lipid agent. Representative anti-lipid agents include, but are not limited to: cholesteryl ester transfer protein inhibitors (CETPs) such as anacetrapib, dalcetrapib, and torcetrapib; statins such as atorvastatin, fluvastatin, lovastatin, pravastatin, rosuvastatin and simvastatin; and combinations thereof.

In one embodiment, compounds of the invention are administered in combination with an anti-thrombotic agent. Representative anti-thrombotic agents include, but are not limited to: aspirin; anti-platelet agents such as clopidogrel, prasugrel, and ticlopidine; heparin, and combinations thereof.

In one embodiment, compounds of the invention are administered in combination with an $AT_1$ receptor antagonist, also known as angiotensin II type 1 receptor blockers (ARBs). Representative ARBs include, but are not limited to, abitesartan, azilsartan (e.g., azilsartan medoxomil), benzyllosartan, candesartan, candesartan cilexetil, elisartan, embusartan, enoltasosartan, eprosartan, EXP3174, fonsartan, forasartan, glycyllosartan, irbesartan, isoteoline, losartan, medoximil, milfasartan, olmesartan (e.g., olmesartan medoxomil), opomisartan, pratosartan, ripisartan, saprisartan, saralasin, sarmesin, TAK-591, tasosartan, telmisartan, valsartan, zolasartan, and combinations thereof. In a particular embodiment, the ARB is selected from azilsartan medoxomil, candesartan cilexetil, eprosartan, irbesartan, losartan, olmesartan medoxomil, irbesartan, saprisartan, tasosartan, telmisartan, valsartan, and combinations thereof. Exemplary salts and/or prodrugs include candesartan cilexetil, eprosartan mesylate, losartan potassium salt, and olmesartan medoxomil. Typically, the ARB will be administered in an amount sufficient to provide from about 4-600 mg per dose, with exemplary daily dosages ranging from 20-320 mg per day.

Compounds of the invention may also be administered in combination with a dual-acting agent, such as an $AT_1$ receptor antagonist/neprilysin inhibitor (ARB/NEP) inhibitor, examples of which include, but are not limited to, compounds described in U.S. Publication Nos. 2008/0269305 and 2009/0023228, both to Allegretti et al. filed on Apr. 23, 2008, such as the compound, 4'-{2-ethoxy-4-ethyl-5-[((S)-2-mercapto-4-methylpentanoylamino)-methyl]imidazol-1-ylmethyl}-3'-fluorobiphenyl-2-carboxylic acid.

Compounds of the invention may also be administered in combination with multifunctional angiotensin receptor blockers as described in Kurtz & Klein (2009) *Hypertension Research* 32:826-834.

In one embodiment, compounds of the invention are administered in combination with a bradykinin receptor antagonist, for example, icatibant (HOE-140). It is expected that this combination therapy may present the advantage of preventing angioedema or other unwanted consequences of elevated bradykinin levels.

In one embodiment, compounds of the invention are administered in combination with a calcium channel blocker. Representative calcium channel blockers include, but are not limited to, amlodipine, anipamil, aranipine, barnidipine, bencyclane, benidipine, bepridil, clentiazem, cilnidipine, cinnarizine, diltiazem, efonidipine, elgodipine, etafenone, felodipine, fendiline, flunarizine, gallopamil, isradipine, lacidipine, lercanidipine, lidoflazine, lomerizine, manidipine, mibefradil, nicardipine, nifedipine, niguldipine, nilidipine, nilvadipine, nimodipine, nisoldipine, nitrendipine, nivaldipine, perhexyline, prenylamine, ryosidine, semotiadil, terodiline, tiapamil, verapamil, and combinations thereof. In a particular embodiment, the calcium channel blocker is selected from amlodipine, bepridil, diltiazem, felodipine, isradipine, lacidipine, nicardipine, nifedipine, niguldipine, niludipine, nimodipine, nisoldipine, ryosidine, verapamil, and combinations thereof. Typically, the calcium channel blocker will be administered in an amount sufficient to provide from about 2-500 mg per dose.

In one embodiment, compounds of the invention are administered in combination with a chymase inhibitor, such as TPC-806 and 2-(5-formylamino-6-oxo-2-phenyl-1,6-dihydropyrimidine-1-yl)-N-[{3,4-dioxo-1-phenyl-7-(2-pyridyloxy)}-2-heptyl]acetamide (NK3201).

In one embodiment, compounds of the invention are administered in combination with a diuretic. Representative diuretics include, but are not limited to: carbonic anhydrase inhibitors such as acetazolamide and dichlorphenamide; loop diuretics, which include sulfonamide derivatives such as acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torsemide, tripamide, and xipamide, as well as non-sulfonamide diuretics such as ethacrynic acid and other phenoxyacetic acid compounds such as tienilic acid, indacrinone and quincarbate; osmotic diuretics such as mannitol; potassium-sparing diuretics, which include aldosterone antagonists such as spironolactone, and $Na^+$ channel inhibitors such as amiloride and triamterene; thiazide and thiazide-like diuretics such as althiazide, bendroflumethiazide, benzylhydrochlorothiazide, benzthiazide, buthiazide, chlorthalidone, chlorothiazide, cyclopenthiazide, cyclothiazide, epithiazide, ethiazide, fenquizone, flumethiazide, hydrochlorothiazide, hydroflumethiazide, indapamide, methylclothiazide, meticrane, metolazone, paraflutizide, polythiazide, quinethazone, teclothiazide, and trichloromethiazide; and combinations thereof. In a particular embodiment, the diuretic is selected from amiloride, bumetanide, chlorothiazide, chlorthalidone, dichlorphenamide, ethacrynic acid, furosemide, hydrochlorothiazide, hydroflumethiazide, indapamide, methylclothiazide, metolazone, torsemide, triamterene, and combinations thereof. The diuretic will be administered in an amount sufficient to provide from about 5-50 mg per day, more typically 6-25 mg per day, with common dosages being 6.25 mg, 12.5 mg or 25 mg per day.

Compounds of the invention may also be administered in combination with an endothelin converting enzyme (ECE) inhibitor, examples of which include, but are not limited to, phosphoramidon, CGS 26303, and combinations thereof.

In a particular embodiment, compounds of the invention are administered in combination with an endothelin receptor antagonist. Representative endothelin receptor antagonists include, but are not limited to: selective endothelin receptor antagonists that affect endothelin A receptors, such as avosentan, ambrisentan, atrasentan, BQ-123, clazosentan, darusentan, sitaxentan, and zibotentan; and dual endothelin receptor antagonists that affect both endothelin A and B receptors, such as bosentan, macitentan, tezosentan).

In yet another embodiment, a compound of the invention is administered in combination with one or more HMG-CoA reductase inhibitors, which are also known as statins. Representative statins include, but are not limited to, atorvastatin, fluvastatin, lovastatin, pitavastatin, pravastatin, rosuvastatin and simvastatin.

In one embodiment, compounds of the invention are administered in combination with a monoamine reuptake inhibitor, examples of which include, by way of illustration and not limitation, norepinephrine reuptake inhibitors such as atomoxetine, buprorion and the buprorion metabolite hydroxybuproprion, maprotiline, reboxetine, and viloxazine; selective serotonin reuptake inhibitors (SSRIs) such as citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline; dual serotonin-norepinephrine reuptake inhibitors (SNRIs) such as bicifadine, duloxetine, milnacipran, nefazodone, and venlafaxine; and combinations thereof.

In another embodiment, compounds of the invention are administered in combination with a muscle relaxant, examples of which include, but are not limited to: carisoprodol, chlorzoxazone, cyclobenzaprine, diflunisal, metaxalone, methocarbamol, and combinations thereof.

In one embodiment, compounds of the invention are administered in combination with a natriuretic peptide or analog, examples of which include but are not limited to: carperitide, CD-NP (Nile Therapeutics), CU-NP, nesiritide, PL-3994 (Palatin Technologies, Inc.), ularitide, cenderitide, and compounds described in Ogawa et al (2004) *J. Biol. Chem.* 279:28625-31. These compounds are also referred to as natriuretic peptide receptor-A (NPR-A) agonists. In another embodiment, compounds of the invention are administered in combination with a natriuretic peptide clearance receptor (NPR-C) antagonist such as SC-46542, cANF (4-23), and AP-811 (Veale (2000) *Bioorg Med Chem Lett* 10:1949-52). For example, AP-811 has shown synergy when combined with the NEP inhibitor, thiorphan (Wegner (1995) *Clin. Exper. Hypert.* 17:861-876).

In another embodiment, compounds of the invention are administered in combination with a neprilysin (NEP) inhibitor. Representative NEP inhibitors include, but are not limited to: AHU-377; candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido]propionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl) propionic acid derivatives described in WO 2006/027680 to Hepworth et al. (Pfizer Inc.); JMV-390-1(2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl) propionamide); SCH-32615 ((S)—N—[N-(1-carboxy-2-phenylethyl)-L-phenylalanyl]-β-alanine) and its prodrug SCH-34826 ((S)—N—[N-[1-[[(2,2-dimethyl-1,3-dioxolan-4-yl)methoxy]carbonyl]-2-phenylethyl]-L-phenylalanyl]-β-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-β-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl] carbonyl]amino]cyclohexanecarboxylic acid); UK-447,841 (2-{1-[3-(4-chlorophenyl)propylcarbamoyl]-cyclopentylmethyl}-4-methoxybutyric acid); UK-505,749 ((R)-2-methyl-3-{1-[3-(2-methylbenzothiazol-6-yl)propylcarbamoyl] cyclopentyl}propionic acid); 5-biphenyl-4-yl-4-(3-carboxypropionylamino)-2-methylpentanoic acid and 5-biphenyl-4-yl-4-(3-carboxypropionylamino)-2-methyl-pentanoic acid ethyl ester (WO 2007/056546); daglutril [(3S, 2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708 to Khder et al. (Novartis AG); and combinations thereof. In a particular embodiment, the NEP inhibitor is selected from AHU-377, candoxatril, candoxatrilat, CGS-24128, phosphoramidon, SCH-32615, SCH-34826, SQ-28603, thiorphan, and combinations thereof. In a particular embodiment, the NEP inhibitor is a compound such as daglutril or CGS-26303 ([N-[2-(biphenyl-4-yl)-1(S)-(1H-tetrazol-5-yl)ethyl]amino]methylphosphonic acid), which have activity both as inhibitors of the endothelin converting enzyme (ECE) and of NEP. Other dual acting ECE/NEP compounds can also be used. The NEP inhibitor will be administered in an amount sufficient to provide from about 20-800 mg per day, with typical daily dosages ranging from 50-700 mg per day, more commonly 100-600 or 100-300 mg per day.

In one embodiment, compounds of the invention are administered in combination with a nitric oxide donor, examples of which include, but are not limited to nicorandil; organic nitrates such as pentaerythritol tetranitrate; and sydnonimines such as linsidomine and molsidomine.

In yet another embodiment, compounds of the invention are administered in combination with a non-steroidal anti-inflammatory agent (NSAID). Representative NSAIDs include, but are not limited to: acemetacin, acetyl salicylic acid, alclofenac, alminoprofen, amfenac, amiprilose, amoxiprin, anirolac, apazone, azapropazone, benorilate, benoxaprofen, bezpiperylon, broperamole, bucloxic acid, carprofen, clidanac, diclofenac, diflunisal, diftalone, enolicam, etodolac, etoricoxib, fenbufen, fenclofenac, fenclozic acid, fenoprofen, fentiazac, feprazone, flufenamic acid, flufenisal, fluprofen, flurbiprofen, furofenac, ibufenac, ibuprofen, indomethacin, indoprofen, isoxepac, isoxicam, ketoprofen, ketorolac, lofemizole, lornoxicam, meclofenamate, meclofenamic acid, mefenamic acid, meloxicam, mesalamine, miroprofen, mofebutazone, nabumetone, naproxen, niflumic acid, oxaprozin, oxpinac, oxyphenbutazone, phenylbutazone, piroxicam, pirprofen, pranoprofen, salsalate, sudoxicam, sulfasalazine, sulindac, suprofen, tenoxicam, tiopinac, tiaprofenic acid, tioxaprofen, tolfenamic acid, tolmetin, triflumidate, zidometacin, zomepirac, and combinations thereof. In a particular embodiment, the NSAID is selected from etodolac, flurbiprofen, ibuprofen, indomethacin, ketoprofen, ketorolac, meloxicam, naproxen, oxaprozin, piroxicam, and combinations thereof.

In one embodiment, compounds of the invention are administered in combination with an N-methyl d-aspartate (NMDA) receptor antagonist, examples of which include, by way of illustration and not limitation, including amantadine, dextromethorphan, dextropropoxyphene, ketamine, ketobemidone, memantine, methadone, and so forth.

In still another embodiment, compounds of the invention are administered in combination with an opioid receptor agonist (also referred to as opioid analgesics). Representative opioid receptor agonists include, but are not limited to: buprenorphine, butorphanol, codeine, dihydrocodeine, fentanyl, hydrocodone, hydromorphone, levallorphan, levorphanol, meperidine, methadone, morphine, nalbuphine, nalmefene, nalorphine, naloxone, naltrexone, nalorphine, oxycodone, oxymorphone, pentazocine, propoxyphene, tramadol, and combinations thereof. In certain embodiments, the opioid receptor agonist is selected from codeine, dihydrocodeine, hydrocodone, hydromorphone, morphine, oxycodone, oxymorphone, tramadol, and combinations thereof.

In a particular embodiment, compounds of the invention are administered in combination with a phosphodiesterase (PDE) inhibitor, particularly a PDE-V inhibitor. Representative PDE-V inhibitors include, but are not limited to, avanafil, lodenafil, mirodenafil, sildenafil (Revatio®), tadalafil (Adcirca®), vardenafil (Levitra®), and udenafil.

In another embodiment, compounds of the invention are administered in combination with a prostaglandin analog (also referred to as prostanoids or prostacyclin analogs). Representative prostaglandin analogs include, but are not limited to, beraprost sodium, bimatoprost, epoprostenol, iloprost, latanoprost, tafluprost, travoprost, and treprostinil, with bimatoprost, latanoprost, and tafluprost being of particular interest.

In yet another embodiment, compounds of the invention are administered in combination with a prostaglandin receptor agonist, examples of which include, but are not limited to, bimatoprost, latanoprost, travoprost, and so forth.

Compounds of the invention may also be administered in combination with a renin inhibitor, examples of which include, but are not limited to, aliskiren, enalkiren, remikiren, and combinations thereof.

In another embodiment, compounds of the invention are administered in combination with a selective serotonin reuptake inhibitor (SSRI). Representative SSRIs include, but are not limited to: citalopram and the citalopram metabolite desmethylcitalopram, dapoxetine, escitalopram (e.g., escitalopram oxalate), fluoxetine and the fluoxetine desmethyl metabolite norfluoxetine, fluvoxamine (e.g., fluvoxamine maleate), paroxetine, sertraline and the sertraline metabolite demethylsertraline, and combinations thereof.

In one embodiment, compounds of the invention are administered in combination with a $5$-$HT_{1D}$ serotonin receptor agonist, examples of which include, by way of illustration and not limitation, triptans such as almotriptan, avitriptan, eletriptan, frovatriptan, naratriptan rizatriptan, sumatriptan, and zolmitriptan.

In one embodiment, compounds of the invention are administered in combination with a sodium channel blocker, examples of which include, by way of illustration and not limitation, carbamazepine, fosphenyloin, lamotrignine, lidocaine, mexiletine, oxcarbazepine, phenyloin, and combinations thereof.

In one embodiment, compounds of the invention are administered in combination with a soluble guanylate cyclase stimulator or activator, examples of which include, but are not limited to ataciguat, riociguat, and combinations thereof.

In one embodiment, compounds of the invention are administered in combination with a tricyclic antidepressant (TCA), examples of which include, by way of illustration and not limitation, amitriptyline, amitriptylinoxide, butriptyline, clomipramine, demexiptiline, desipramine, dibenzepin, dimetacrine, dosulepin, doxepin, imipramine, imipraminoxide, lofepramine, melitracen, metapramine, nitroxazepine, nortriptyline, noxiptiline, pipofezine, propizepine, protriptyline, quinupramine, and combinations thereof.

In one embodiment, compounds of the invention are administered in combination with a vasopressin receptor antagonist, examples of which include, by way of illustration and not limitation, conivaptan and tolvaptan.

Combined secondary therapeutic agents may also be helpful in further combination therapy with compounds of the invention. For example, compounds of the invention can be combined with a diuretic and an ARB, or a calcium channel blocker and an ARB, or a diuretic and an ACE inhibitor, or a calcium channel blocker and a statin. Specific examples include, a combination of the ACE inhibitor enalapril (in the maleate salt form) and the diuretic hydrochlorothiazide, which is sold under the mark Vaseretic®, or a combination of the calcium channel blocker amlodipine (in the besylate salt form) and the ARB olmesartan (in the medoxomil prodrug form), or a combination of a calcium channel blocker and a statin, all may also be used with the compounds of the invention. Other therapeutic agents such as $\alpha_2$-adrenergic receptor agonists and vasopressin receptor antagonists may also be helpful in combination therapy. Exemplary $\alpha_2$-adrenergic receptor agonists include clonidine, dexmedetomidine, and guanfacine.

The following formulations illustrate representative pharmaceutical compositions of the invention.

Exemplary Hard Gelatin Capsules for Oral Administration

A compound of the invention (50 g), 440 g spray-dried lactose and 10 g magnesium stearate are thoroughly blended. The resulting composition is then loaded into hard gelatin capsules (500 mg of composition per capsule). Alternately, a compound of the invention (20 mg) is thoroughly blended with starch (89 mg), microcrystalline cellulose (89 mg) and magnesium stearate (2 mg). The mixture is then passed through a No. 45 mesh U.S. sieve and loaded into a hard gelatin capsule (200 mg of composition per capsule).

Alternately, a compound of the invention (30 g), a secondary agent (20 g), 440 g spray-dried lactose and 10 g magnesium stearate are thoroughly blended, and processed as described above.

Exemplary Gelatin Capsule Formulation for Oral Administration

A compound of the invention (100 mg) is thoroughly blended with polyoxyethylene sorbitan monooleate (50 mg) and starch powder (250 mg). The mixture is then loaded into a gelatin capsule (400 mg of composition per capsule). Alternately, a compound of the invention (70 mg) and a secondary agent (30 mg) are thoroughly blended with polyoxyethylene sorbitan monooleate (50 mg) and starch powder (250 mg), and the resulting mixture loaded into a gelatin capsule (400 mg of composition per capsule).

Alternately, a compound of the invention (40 mg) is thoroughly blended with microcrystalline cellulose (Avicel PH 103; 259.2 mg) and magnesium stearate (0.8 mg). The mixture is then loaded into a gelatin capsule (Size #1, White, Opaque) (300 mg of composition per capsule).

Exemplary Tablet Formulation for Oral Administration

A compound of the invention (10 mg), starch (45 mg) and microcrystalline cellulose (35 mg) are passed through a No. 20 mesh U.S. sieve and mixed thoroughly. The granules so produced are dried at 50-60° C. and passed through a No. 16 mesh U.S. sieve. A solution of polyvinylpyrrolidone (4 mg as a 10% solution in sterile water) is mixed with sodium carboxymethyl starch (4.5 mg), magnesium stearate (0.5 mg), and talc (1 mg), and this mixture is then passed through a No. 16 mesh U.S. sieve. The sodium carboxymethyl starch, magnesium stearate and talc are then added to the granules. After mixing, the mixture is compressed on a tablet machine to afford a tablet weighing 100 mg.

Alternately, a compound of the invention (250 mg) is thoroughly blended with microcrystalline cellulose (400 mg), silicon dioxide fumed (10 mg), and stearic acid (5 mg). The mixture is then compressed to form tablets (665 mg of composition per tablet).

Alternately, a compound of the invention (400 mg) is thoroughly blended with cornstarch (50 mg), croscarmellose sodium (25 mg), lactose (120 mg), and magnesium stearate (5 mg). The mixture is then compressed to form a single-scored tablet (600 mg of composition per tablet).

Alternately, a compound of the invention (100 mg) is thoroughly blended with cornstarch (100 mg) with an aqueous solution of gelatin (20 mg). The mixture is dried and ground to a fine powder. Microcrystalline cellulose (50 mg) and magnesium stearate (5 mg) are then admixed with the gelatin formulation, granulated and the resulting mixture compressed to form tablets (100 mg of the compound of the invention per tablet).

Exemplary Suspension Formulation for Oral Administration

The following ingredients are mixed to form a suspension containing 100 mg of the compound of the invention per 10 mL of suspension:

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum ® K (magnesium aluminum silicate) | 1.0 g |
| Flavoring | 0.035 mL |
| Colorings | 0.5 mg |
| Distilled water | q.s. to 100 mL |

Exemplary Liquid Formulation for Oral Administration

A suitable liquid formulation is one with a carboxylic acid-based buffer such as citrate, lactate and maleate buffer solutions. For example, a compound of the invention (which may be pre-mixed with DMSO) is blended with a 100 mM ammonium citrate buffer and the pH adjusted to pH 5, or is blended with a 100 mM citric acid solution and the pH adjusted to pH 2. Such solutions may also include a solubilizing excipient such as a cyclodextrin, for example the solution may include 10 wt % hydroxypropyl-β-cyclodextrin.

Other suitable formulations include a 5% NaHCO$_3$ solution, with or without cyclodextrin.

Exemplary Injectable Formulation for Administration by Injection

A compound of the invention (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Exemplary Compositions for Administration by Inhalation

A compound of the invention (0.2 mg) is micronized and then blended with lactose (25 mg). This blended mixture is then loaded into a gelatin inhalation cartridge. The contents of the cartridge are administered using a dry powder inhaler, for example.

Alternately, a micronized compound of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of the compound of the invention per dose when administered by the inhaler.

Alternately, a compound of the invention (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1 N NaOH. The solution is administered using a nebulizer device that provides about 10 μg to about 500 μg of the compound of the invention per dose.

EXAMPLES

The following Preparations and Examples are provided to illustrate specific embodiments of the invention. These specific embodiments, however, are not intended to limit the scope of the invention in any way unless specifically indicated.

The following abbreviations have the following meanings unless otherwise indicated and any other abbreviations used herein and not defined have their standard, generally accepted meaning:

AcOH acetic acid
DCC dicyclohexylcarbodiimide
DCM dichloromethane or methylene chloride
DIPEA N,N-diisopropylethylamine
DMAP 4-dimethylaminopyridine
DMF N,N-dimethylformamide
EDCI N-(3-dimethylaminopropyl)-N'-ethylcarbodiimide
Et$_2$O diethyl ether
EtOAc ethyl acetate
EtOH ethanol
HATU N,N,N',N'-tetramethyl-O-(7-azabenzotriazol-1-yl)uronium hexafluorophosphate
HEPES 4-(2-hydroxyethyl)-1-piperazineethanesulfonic acid
HOAt 1-hydroxy-7-azabenzotriazole
HOBt 1-hydroxybenzotriazole
LiHMDS lithium hexamethyl disilazide
Mca (7-methoxycoumarin-4-yl)acyl
MeCN acetonitrile
MeOH methanol
Pd(dppf)$_2$Cl$_2$ 1,1-bis(diphenylphosphino) ferrocene palladium chloride
PMBOH p-methoxybenzyl alcohol
SilicaCat®DPP-Pd silica based diphenylphosphine palladium (II) catalyst
TFA trifluoroacetic acid
Ti(Oi-Pr)$_4$ titanium tetraisopropoxide
THF tetrahydrofuran Unless noted otherwise, all materials, such as reagents, starting materials and solvents, were purchased from commercial suppliers (such as Sigma-Aldrich, Fluka Riedel-de Haën, and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% H$_2$O/2% MeCN/1.0 mL/L TFA; solvent B was 90% MeCN/10% H$_2$O/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Progress of reactions was typically measured by liquid chromatography mass spectrometry (LCMS). Characterization of isomers were done by Nuclear Overhauser effect spectroscopy (NOE). Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

[(S)-1-Biphenyl-4-ylmethyl-2-(2,2-dimethyl-4,6-dioxo-[1,3]dioxan-5-yl)-ethyl]-carbamic Acid t-Butyl Ester

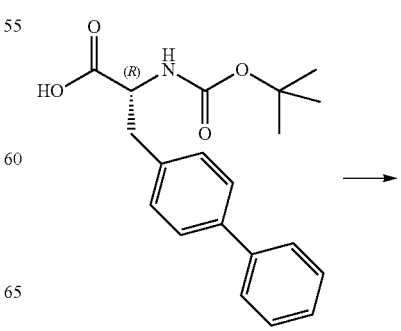

-continued

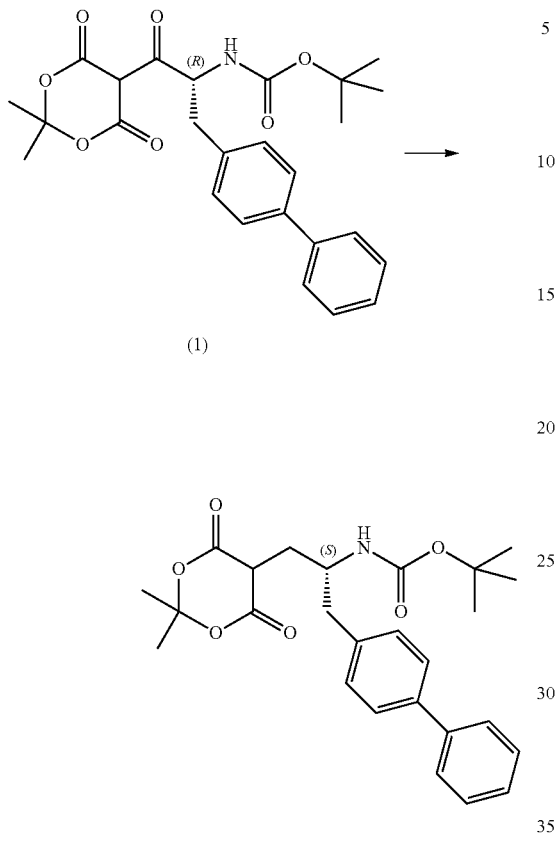

(1)

Step 1: To a solution of (R)-3-biphenyl-4-yl-2-t-butoxycarbonylamino-propionic acid (50 g, 0.1 mol), Meldrum's acid (23.3 g, 0.2 mol) and DMAP (27.8 g, 0.2 mol) in anhydrous DCM (500 mL) was added a solution of DCC (33.3 g, 0.2 mol) in anhydrous DCM (200 mL) over 1 hour at −5° C. under nitrogen. The mixture was stirred at −5° C. for 8 hours, then refrigerated overnight, during which tiny crystals of dicyclohexylurea precipitated. After filtration, the mixture was washed with 5% KHSO$_4$ (4×200 mL), saturated aqueous NaCl (200 mL) and dried under refrigeration with MgSO$_4$ overnight. The resulting solution was evaporated to yield crude compound 1 as a light yellow solid (68 g). LC-MS: [M+Na]: 490, [2M+Na]: 957.

Step 2: To a solution of crude compound 1 (68 g, 0.1 mol) in anhydrous DCM (1 L) was added AcOH (96.8 g, 1.6 mol) at −5° C. under nitrogen. The mixture was stirred at −5° C. for 0.5 hour, then NaBH$_4$ (13.9 g, 0.4 mol) was added in small portions over 1 hour. After stirring at −5° C. for another 1 hour, saturated aqueous NaCl (300 mL) was added. The organic layer was washed with saturated aqueous NaCl (2×300 mL) and water (2×300 mL), dried over MgSO$_4$, filtered, and concentrated to give the crude product which was further purified by chromatography (hexanes:EtOAc=5:1) to yield the title compound as a light yellow solid (46 g). LC-MS: [M+Na]: 476, [2M+Na]: 929.

Preparation 2

(R)-4-Amino-5-biphenyl-4-yl-2-hydroxy-2-methyl-pentanoic Acid Ethyl Ester

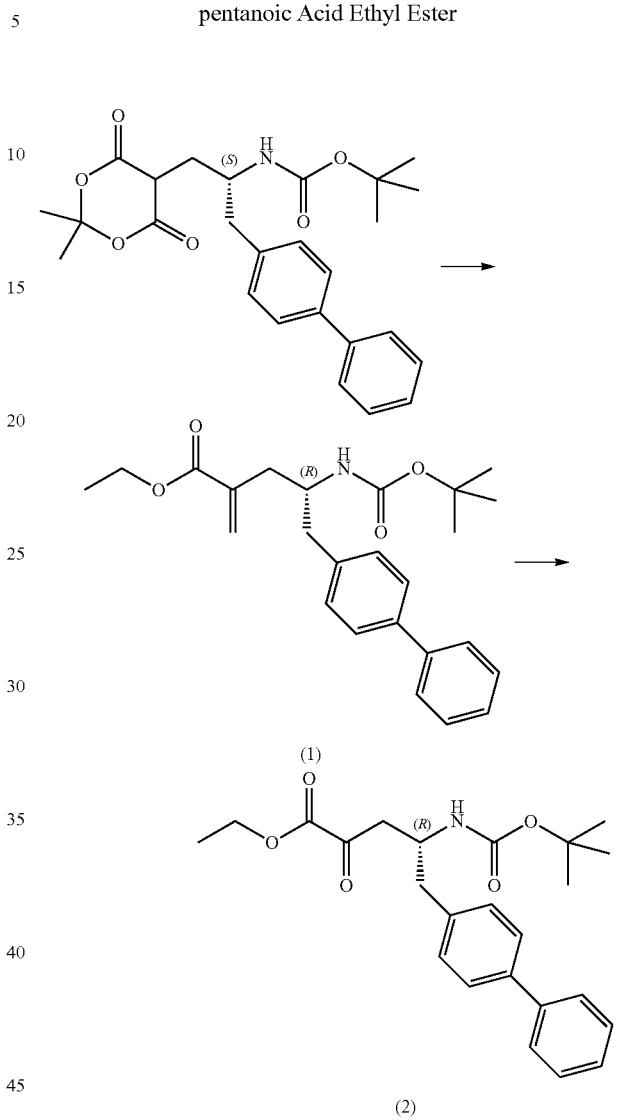

Step 1: To a solution of [(S)-1-biphenyl-4-ylmethyl-2-(2, 2-dimethyl-4,6-dioxo-[1,3]dioxan-5-yl)-ethyl]-carbamic acid t-butyl ester (46 g, 0.1 mol) in tertiary butyl alcohol (100 mL) was added dimethylmethyleneimmonium iodide (46.3 g, 0.3 mol) at room temperature under nitrogen. The mixture was heated to 65° C. and stirred at this temperature for 16 hours. After filtration, the filtrate was concentrated to give the crude product which was further purified by chromatography (hexanes:EtOAc=20:1~10:1) to yield compound 1 as a light yellow solid (18 g). LC-MS: [M+Na]: 460, [2M+Na]: 897.

Step 2: To a solution of compound 1 (18 g, 44 mmol) in acetone (430 mL) and water (22 mL) was added Sudan Red as indicator. Ozone atmosphere was introduced into the mixture at 0° C. until the red color of Sudan Red disappeared. Dimethyl sulfide (45 mL) was added and the mixture was stirred at room temperature overnight. The mixture was then concentrated and the residue was purified by chromatography (hexanes:EtOAc=15:1~7:1) to yield compound 2 as a light yellow solid (9.5 g). LC-MS: [M+H]: 434, [2M+H]: 845.

83

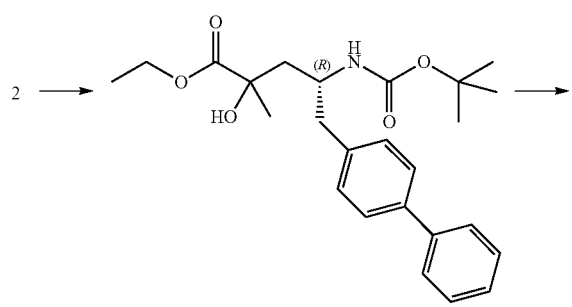

(3)

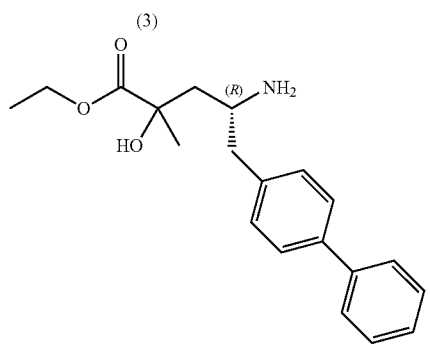

Step 3: To a solution of compound 2 (9.5 g, 23 mmol) in anhydrous THF (120 mL) was added a solution of methylmagnesium bromide in THF (9.2 mL, 28 mmol) at −70° C. under nitrogen. The mixture was stirred at −60° C. for 3 hours and the reaction was then quenched with saturated aqueous NH$_4$Cl (50 mL). The organic layer was separated and dried over MgSO$_4$. The mixture was then concentrated and the residue was purified by chromatography (hexanes: EtOAc=10:1~5:1) to yield compound 3 as an oil (7.9 g). LC-MS: [M+H]: 450, [2M+H]: 877.

Step 4: To a solution of compound 3 (7.9 g, 18.4 mmol) in anhydrous DCM (300 mL) was pumped HCl atmosphere at 0° C. for 6 hours. The mixture was then concentrated and the residue was washed with anhydrous Et$_2$O to yield the title compound as a white solid HCl salt (5.8 g). LC-MS: [M+H]: 364, [2M+H]: 727. $^1$H NMR (300 MHz, DMSO): δ8.00-7.97 (d, 4H), 7.67-7.62 (m, 6H), 7.47-7.28 (m, 8H), 6.32 (s, 1H), 6.09 (s, 1H), 4.13-4.06 (m, 2H), 3.95-3.78 (m, 2H), 3.60 (s, 1H), 3.22-3.08 (m, 3H), 2.95-2.65 (m, 2H), 1.99-1.79 (m, 4H), 1.30-0.87 (m, 9H).

Example 1

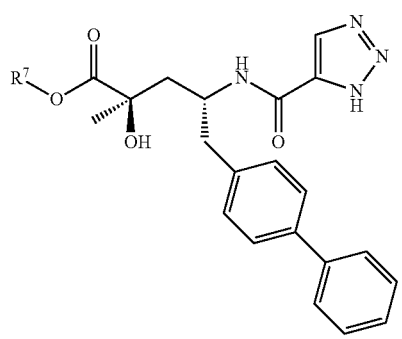

84

A. (2R,4R)-5-Biphenyl-4-yl-2-hydroxy-2-methyl-4-[(3H-[1,2,3]triazole-4-carbonyl)-amino]-pentanoic acid ethyl ester (R$^7$=CH$_2$CH$_3$)

B. (2R,4R)-5-Biphenyl-4-yl-2-hydroxy-2-methyl-4-[(3H-[1,2,3]triazole-4-carbonyl)-amino]-pentanoic acid (R$^7$=H)

(R)-4-Amino-5-biphenyl-4-yl-2-hydroxy-2-methyl-pentanoic acid ethyl ester (300 mg, 916 μmol, 1.0 eq.), 1,2,3-triazole-4-carboxylic acid (114 mg, 1.0 mmol, 1.1 eq.), and DIPEA (479 μL, 2.8 mmol, 3.0 eq.) were dissolved in DMF (6.0 mL). HATU (383 mg, 1.0 mmol, 1.1 eq.) was added and the mixture was stirred at room temperature overnight. The mixture was split 50/50 and the two solutions were concentrated. One portion was purified by preparative HPLC (10-70% MeCN/water), followed by isomer separation by preparative HPLC to yield compound A (27 mg, 96% purity). MS m/z [M+H]$^+$ calc'd for C$_{23}$H$_{26}$N$_4$O$_4$, 423.20; found 423.2.

The remaining portion was dissolved in THF (2.0 mL), followed by the addition of lithium hydroxide monohydrate (192 mg, 4.6 mmol) in water (2.0 mL). The resulting mixture was stirred at room temperature until the reaction was complete (~70 minutes). The reaction was quenched by addition of AcOH, then the solution was concentrated. The crude product was purified by preparative HPLC (10-70% MeCN/water), followed by isomer separation by preparative HPLC to yield the compound B (24.9 mg, 100% purity). MS m/z [M+H]$^+$ calc'd for C$_{21}$H$_{22}$N$_4$O$_4$, 395.16; found 395.2.

Example 2

Following the procedures described in the examples herein, and substituting the appropriate starting materials and reagents, compounds having formula IIIa-1, were also prepared:

(IIIa-1)

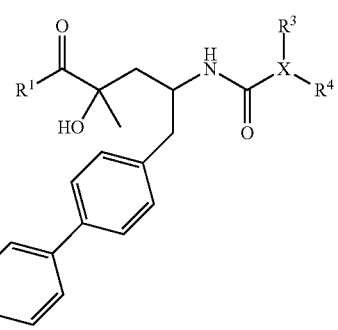

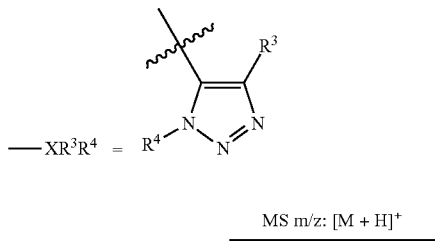

| Ex. | R¹ | R³ | R⁴ | Formula | calcd | found |
|---|---|---|---|---|---|---|
| 1 | —OH | H | H | $C_{21}H_{22}N_4O_4$ | 395.16 | 395.2 |

1. (2S,4R)-5-Biphenyl-4-yl-2-hydroxy-2-methyl-4-[(3H-[1,2,3]triazole-4-carbonyl)-amino]-pentanoic acid

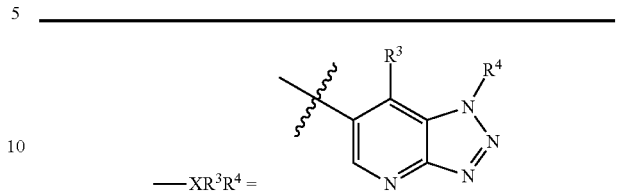

| Ex. | R¹ | R³ | R⁴ | Formula | calcd | found |
|---|---|---|---|---|---|---|
| 2 | —OH | H | H | $C_{21}H_{22}N_4O_4$ | 395.16 | 395.0 |
| 3 | —OH | Cl | H | $C_{21}H_{21}ClN_4O_4$ | 429.13 | 429.4 |

2. (R)-5-Biphenyl-4-yl-2-hydroxy-2-methyl-4-[(2H-[1,2,4]triazole-3-carbonyl)-amino]-pentanoic acid
3. (R)-5-Biphenyl-4-yl-4-[(5-chloro-2H-[1,2,4]triazole-3-carbonyl)-amino]-2-hydroxy-2-methyl-pentanoic acid

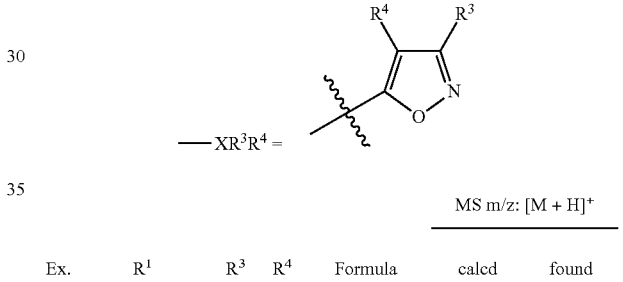

| Ex. | R¹ | R³ | R⁴ | Formula | calcd | found |
|---|---|---|---|---|---|---|
| 4 | —OH | F | H | $C_{25}H_{23}FN_4O_4$ | 463.17 | 463.0 |
| 5 | —OH | Cl | H | $C_{25}H_{23}ClN_4O_4$ | 479.14 | 479.0 |

4. (R)-5-Biphenyl-4-yl-4-[(7-fluoro-3H-benzotriazole-5-carbonyl)-amino]-2-hydroxy-2-methyl-pentanoic acid
5. (R)-5-Biphenyl-4-yl-4-[(7-chloro-3H-benzotriazole-5-carbonyl)-amino]-2-hydroxy-2-methyl-pentanoic acid

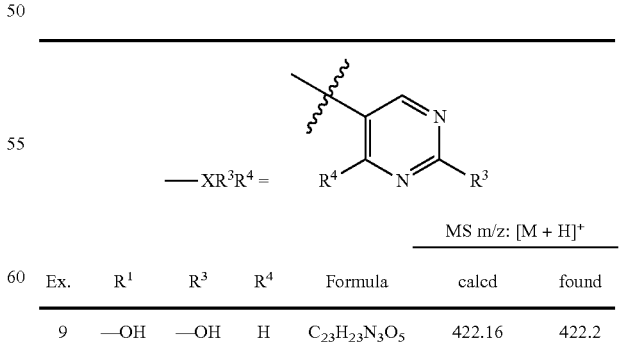

| Ex. | R¹ | R³ | R⁴ | Formula | calcd | found |
|---|---|---|---|---|---|---|
| 6 | —OH | H | H | $C_{24}H_{23}N_5O_4$ | 446.18 | 446.4 |

6. (2S,4R)-5-Biphenyl-4-yl-2-hydroxy-2-methyl-4-[(1H-[1,2,3]triazolo[4,5-b]pyridine-6-carbonyl)-amino]-pentanoic acid

| Ex. | R¹ | R³ | R⁴ | Formula | calcd | found |
|---|---|---|---|---|---|---|
| 7 | —OH | —OH | H | $C_{22}H_{22}N_2O_6$ | 411.15 | 411.2 |
| 8 | —O—CH₂CH₃ | —OH | H | $C_{24}H_{26}N_2O_6$ | 439.18 | 439.4 |

7. (R)-5-Biphenyl-4-yl-2-hydroxy-4-[(3-hydroxy-isoxazole-5-carbonyl)-amino]-2-methyl-pentanoic acid
8. (R)-5-Biphenyl-4-yl-2-hydroxy-4-[(3-hydroxy-isoxazole-5-carbonyl)-amino]-2-methyl-pentanoic acid ethyl ester

| Ex. | R¹ | R³ | R⁴ | Formula | calcd | found |
|---|---|---|---|---|---|---|
| 9 | —OH | —OH | H | $C_{23}H_{23}N_3O_5$ | 422.16 | 422.2 |
| 10 | —OH | —OH | H | $C_{23}H_{23}N_3O_5$ | 422.16 | 422.2 |

9. (2R,4R)-5-Biphenyl-4-yl-2-hydroxy-4-[(2-hydroxy-pyrimidine-5-carbonyl)-amino]-2-methyl-pentanoic acid 10. (2S,4R)-5-Biphenyl-4-yl-2-hydroxy-4-[(2-hydroxy-pyrimidine-5-carbonyl)-amino]-2-methyl-pentanoic acid

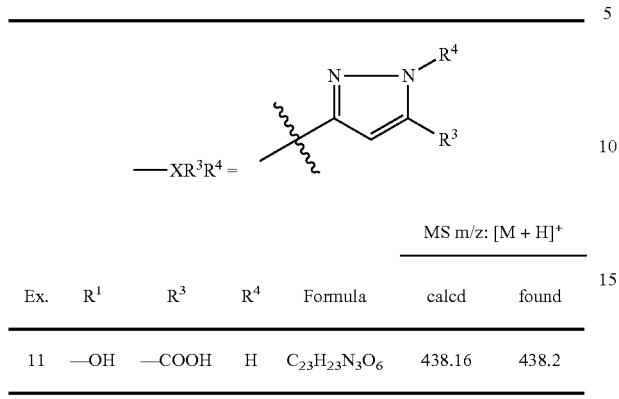

| Ex. | $R^1$ | $R^3$ | $R^4$ | Formula | MS m/z: [M + H]$^+$ calcd | found |
|---|---|---|---|---|---|---|
| 11 | —OH | —COOH | H | $C_{23}H_{23}N_3O_6$ | 438.16 | 438.2 |

11. 5-((1R,3S)-1-Biphenyl-4-ylmethyl-3-carboxy-3-hydroxy-butylcarbamoyl)-2H-pyrazole-3-carboxylic acid

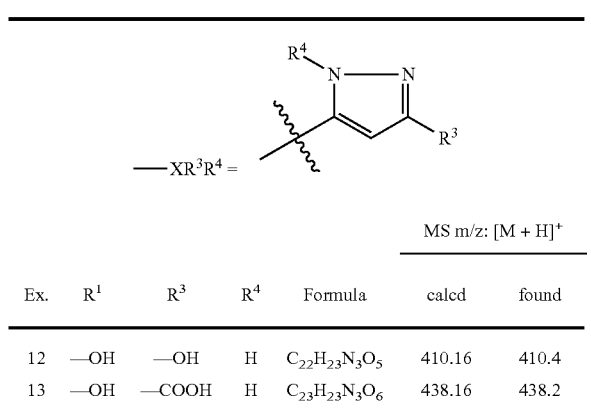

| Ex. | $R^1$ | $R^3$ | $R^4$ | Formula | MS m/z: [M + H]$^+$ calcd | found |
|---|---|---|---|---|---|---|
| 12 | —OH | —OH | H | $C_{22}H_{23}N_3O_5$ | 410.16 | 410.4 |
| 13 | —OH | —COOH | H | $C_{23}H_{23}N_3O_6$ | 438.16 | 438.2 |

12. (R)-5-Biphenyl-4-yl-2-hydroxy-4-[(5-hydroxy-2H-pyrazole-3-carbonyl)-amino]-2-methyl-pentanoic acid
13. 5-((1R,3R)-1-Biphenyl-4-ylmethyl-3-carboxy-3-hydroxy-butylcarbamoyl)-1H-pyrazole-3-carboxylic acid Preparation 3

3-(N-Biphenyl-4-ylmethyl-N'-t-butoxycarbonyl-hydrazino)-2-hydroxy-2-methyl-propionic Acid Methyl Ester

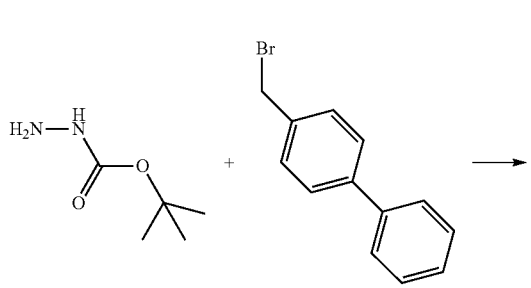

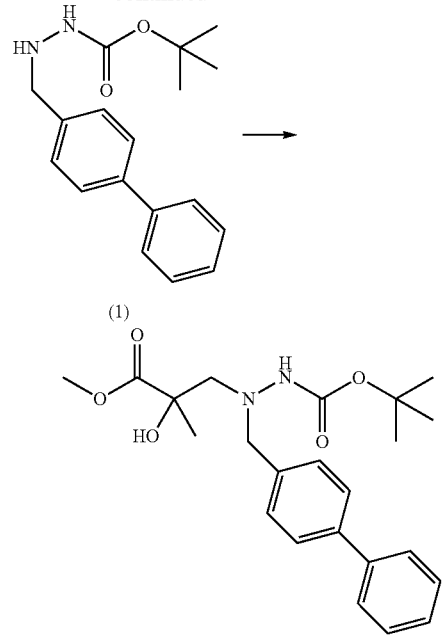

Step 1: 4-(Bromomethyl)biphenyl (2.0 g, 8.1 mmol, 1.0 eq.) and DIPEA (1.4 mL) were dissolved in DMF (40 mL). t-Butyl carbazate (2.1 g, 16.2 mmol, 2.0 eq.) was added and the mixture was stirred at room temperature until the reaction was complete (several days). The mixture was partially concentrated, and the residue was partitioned between EtOAc and saturated aqueous NaHCO$_3$ solution. The EtOAc layer was then dried over Na$_2$SO$_4$ and concentrated. The crude product was purified by flash chromatography (0-60% EtOAc/hexanes w/0.5% DIPEA) to yield compound 1 (1.3 g).

Step 2: Compound 1 (1.3 g, 4.3 mmol, 1.0 eq.) was dissolved in isopropyl alcohol (20.0 mL). Methyl 2-methylglycidate (676 µL, 1.5 eq.) was added and the resulting mixture was heated at 85° C. until the reaction was 70% complete (several days). The mixture was partitioned between EtOAc and saturated aqueous NaHCO$_3$ solution, then the EtOAc layer was dried over Na$_2$SO$_4$ and concentrated. The crude product was purified by flash chromatography (0-60% EtOAc/hexanes w/0.1% DIPEA) to yield the title compound (1.1 g)

Example 3

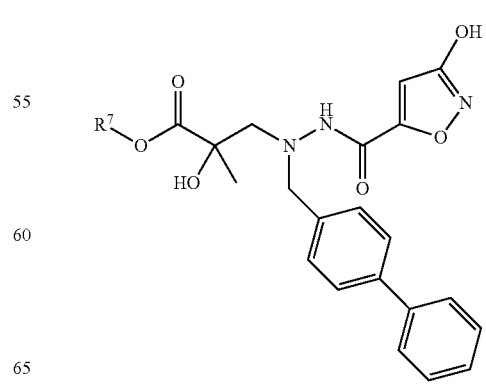

A. 3-[N-Biphenyl-4-ylmethyl-N'-(3-hydroxy-isoxazole-5-carbonyl)-hydrazino]-2-hydroxy-2-methyl-propionic acid ethyl ester ($R^7$=—$CH_2CH_3$)

B. 3-[N-Biphenyl-4-ylmethyl-N'-(3-hydroxy-isoxazole-5-carbonyl)-hydrazino]-2-hydroxy-2-methyl-propionic acid ($R^7$=H)

3-(N-Biphenyl-4-ylmethyl-N'-t-butoxycarbonyl-hydrazino)-2-hydroxy-2-methyl-propionic acid methyl ester (400 mg, 965 μmol, 1.0 eq.) was dissolved in DCM (4.0 mL). TFA (4.0 mL) was added and the mixture was stirred at room temperature until the reaction was complete (~1 hour). The mixture was then concentrated. 3-Hydroxyisoxazole-5-carboxylic acid (137 mg, 1.1 mmol, 1.1 eq.) was dissolved in DMF (4 mL), then DIPEA (504 μL), HOAt (144 mg, 1.1 mmol, 1.1 eq.) and EDCI (188 μL) were added and the mixture was stirred for 15 minutes. To this was added the concentrated mixture from above in DMF (4 mL) and the resulting mixture was stirred at room temperature until the reaction was complete (overnight). The reaction mixture was split 50/50 and the two solutions were concentrated. One portion was purified by preparative HPLC (10-70% MeCN/water). A solution of HCl in EtOH was prepared by the addition of acetyl chloride (427 mL) to EtOH (6 mL). 130 mg of the purified portion was then added and the mixture was stirred at 50° C. until the reaction was complete (~2.5 hours). The mixture was concentrated and the crude product was purified by preparative HPLC (10-70% MeCN/water) to yield compound A (99.6 mg, 99% purity). MS m/z [M+H]$^+$ calc'd for $C_{23}H_{25}N_3O_6$, 440.17; found 440.4.

The remaining portion was dissolved in THF (3.0 mL), followed by the addition of lithium hydroxide monohydrate (202 mg, 4.8 mmol) in water (3.0 mL). The resulting mixture was stirred at room temperature until the reaction was complete (~45 minutes). The reaction was quenched by addition of AcOH, then the solution was concentrated. The crude product was purified by preparative HPLC (10-70% MeCN/water) to yield compound B (58.2 mg, 97% purity). MS m/z [M+H]$^+$ calc'd for $C_{21}H_{21}N_3O_6$, 412.14; found 412.4.

Example 4

Following the procedures described in the examples herein, and substituting the appropriate starting materials and reagents, compounds having formula IIIb-1, were also prepared:

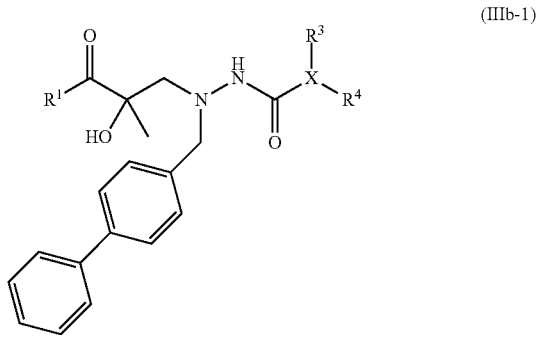
(IIIb-1)

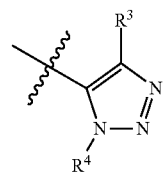

—$XR^3R^4$ =

| Ex. | $R^1$ | $R^3$ | $R^4$ | Formula | MS m/z: [M + H]$^+$ calcd | found |
|---|---|---|---|---|---|---|
| 1 | —OH | H | H | $C_{20}H_{21}N_5O_4$ | 396.16 | 396.2 |

1. 3-[N-Biphenyl-4-ylmethyl-N'-(3H-[1,2,3]triazole-4-carbonyl)-hydrazino]-2-hydroxy-2-methyl-propionic acid

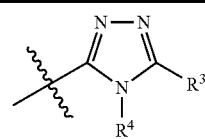

—$XR^3R^4$ =

| Ex. | $R^1$ | $R^3$ | $R^4$ | Formula | MS m/z: [M + H]$^+$ calcd | found |
|---|---|---|---|---|---|---|
| 2 | —OH | Cl | H | $C_{20}H_{20}ClN_5O_4$ | 430.12 | 430.4 |

2. 3-[N-Biphenyl-4-ylmethyl-N'-(5-chloro-4H-[1,2,4]triazole-3-carbonyl)-hydrazino]-2-hydroxy-2-methyl-propionic acid

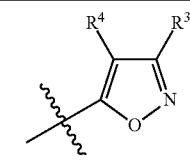

—$XR^3R^4$ =

| Ex. | $R^1$ | $R^3$ | $R^4$ | Formula | MS m/z: [M + H]$^+$ calcd | found |
|---|---|---|---|---|---|---|
| 3 | —OH | —OCH$_3$ | H | $C_{22}H_{23}N_3O_6$ | 426.16 | 426.4 |

3. 3-[N-Biphenyl-4-ylmethyl-N'-(3-methoxy-isoxazole-5-carbonyl)-hydrazino]-2-hydroxy-2-methyl-propionic acid

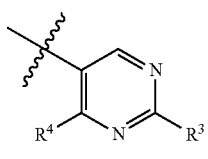

—$XR^3R^4$ =

| Ex. | $R^1$ | $R^3$ | $R^4$ | Formula | MS m/z: [M + H]$^+$ calcd | found |
|---|---|---|---|---|---|---|
| 4 | —OH | —OH | H | $C_{22}H_{22}N_4O_5$ | 423.16 | 423.2 |

4. 3-[N-Biphenyl-4-ylmethyl-N'-(2-hydroxy-pyrimidine-5-carbonyl)-hydrazino]-2-hydroxy-2-methyl-propionic acid

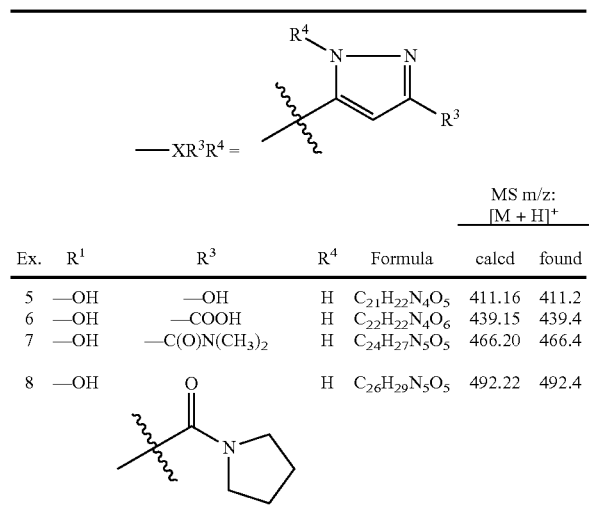

| Ex. | R¹ | R³ | R⁴ | Formula | MS m/z: [M + H]⁺ calcd | found |
|---|---|---|---|---|---|---|
| 5 | —OH | —OH | H | $C_{21}H_{22}N_4O_5$ | 411.16 | 411.2 |
| 6 | —OH | —COOH | H | $C_{22}H_{22}N_4O_6$ | 439.15 | 439.4 |
| 7 | —OH | —C(O)N(CH₃)₂ | H | $C_{24}H_{27}N_5O_5$ | 466.20 | 466.4 |
| 8 | —OH | (pyrrolidinyl carbonyl group) | H | $C_{26}H_{29}N_5O_5$ | 492.22 | 492.4 |

5. 3-[N-Biphenyl-4-ylmethyl-N'-(5-hydroxy-2H-pyrazole-3-carbonyl)-hydrazino]-2-hydroxy-2-methyl-propionic acid
6. 5-[N'-Biphenyl-4-ylmethyl-N'-(2-carboxy-2-hydroxy-propyl)-hydrazinocarbonyl]-1H-pyrazole-3-carboxylic acid
7. 3-[N-Biphenyl-4-ylmethyl-N'-(5-dimethylcarbamoyl-2H-pyrazole-3-carbonyl)-hydrazino]-2-hydroxy-2-methyl-propionic acid
8. 3-{N-Biphenyl-4-ylmethyl-N'-[5-(pyrrolidine-1-carbonyl)-2H-pyrazole-3-carbonyl]-hydrazino}-2-hydroxy-2-methyl-propionic acid Preparation 4

3-[N'-t-Butoxycarbonyl-N-(3'-fluorobiphenyl-4-ylmethyl)-hydrazino]-2-hydroxy-2-methyl-propionic Acid Methyl Ester

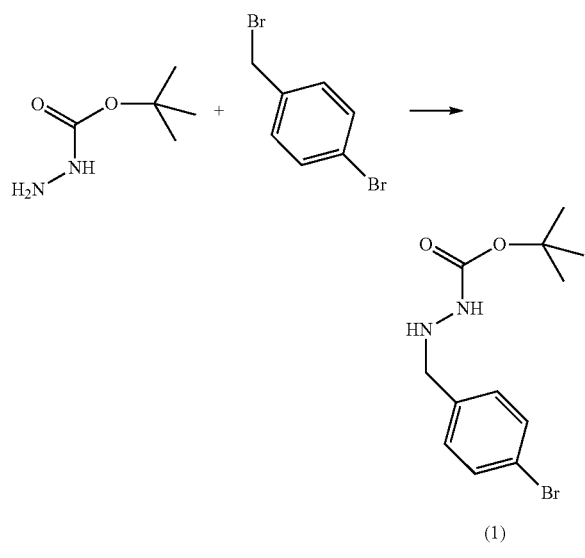

Step 1: 4-Bromobenzyl bromide (2.0 g, 8.1 mmol, 1.0 eq.) and DIPEA (1.4 mL) were dissolved in DMF (40.0 mL). t-Butyl carbazate (2.1 g, 16.2 mmol, 2.0 eq.) was added and the mixture was stirred at room temperature until the reaction was complete (~overnight). The mixture was partially concentrated, then the residue was partitioned between EtOAc and saturated sodium bicarbonate. The EtOAc layer was then dried over $Na_2SO_4$ and concentrated. The crude product was purified by flash chromatography (0-60% EtOAc/hexanes w/0.1% DIPEA) to yield compound 1 (1.4 g).

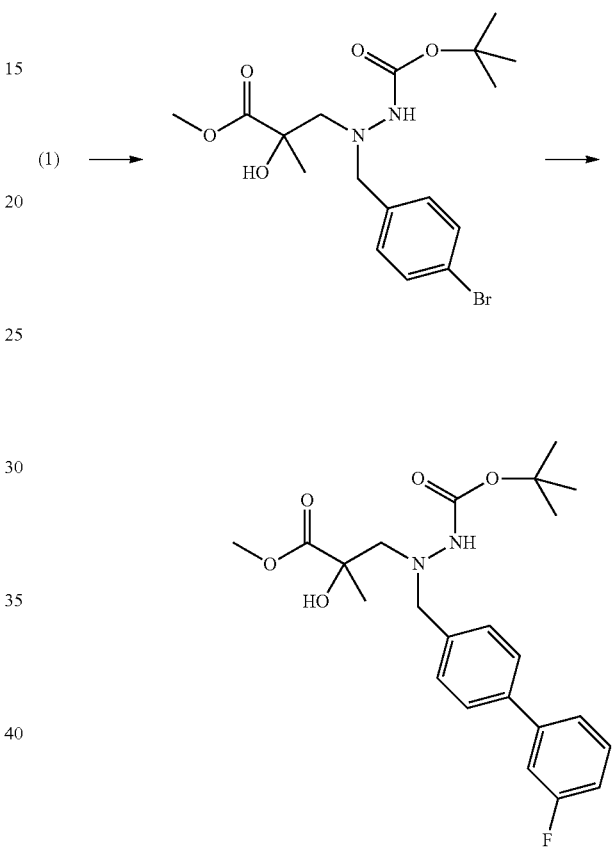

Step 2: Compound 1 (720 mg, 2.4 mmol, 1.0 eq.) was dissolved in isopropyl alcohol (10.0 mL). Methyl 2-methylglycidate (380 μL) was added and the mixture was stirred at 85° C. until the reaction was complete (several days). The mixture was partitioned between EtOAc and saturated sodium bicarbonate. The EtOAc layers were dried over $Na_2SO_4$ and concentrated to yield crude compound 2 (890 mg), which was used without further purification.

Step 3: Compound 2 (642 mg, 1.5 mmol, 1.0 eq.), 3-Fluorophenylboronic acid (430 mg, 3.1 mmol, 2.0 eq.) and $K_2CO_3$ (637 mg, 4.6 mmol) were dissolved in a mixture of THF (12.0 mL) and water (12.0 mL). The reaction flask was then purged with nitrogen, Tetrakis(triphenylphosphine)palladium(0) (355 mg, 307 mmol) was added, and the reaction mixture was stirred at 90° C. until the reaction was complete (overnight). The mixture was diluted with water then was extracted twice with EtOAc. The EtOAc layers were then dried over $Na_2SO_4$ and concentrated. The crude product was purified by preparative HPLC (10-80% MeCN/water) to yield the title compound (342 mg).

Example 5

3-[N-(3'-Fluorobiphenyl-4-ylmethyl)-N'-(3-hydroxy-isoxazole-5-carbonyl)-hydrazino]-2-hydroxy-2-methyl-propionic Acid

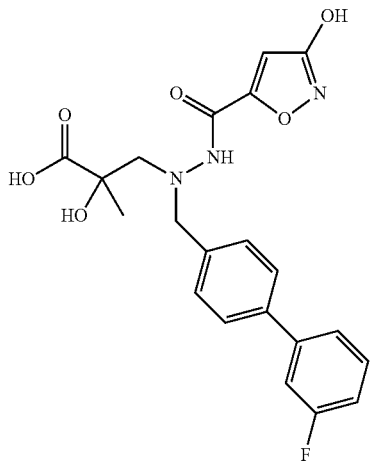 [SMILES: CC(O)(CN(Cc1ccc(-c2cccc(F)c2)cc1)NC(=O)c1cc(O)no1)C(=O)O]

3-[N'-t-Butoxycarbonyl-N-(3'-fluorobiphenyl-4-ylmethyl)-hydrazino]-2-hydroxy-2-methyl-propionic acid methyl ester (100 mg, 231 mmol, 1.0 eq.) was dissolved in DCM (2.0 mL). TFA (2.0 mL) was added and the mixture was stirred at room temperature until the reaction was complete (~45 minutes). The mixture was then concentrated. 3-Hydroxyisoxazole-5-carboxylic acid (38.8 mg, 300 mmol, 1.3 eq.) and 1 HOAt (40.9 mg, 300 µmol, 1.3 eq.) were dissolved in DMF (2 mL) of DMF, then EDCI (53.2 µL) was added followed by DIPEA (121 µL) and the mixture was stirred for 30 minutes. To this was added the concentrated mixture from above in DMF (2 mL) and the resulting mixture was stirred at room temperature until the reaction was complete (~2.5 hours). The mixture was then dissolved in THF (2.0 mL), followed by the addition of lithium hydroxide monohydrate (97.0 mg, 2.3 mmol) in water (2.0 mL. The resulting mixture was stirred at room temperature until the reaction was complete (~1 hour). The reaction was quenched by addition of AcOH, then the solution was concentrated. The crude product was purified by preparative HPLC (10-70% MeCN/water) to yield the title compound (43 mg; purity 99%). MS m/z [M+H]$^+$ calc'd for $C_{21}H_{20}FN_3O_6$, 430.13; found 430.4.

Preparation 5

(R)-4-methoxybenzyl 2-methyloxirane-2-carboxylate

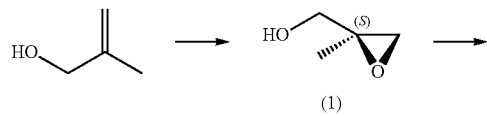

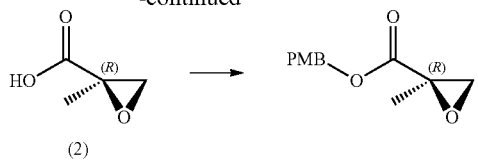

To a solution of (R,R) diethyl tartrate (6.2 g, 30 mmol) and Ti(Oi-Pr)$_4$ (7.1 g, 25 mmol) in dry DCM (500 mL) was added fresh dried 4 Å molecular sieve (30 g) at room temperature. The resulting mixture was cooled to −30° C. and t-butyl hydroperoxide (5.5M in decane, 100 mL, 550 mmol) was added and the solution was stirred for 30 minutes at −30° C.~−20° C. Then, a solution of 2-methyl-2-propen-1-ol (36 g, 0.5 mol) in dry DCM (100 mL) was added dropwise at −30° C.~−20° C. After the addition, the mixture was stirred at −20° C. until the reaction was complete (2 days). The mixture was filtered and the filtrate was cooled to 0° C. A solution of Na$_2$SO$_3$ (18 g) in water (50 mL) was added dropwise to quench the reaction. The mixture was stirred for 1 hour at 0° C. and filtered. The DCM layer was separated and the aqueous layer was extracted with DCM (5×40 mL). The combined organic solution was dried over anhydrous Na$_2$SO$_4$, concentrated at 0° C. under vacuum and purified (silica gel chromatography; hexanes to DCM to Et$_2$O) to yield compound 1 (28 g) as a colorless oil.

To a suspension of NaIO$_4$ (72.95 g, 340 mmol) and NaHCO$_3$ (47.9 g, 570 mmol) in water (340 mL) was added compound 1 (10 g, 114 mmol) and CCl$_4$ (220 mL)/CHCl$_3$ (220 mL), followed by RuCl$_3$ (0.5 g). After the addition, the mixture was stirred until the reaction was complete (4 hours). The mixture was filtered and the filtrate was concentrated under vacuum. The aqueous layer was acidified to pH=2-3 with concentrated HCl, then extracted with DCM/isopropanol (3:1, 6×300 mL). The combined organic solution was dried over anhydrous Na$_2$SO$_4$ and concentrated to yield compound 2 (12 g) as a colorless oil.

To a solution of compound 2 (12 g, 118 mmol) and PMBOH (16.2 g, 118 mmol) in dry DCM (200 mL) was added EDCI (27 g, 140 mmol) and DMAP (4.3 g, 35.4 mmol) at 0° C. After the addition, the mixture was stirred at room temperature until the reaction was complete (overnight). The mixture was washed with water (200 mL), saturated KHSO$_4$ (200 mL), saturated aqueous NaCl (100 mL), and dried over Na$_2$So$_4$, then concentrated under vacuum. The crude product was purified (silica gel chromatography; hexanes:EtOAc=20:1) to yield the title compound (18 g) as a colorless oil (PMB=p-methoxybenzyl).

Preparation 6

(R)-3-[N-(4-Bromobenzyl)hydrazino]-2-hydroxy-2-methyl-propionic Acid Ethyl Ester

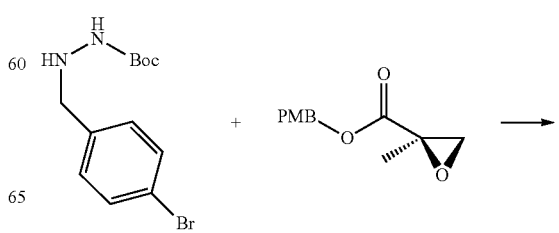

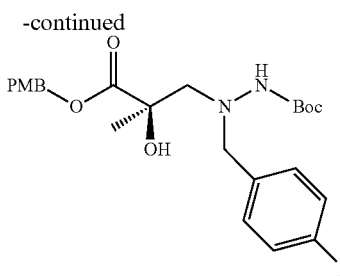

(1)

To a solution of t-butyl 2-(4-bromobenzyl)hydrazinecarboxylate (9.5 g, 31.5 mmol) in isopropyl alcohol (170 mL) was added (R)-4-methoxybenzyl 2-methyloxirane-2-carboxylate (7 g, 31.5 mmol) under nitrogen. The mixture was heated under reflux for 4 days, then cooled to room temperature. The mixture was concentrated under vacuum and the residue was purified by silica gel chromatography (hexanes: EtOAc, 4:1) to yield compound 1 (7.9 g) as a white solid. LC-MS: [M+Na]$^+$: 545/547.

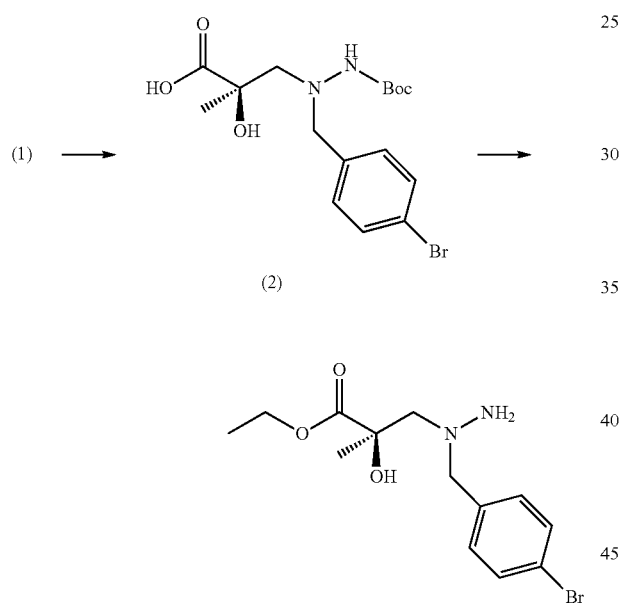

To a stirred solution of compound 1 (7.9 g, 15.0 mmol) in EtOH (80 mL) was added LiOH.H$_2$O (0.8 g, 19.5 mmol). The mixture was stirred at 55° C. for 3 hours, then cooled to room temperature. The mixture was concentrated, diluted with water (80 mL), and washed with EtOAc (40 mL×3). The aqueous solution was acidified with 1N HCl to pH=3, then, extracted with EtOAc (80 mL×3). The combined organic layers were washed with saturated aqueous NaCl (80 mL), dried over anhydrous Na$_2$SO$_4$, and concentrated under vacuum to yield compound 2 (5.5 g) as a white solid. LC-MS: [M+Na]$^+$: 425/427.

Compound 2 (6.5 g, 16.1 mmol) was dissolved in HCl/EtOH (1M, 50 mL), and the mixture was stirred overnight at room temperature. The resulting mixture was neutralized with aqueous Na$_2$CO$_3$ (1N) to pH=8, then, concentrated under vacuum and extracted with EtOAc (50 mL×3). The combined organic layers were acidified with 1N HCl to pH=6, then extracted with water (50 mL×3). The combined aqueous layers were washed with EtOAc (50 mL×3) and concentrated to yield the title compound (2.0 g) as a light yellow solid HCl salt. LC-MS: [M+H]$^+$: 331/333. $^1$H NMR: (CD$_3$OD) 1.114 (t, J=6.9 Hz, 3H), 1.344 (s, 3H), 2.844-2.902 (m, 1H), 3.151 (d, J=13.8 Hz, 1H), 3.834-3.943 (m, 2H), 4.019-4.068 (m, 1H), 4.118-4.202 (m, 1H), 7.253-7.280 (m, 2H), 7.545-7.573 (m, 2H).

Preparation 7

(R)-3-[N-(5'-Chloro-2'-fluorobiphenyl-4-ylmethyl)-hydrazino]-2-hydroxy-2-methyl-propionic Acid Ethyl Ester

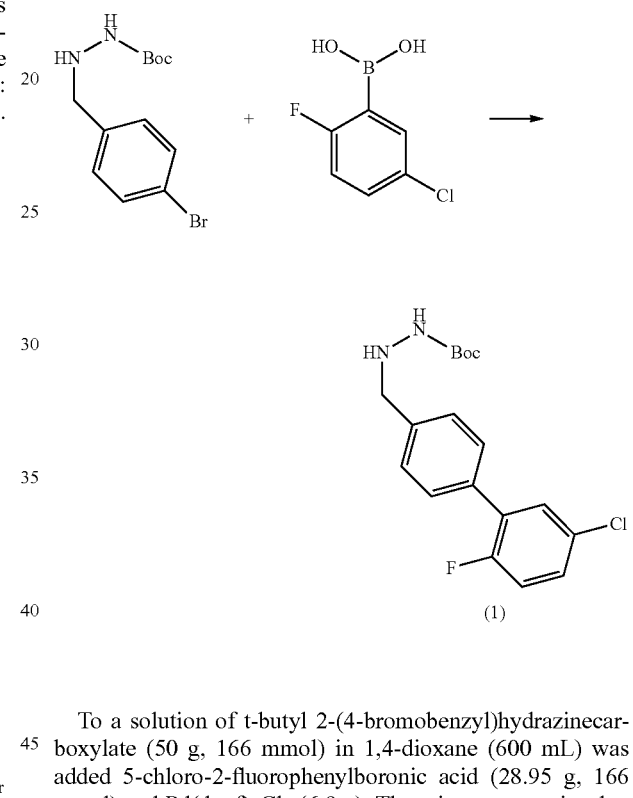

To a solution of t-butyl 2-(4-bromobenzyl)hydrazinecarboxylate (50 g, 166 mmol) in 1,4-dioxane (600 mL) was added 5-chloro-2-fluorophenylboronic acid (28.95 g, 166 mmol) and Pd(dppf)$_2$Cl$_2$ (6.9 g). The mixture was stirred at room temperature under nitrogen for 10 minutes, then K$_2$CO$_3$ (45.9 g, 332 mmol) in water (180 mL) was added. The mixture was stirred at 80° C. for 5 hours, then cooled to room temperature and concentrated under vacuum. The residue was extracted with EtOAc (3×200 mL) and the combined organic layers were washed with saturated aqueous NaCl (200 mL), dried over anhydrous Na$_2$SO$_4$, and concentrated under vacuum. The residue was purified by silica gel chromatography (hexanes/EtOAc, 15:1-4:1) to yield compound 1 (38 g) as an off-white solid. LC-MS: [M+H]$^+$: 351; [M−tBu+H]$^+$: 295.

(1) + 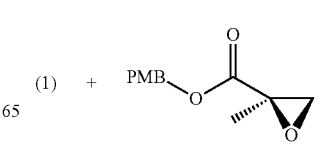

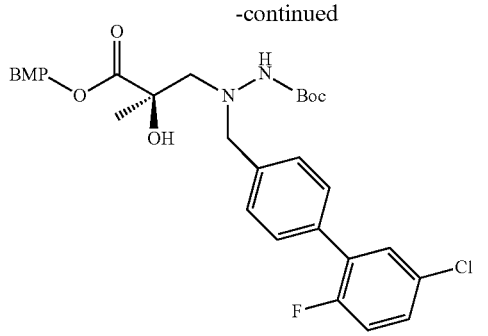

(2)

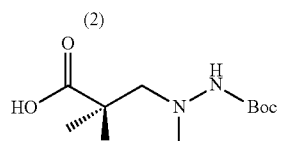

(3)

To a solution of compound 1 (15.6 g, 45 mmol) in isopropyl alcohol (240 mL) was added (R)-4-methoxybenzyl 2-methyloxirane-2-carboxylate (10 g, 45 mmol) under nitrogen. The mixture was stirred at reflux for 4 days, then cooled to room temperature. The mixture was concentrated and the residue was purified by silica gel chromatography (hexanes/EtOAc, 3:1) to yield compound 2 (18 g) as a white solid. LC-MS: [M+H]$^+$: 573; [M−tBu+H]$^+$: 517.

To a stirred solution of compound 2 (34 g, 59.3 mmol) in EtOH (300 mL) was added LiOH.H$_2$O (3 g, 71.2 mmol). The mixture was stirred at 55° C. for 3 hours, then cooled to room temperature. The mixture was concentrated, diluted with water (300 mL), and washed with EtOAc (3×100 mL). The aqueous solution was acidified with 1N HCl to pH=3, then extracted with EtOAc (3×150 mL). The combined organic layers were washed with saturated aqueous NaCl (150 mL), dried over anhydrous Na$_2$SO$_4$, and concentrated under vacuum to yield compound 3 (22.8 g) as a white solid. LC-MS: [M+Na]$^+$: 475.

(3) →

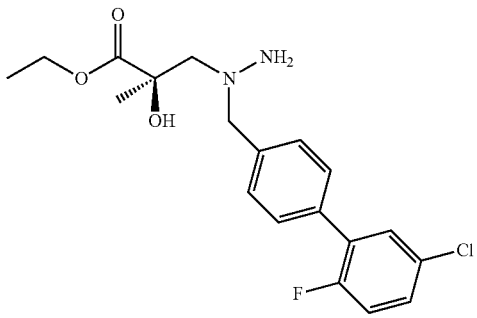

Compound 3 (22.8 g, 50.3 mmol) was dissolved in HCl/EtOH (1M, 250 mL), and the mixture was stirred overnight at room temperature. The resulting mixture was neutralized with aqueous Na$_2$CO$_3$ (2N) to pH=7, which was then concentrated under vacuum and extracted with EtOAc (3×100 mL). The combined organic layers were acidified with 1N HCl to pH=4-5, then extracted with water (3×100 mL). The combined aqueous layers were washed with EtOAc (3×50 mL) and concentrated to yield the title compound (8.7 g) as a white solid HCl salt. LC-MS: [M+H]$^+$: 381. $^1$H NMR: (CD$_3$OD) 1.103 (t, J=7.2 Hz, 3H), 1.406 (s, 3H), 2.941 (d, J=14.1 Hz, 1H), 3.293 (d, J=14.1 Hz, 1H), 3.908-3.980 (m, 2H), 4.148-4.886 (m, 2H), 7.205-7.268 (m, 1H), 7.374-7.615 (m, 6H).

Example 6

A. (R)-3-[N-(5'-Chloro-2'-fluorobiphenyl-4-ylmethyl)-N'-(3-hydroxy-isoxazole-5-carbonyl)-hydrazino]-2-hydroxy-2-methyl-propionic acid

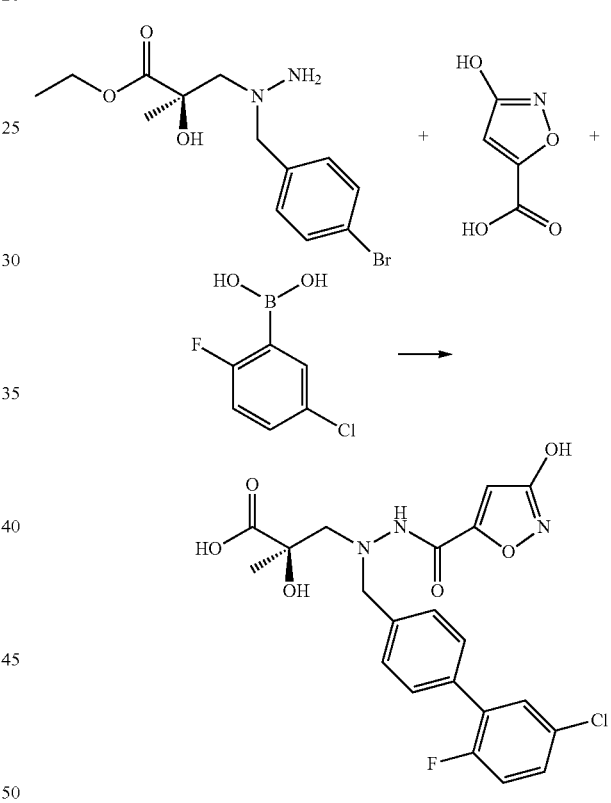

3-Hydroxyisoxazole-5-carboxylic acid (23.3 mg, 181 μmol) and HATU (68.9 mg, 181 μmol) were combined in DMF (1 mL), and the resulting mixture was stirred for 5 minutes at room temperature. DIPEA (66 μL, 377 μmol) and (R)-3-[N-(4-bromo-benzyl)-hydrazino]-2-hydroxy-2-methyl-propionic acid ethyl ester (50 mg, 0.2 mmol) were added and the resulting mixture was stirred for 20 minutes. The mixture was the evaporated under reduced pressure, then combined with 5-chloro-2-fluorophenylboronic acid (47.4 mg, 272 μmol), K$_2$CO$_3$ (62.6 mg, 453 μmol), EtOH (0.7 mL, 10 mmol), and water (0.2 mL). SilicaCat®DPP-Pd (0.28 mmol/g loading; 53.9 mg, 15 μmol) was added and the resulting mixture was microwaved at 120° C. for 10 minutes. The mixture was filtered, and 1 M aqueous LiOH (604 μL, 604 μmol) was added. The mixture was stirred for 1 hour, then concentrated and purified by preparative HPLC to yield the title compound (33 mg, 94% purity). MS m/z [M+H]+ calc'd for $C_{21}H_{19}ClFN_3O_6$, 464.09; found 464.1.

B. (R)-3-[N-(5'-Chloro-2'-fluorobiphenyl-4-ylm-ethyl)-N'-(3-hydroxy-isoxazole-5-carbonyl)-hydrazino]-2-hydroxy-2-methyl-propionic acid ethyl ester

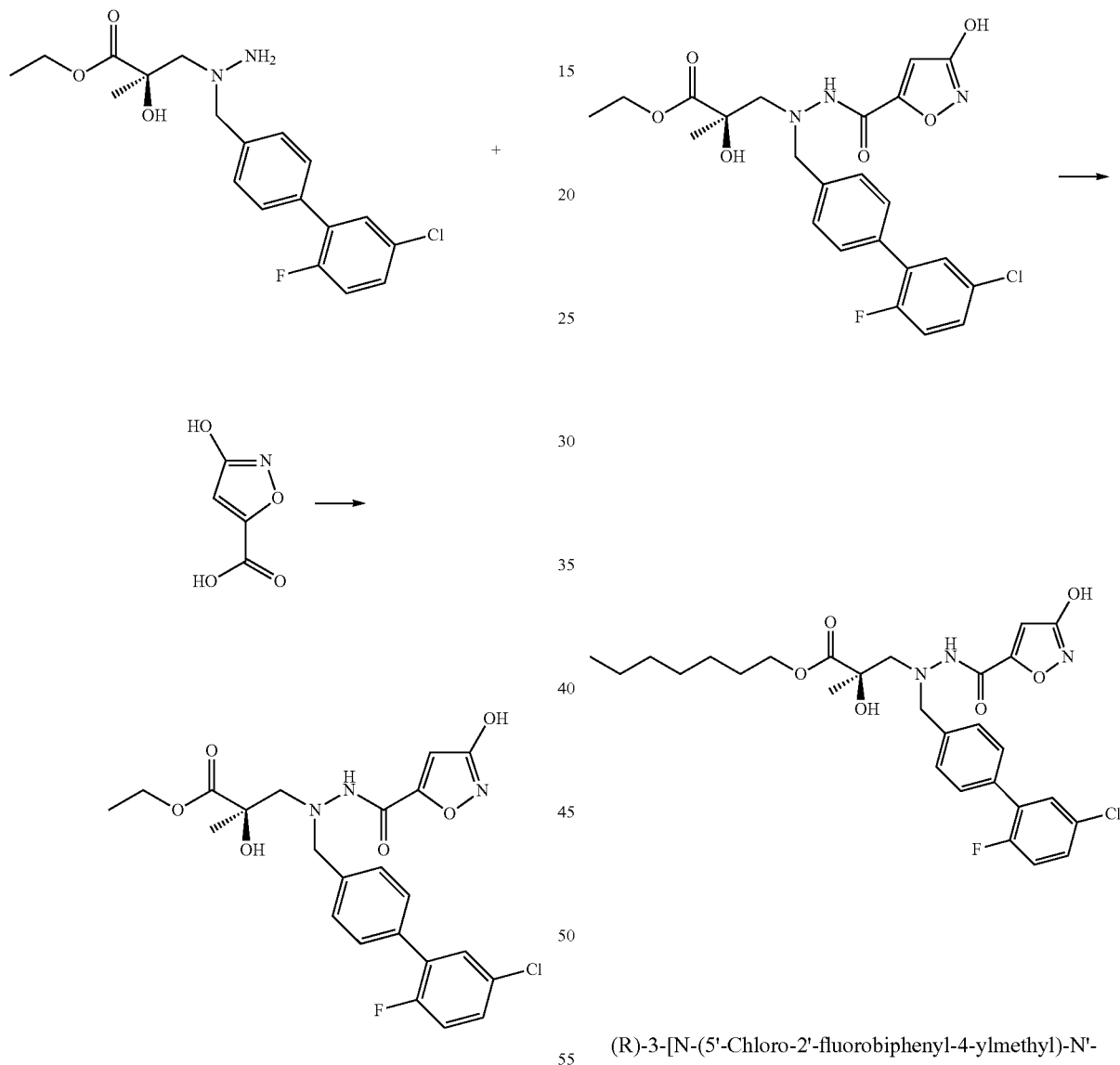

3-Hydroxyisoxazole-5-carboxylic acid (132 mg, 1.0 mmol) and HATU (389 mg, 1.0 mmol) were combined in DMF (3.7 mL), and the resulting mixture was stirred for 10 minutes at room temperature. DIPEA (343 µL, 2.0 mmol) and (R)-3-[N-(5'-chloro-2'-fluorobiphenyl-4-ylmethyl)-hydrazino]-2-hydroxy-2-methyl-propionic acid ethyl ester (300 mg, 0.8 mmol) were added and the resulting mixture was stirred for 30 minutes. LC/MS showed desired product. The mixture was the evaporated under reduced pressure to yield the title compound (210 mg, 100% purity). MS m/z [M+H]+ calc'd for $C_{23}H_{23}ClFN_3O_6$, 492.13; found 492.2.

C. (R)-3-[N-(5'-Chloro-2'-fluorobiphenyl-4-ylm-ethyl)-N'-(3-hydroxy-isoxazole-5-carbonyl)-hydrazino]-2-hydroxy-2-methyl-propionic acid heptyl ester (R)-3-[N-(5'-Chloro-2'-fluorobiphenyl-4-ylmethyl)-N'-(3-hydroxy-isoxazole-5-carbonyl)-hydrazino]-2-hydroxy-2-methyl-propionic acid ethyl ester (100 mg, 0.2 mmol) was dissolved in 1-heptanol (6 g, 50 mmol), followed by the addition of 4 M HCl in dioxane (1 mL, 4 mmol). The resulting mixture was stirred at room temperature for 8 hours, then evaporated under reduced pressure and purified (Interchim reverse phase chromatography column). The pure fractions were lyophilized to yield the title compound (27 mg, 95% purity). MS m/z [M+H]+ calc'd for $C_{28}H_{33}ClFN_3O_6$, 562.20; found 562.2.

D. (R)-3-[N-(5'-Chloro-2'-fluorobiphenyl-4-ylmethyl)-N'-(3-hydroxy-isoxazole-5-carbonyl)-hydrazino]-2-hydroxy-2-methyl-propionic acid isobutyl ester

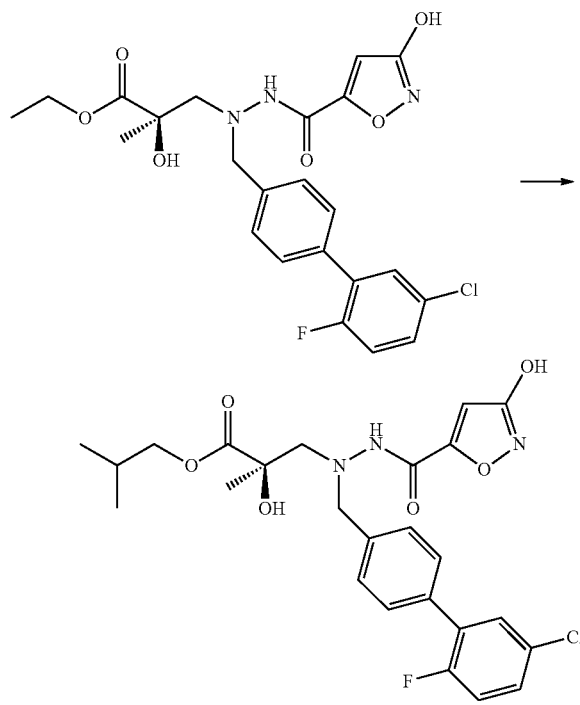

(R)-3-[N-(5'-Chloro-2'-fluorobiphenyl-4-ylmethyl)-N'-(3-hydroxy-isoxazole-5-carbonyl)-hydrazino]-2-hydroxy-2-methyl-propionic acid ethyl ester (100 mg, 0.2 mmol) was dissolved in isobutyl alcohol (6 mL, 60 mmol), followed by the addition of 4 M HCl in dioxane (1 mL, 4 mmol). The resulting mixture was stirred at room temperature for 8 hours, then evaporated under reduced pressure and purified by preparative HPLC. The clean fractions were combined and lyophilized to yield the title compound (52 mg, 100% purity). MS m/z [M+H]$^+$ calc'd for $C_{25}H_{27}ClFN_3O_6$, 520.16; found 520.2.

Example 7

Following the procedures described in the examples herein, and substituting the appropriate starting materials and reagents, compounds having formula IIIb-2, were also prepared:

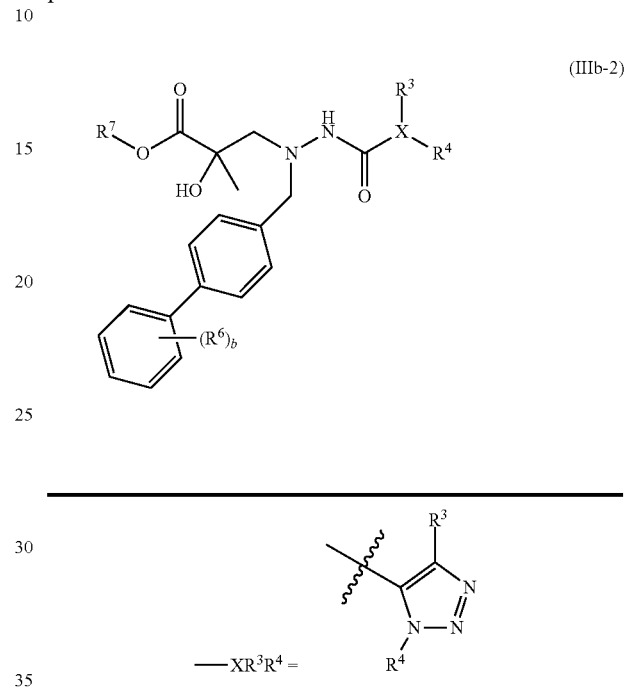

(IIIb-2)

—$XR^3R^4$ = (triazole structure with $R^3$, $R^4$)

| Ex. | $R^1$ | $R^3$ | $R^4$ | b | $R^6$ | Formula | MS m/z: [M + H]$^+$ calcd | found |
|---|---|---|---|---|---|---|---|---|
| 1 | H | H | H | 1 | 3'-Cl | $C_{20}H_{20}ClN_5O_4$ | 430.12 | 430.4 |

1. (R)-3-[N-(3'-Chlorobiphenyl-4-ylmethyl)-N'-(3H-[1,2,3]triazole-4-carbonyl)-hydrazino]-2-hydroxy-2-methyl-propionic acid —$XR^3R^4$ = (triazole structure with $R^3$, $R^4$)

| Ex. | $R^1$ | $R^3$ | $R^4$ | b | $R^6$ | Formula | MS m/z: [M + H]$^+$ calcd | found |
|---|---|---|---|---|---|---|---|---|
| 2 | H | H | —OH | 2 | 3'-Cl | $C_{20}H_{20}ClN_5O_5$ | 446.12 | 446.4 |
| 3 | H | H | —OH | 2 | 2'-F, 5'-Cl | $C_{20}H_{19}ClFN_5O_5$ | 464.11 | 464.2 |
| 4 | —(CH$_2$)$_6$—CH$_3$ | H | —OH | 2 | 2'-F, 5'-Cl | $C_{27}H_{33}ClFN_5O_5$ | 562.22 | 563.1 |
| 5 | —CH—(CH$_3$)$_2$ | H | —OH | 2 | 2'-F, 5'-Cl | $C_{23}H_{25}ClFN_5O_5$ | 506.15 | 506.3 |
| 6 | —CH$_2$—CH—(CH$_3$)$_2$ | H | —OH | 2 | 2'-F, 5'-Cl | $C_{24}H_{27}ClFN_5O_5$ | 520.17 | 520.3 |
| 7 | —CH$_2$—CH$_3$ | H | —OH | 2 | 2'-F, 5'-Cl | $C_{22}H_{23}ClFN_5O_5$ | 492.14 | 492.3 |

2. (R)-3-[N-(3'-Chlorobiphenyl-4-ylmethyl)-N'-(1-hydroxy-1H-[1,2,3]triazole-4-carbonyl)-hydrazino]-2-hydroxy-2-methyl-propionic acid
3. (R)-3-[N-(5'-Chloro-2'-fluorobiphenyl-4-ylmethyl)-N'-(1-hydroxy-1H-[1,2,3]triazole-4-carbonyl)-hydrazino]-2-hydroxy-2-methyl-propionic acid
4. (R)-3-[N-(5'-Chloro-2'-fluorobiphenyl-4-ylmethyl)-N'-(1-hydroxy-1H-[1,2,3]triazole-4-carbonyl)-hydrazino]-2-hydroxy-2-methyl-propionic acid heptyl ester
5. (R)-3-[N-(5'-Chloro-2'-fluorobiphenyl-4-ylmethyl)-N'-(1-hydroxy-1H-[1,2,3]triazole-4-carbonyl)-hydrazino]-2-hydroxy-2-methyl-propionic acid isopropyl ester
6. (R)-3-[N-(5'-Chloro-2'-fluorobiphenyl-4-ylmethyl)-N'-(1-hydroxy-1H-[1,2,3]triazole-4-carbonyl)-hydrazino]-2-hydroxy-2-methyl-propionic acid isobutyl ester
7. (R)-3-[N-(5'-Chloro-2'-fluorobiphenyl-4-ylmethyl)-N'-(1-hydroxy-1H-[1,2,3]triazole-4-carbonyl)-hydrazino]-2-hydroxy-2-methyl-propionic acid ethyl ester

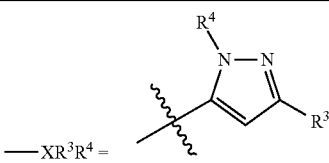

—XR³R⁴ =

| Ex. | R¹ | R³ | R⁴ | b | R⁶ | Formula | MS m/z: [M + H]⁺ calcd | found |
|---|---|---|---|---|---|---|---|---|
| 8 | H | 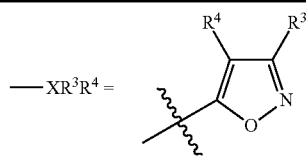 | H | 1 | 3'-Cl | $C_{25}H_{23}ClN_6O_4$ | 507.15 | 507.2 |
| 9 | H | —C(O)—N(CH₃)₂ | H | 1 | 3'-Cl | $C_{24}H_{26}ClN_5O_5$ | 500.16 | 500.2 |
| 10 | H | —COOH | H | 1 | 3'-Cl | $C_{22}H_{21}ClN_4O_6$ | 473.12 | 473.4 |

8. (R)-3-[N-(3'-Chlorobiphenyl-4-ylmethyl)-N'-(5-pyrazin-2-yl-2H-pyrazole-3-carbonyl)-hydrazino]-2-hydroxy-2-methyl-propionic acid
9. (R)-3-[N-(3'-Chlorobiphenyl-4-ylmethyl)-N'-(5-dimethylcarbamoyl-2H-pyrazole-3-carbonyl)-hydrazino]-2-hydroxy-2-methyl-propionic acid
10. 5-[N'-((R)-2-Carboxy-2-hydroxy-propyl)-N'-(3'-chlorobiphenyl-4-ylmethyl)-hydrazinocarbonyl]-1H-pyrazole-3-carboxylic acid

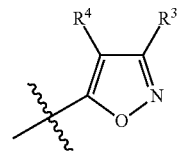

—XR³R⁴ =

| Ex. | R¹ | R³ | R⁴ | b | R⁶ | Formula | MS m/z: [M + H]⁺ calcd | found |
|---|---|---|---|---|---|---|---|---|
| 11 | H | —OH | H | 1 | 3'-Cl | $C_{21}H_{20}ClN_3O_6$ | 446.10 | 446.4 |
| 12 | H | —OH | H | 2 | 2'-CH₃, 5'-Cl | $C_{22}H_{22}ClN_3O_6$ | 460.12 | 460.0 |
| 13 | H | —OH | H | 2 | 3',5'-diCl | $C_{21}H_{19}Cl_2N_3O_6$ | 480.07 | 481.1 |
| 14 | H | —OH | H | 1 | 2'-OCH₃ | $C_{22}H_{23}N_3O_7$ | 442.15 | 442.2 |
| 15 | H | —OH | H | 1 | 2'-Cl | $C_{21}H_{20}ClN_3O_6$ | 446.10 | 446.0 |
| 16 | H | —OH | H | 1 | 2'-OH | $C_{21}H_{21}N_3O_7$ | 428.14 | 428.2 |
| 17 | H | —OH | H | 1 | 2'-F | $C_{21}H_{20}FN_3O_6$ | 430.13 | 430.2 |
| 18 | H | —OH | H | 2 | 2',5'-diF | $C_{21}H_{19}F_2N_3O_6$ | 448.12 | 448.2 |
| 19 | H | —OH | H | 2 | 2',5'-diCl | $C_{21}H_{19}Cl_2N_3O_6$ | 480.07 | 480.0 |
| 20 | H | —OH | H | 1 | 3'-F | $C_{21}H_{20}FN_3O_6$ | 430.13 | 430.2 |

11. (R)-3-[N-(3'-Chlorobiphenyl-4-ylmethyl)-N'-(3-hydroxy-isoxazole-5-carbonyl)-hydrazino]-2-hydroxy-2-methyl-propionic acid
12. (R)-3-[N-(5'-Chloro-2'-methyl-biphenyl-4-ylmethyl)-N'-(3-hydroxy-isoxazole-5-carbonyl)-hydrazino]-2-hydroxy-2-methyl-propionic acid
13. (R)-3-[N-(3',5'-Dichlorobiphenyl-4-ylmethyl)-N'-(3-hydroxy-isoxazole-5-carbonyl)-hydrazino]-2-hydroxy-2-methyl-propionic acid
14. (R)-2-Hydroxy-3-[N'-(3-hydroxy-isoxazole-5-carbonyl)-N-(2'-methoxy-biphenyl-4-ylmethyl)-hydrazino]-2-methyl-propionic acid
15. (R)-3-[N-(2'-Chlorobiphenyl-4-ylmethyl)-N'-(3-hydroxy-isoxazole-5-carbonyl)-hydrazino]-2-hydroxy-2-methyl-propionic acid
16. (R)-2-Hydroxy-3-[N-(2'-hydroxy-biphenyl-4-ylmethyl)-N'-(3-hydroxy-isoxazole-5-carbonyl)-hydrazino]-2-methyl-propionic acid
17. (R)-3-[N-(2'-Fluorobiphenyl-4-ylmethyl)-N'-(3-hydroxy-isoxazole-5-carbonyl)-hydrazino]-2-hydroxy-2-methyl-propionic acid
18. (R)-3-[N-(2',5'-Difluorobiphenyl-4-ylmethyl)-N'-(3-hydroxy-isoxazole-5-carbonyl)-hydrazino]-2-hydroxy-2-methyl-propionic acid
19. (R)-3-[N-(2',5'-Dichlorobiphenyl-4-ylmethyl)-N'-(3-hydroxy-isoxazole-5-carbonyl)-hydrazino]-2-hydroxy-2-methyl-propionic acid
20. (R)-3-[N-(3'-Fluorobiphenyl-4-ylmethyl)-N'-(3-hydroxy-isoxazole-5-carbonyl)-hydrazino]-2-hydroxy-2-methyl-propionic acid

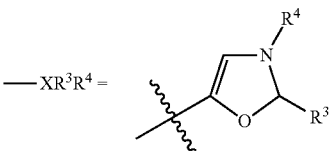

—XR³R⁴ =

| Ex. | R¹ | R³ | R⁴ | b | R⁶ | Formula | MS m/z: [M + H]⁺ calcd | found |
|---|---|---|---|---|---|---|---|---|
| 21 | H | =O | H | 1 | 3'-Cl | $C_{21}H_{20}ClN_3O_6$ | 446.10 | 446.1 |
| 22 | H | =O | H | 2 | 2'-F, 5'-Cl | $C_{21}H_{19}ClFN_3O_6$ | 464.09 | 464.0 |

21. (R)-3-[N-(3'-Chlorobiphenyl-4-ylmethyl)-N'-(2-oxo-2,3-dihydro-oxazole-5-carbonyl)-hydrazino]-2-hydroxy-2-methyl-propionic acid 22. (R)-3-[N-(5'-Chloro-2'-fluorobiphenyl-4-ylmethyl)-N'-(2-oxo-2,3-dihydro-oxazole-5-carbonyl)-hydrazino]-2-hydroxy-2-methyl-propionic acid

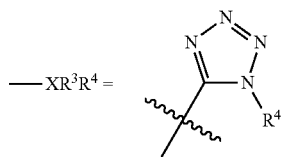

| Ex. | R¹ | R³ | R⁴ | b | R⁶ | Formula | MS m/z: [M + H]⁺ calcd | found |
|---|---|---|---|---|---|---|---|---|
| 23 | H | absent | H | 2 | 2'-F, 5'-Cl | $C_{19}H_{18}ClFN_6O_4$ | 449.11 | 449.2 |
| 24 | H | absent | H | 2 | 2'-CH₃, 5'-Cl | $C_{20}H_{21}ClN_6O_4$ | 445.13 | 445.4 |

23. (R)-3-[N-(5'-Chloro-2'-fluorobiphenyl-4-ylmethyl)-N'-(1H-tetrazole-5-carbonyl)-hydrazino]-2-hydroxy-2-methyl-propionic acid 24. (R)-3-[N-(5'-Chloro-2'-methyl-biphenyl-4-ylmethyl)-N'-(1H-tetrazole-5-carbonyl)-hydrazino]-2-hydroxy-2-methyl-propionic acid

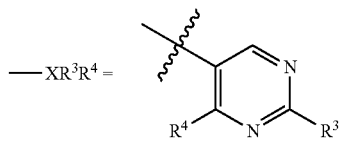

| Ex. | R¹ | R³ | R⁴ | b | R⁶ | Formula | MS m/z: [M + H]⁺ calcd | found |
|---|---|---|---|---|---|---|---|---|
| 25 | H | —OH | H | 1 | 3'-Cl | $C_{22}H_{21}ClN_4O_5$ | 457.12 | 457.2 |

25. (R)-3-[N-(3'-Chlorobiphenyl-4-ylmethyl)-N'-(2-hydroxy-pyrimidine-5-carbonyl)-hydrazino]-2-hydroxy-2-methyl-propionic acid

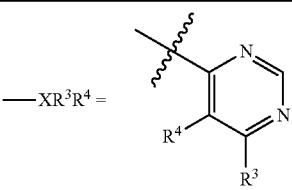

| Ex. | R¹ | R³ | R⁴ | b | R⁶ | Formula | MS m/z: [M + H]⁺ calcd | found |
|---|---|---|---|---|---|---|---|---|
| 26 | H | —COOH | H | 1 | 3'-Cl | $C_{23}H_{21}ClN_4O_6$ | 485.12 | 485.2 |

26. 6-[N'-((R)-2-Carboxy-2-hydroxy-propyl)-N'-(3'-chloro-biphenyl-4-ylmethyl)-hydrazinocarbonyl]-pyrimidine-4-carboxylic acid Preparation 8

(R)-4-Amino-5-biphenyl-4-yl-2,2-dimethyl-pentanoic Acid Ethyl Ester

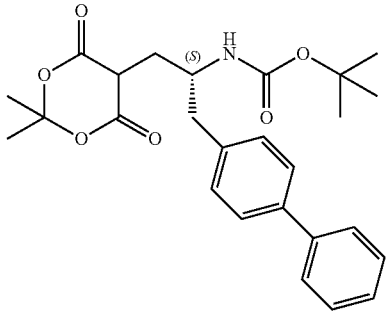

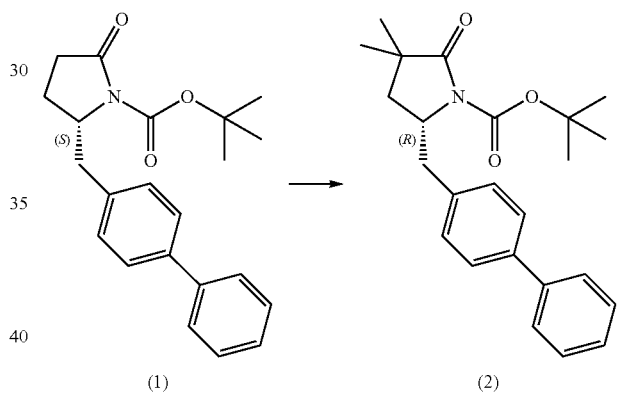

Step 1: A solution of [(S)-1-biphenyl-4-ylmethyl-2-(2,2-dimethyl-4,6-dioxo-[1,3]dioxan-5-yl)-ethyl]-carbamic acid t-butyl ester (46 g, 0.1 mol) in anhydrous toluene (300 mL) was refluxed for 3 hours under nitrogen. After evaporation of the solvent, the residue was purified by chromatography (hexanes:EtOAc=10:1) to yield compound 1 as a light yellow solid (27 g). LC-MS: [M+Na]: 374, [2M+Na]: 725.

Step 2: To a solution of compound 1 (6.2 g, 17.6 mmol) in anhydrous THF (100 mL) was added a solution of LiHMDS in THF (39 mL, 39 mmol) at −78° C. under nitrogen. The mixture was stirred at −78° C. for 2 hours, and then methyl iodide (7.5 g, 53 mmol) was added. After stirring for 0.5 hour at −78° C., the mixture was warmed to room temperature and stirred at room temperature for 3 hours. After the mixture cooled to −10° C., the reaction was quenched with saturated aqueous NH₄Cl (100 mL) and extracted with EtOAc (100 mL×4). The combined organic layers were washed with saturated aqueous NaCl (300 mL), dried over MgSO₄, filtered, and concentrated to yield the crude product which was further purified by chromatography (hexanes:EtOAc=10:1) to yield compound 2 as a light yellow solid (5.7 g). LC-MS: [M+Na]: 402, [2M+Na]: 781.

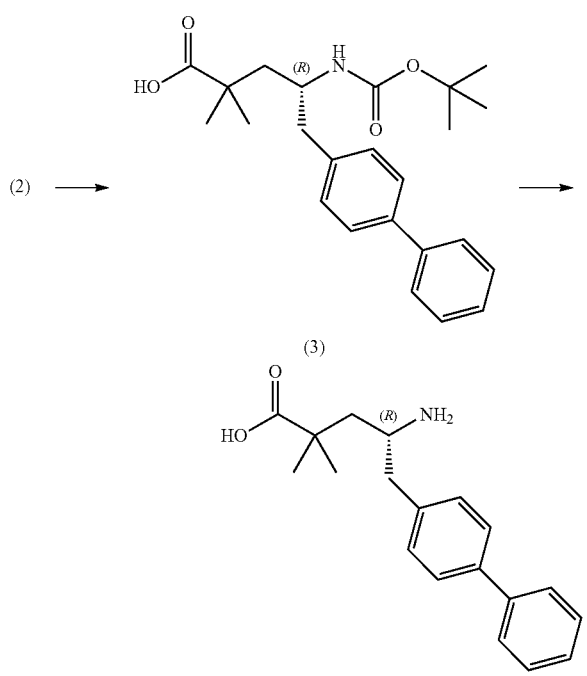

Step 3: To a solution of compound 2 (5.7 g, 15 mmol) in acetone (120 mL) was added 1 M NaOH (60 mL, 60 mmol) at −5° C. under nitrogen. The mixture was warmed to room temperature and stirred at room temperature for 20 hours. The mixture was concentrated and the residue was diluted with water (250 mL) and washed with EtOAc (150 mL). The pH of the aqueous layer was adjusted to 2 with 6 M HCl at 0° C., and the solid was filtrated and dried in vacuo to yield the crude compound 3 as a white solid (5 g). LC-MS: [M+Na]: 420, [2M+Na]: 817.

Step 4: To a solution of crude compound 3 (5 g, 12.7 mmol) in anhydrous EtOH (300 mL) was added $SOCl_2$ (13.4 mL, 190 mmol) at −30° C. under nitrogen. The mixture was warmed to room temperature and stirred for 20 hours at room temperature. The mixture was concentrated, and the residue was washed with anhydrous $Et_2O$ to yield the title compound as a white solid HCl salt (3.7 g). LC-MS: [M+H]: 326, [2M+H]: 651. $^1$H NMR (300 MHz, DMSO): δ7.86 (s, 3H), 7.67-7.64 (m, 4H), 7.49-7.33 (m, 5H), 4.09-3.97 (m, 2H), 3.42 (m, 1H), 2.90-2.80 (m, 2H), 1.88-1.84 (m, 2H), 1.17-1.12 (m, 9H).

Example 8

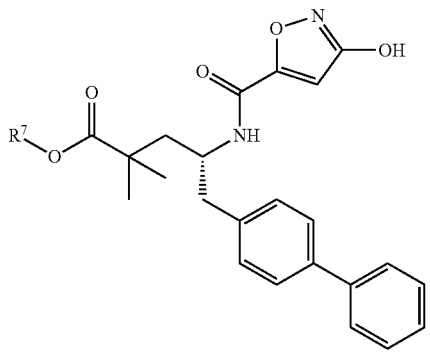

A. (R)-5-Biphenyl-4-yl-4-[(3-hydroxy-isoxazole-5-carbonyl)-amino]-2,2-dimethyl-pentanoic acid ($R^7$═H)

3-Hydroxyisoxazole-5-carboxylic acid (396 mg, 307 μmol, 1.0 eq.), EDCI (54.4 μL, 307 μmol, 1.0 eq.) and HOBt (41.5 mg, 307 μmol, 1.0 eq.) were combined in DMF (0.2 mL) and stirred for 5 minutes at room temperature. (R)-4-Amino-5-biphenyl-4-yl-2,2-dimethyl-pentanoic acid ethyl ester (100 mg, 307 μmmol, 1.0 eq.) was added and the resulting mixture was stirred for 30 minutes. 1 M LiOH in water (1.2 mL) in THF (3 mL) was added and the mixture was maintained at 60° C. for 2 days. A small amount of MeOH was added to speed up the reaction. The reaction was then quenched with AcOH and the product was purified by preparative HPLC to yield the title compound (25 mg, 95% purity. MS m/z [M+H]$^+$ calc'd for $C_{23}H_{24}N_2O_5$, 409.17; found 409.4.

B. (R)-5-Biphenyl-4-yl-4-[(3-hydroxy-isoxazole-5-carbonyl)-amino]-2,2-dimethyl-pentanoic acid ethyl ester ($R^7$═CH$_2$CH$_2$)

(R)-4-Amino-5-biphenyl-4-yl-2,2-dimethyl-pentanoic acid ethyl ester (72.1 mg, 221 μmol, 1.0 eq.), 1-butanol (5 mL) and 4 M of HCl in 1,4-dioxane (2 mL) were combined and stirred at 65° C. overnight. To this was added a mixture of 3-hydroxyisoxazole-5-carboxylic acid (28.6 mg, 221 μmol, 1.0 eq.), EDCI (39.2 μL, 221 μmol, 1.0 eq.) and HOBt (29.9 mg, 221 μmol, 1.0 eq.) that had been combined in DMF (0.2 mL) and stirred for 5 minutes at room temperature. The resulting mixture was stirred for 30 minutes. The reaction was then quenched with AcOH and the product was purified by preparative HPLC to yield the title compound (50 mg, 95% purity). MS m/z [M+H]$^+$ calc'd for $C_{25}H_{28}H_2O_5$, 437.20; found 437.4.

C. (R)-5-Biphenyl-4-yl-4-[(3-hydroxy-isoxazole-5-carbonyl)-amino]-2,2-dimethyl-pentanoic acid butyl ester ($R^7$═(CH$_2$)$_3$CH$_3$)

(R)-4-Amino-5-biphenyl-4-yl-2,2-dimethyl-pentanoic acid ethyl ester (72.1 mg, 221 μmol, 1.0 eq.) was combined with dry butyl alcohol (5 mL) and 4N HCl in dioxane (1 mL) and stirred at 60° C. overnight. The solvent where evaporated and azeotroped with toluene. To this was added a mixture of 3-Hydroxyisoxazole-5-carboxylic acid (28.6 mg, 221 μmol, 1.0 eq.), EDCI (39.2 μL, 1.0 eq.) and HOBt (29.9 mg, 221 μmol, 1.0 eq.) that had been combined in DMF (0.2 mL) and stirred for 5 minutes at room temperature. The resulting mixture was stirred for 30 minutes. The reaction was quenched with AcOH and the product was purified by preparative HPLC and lyophilized to yield the title compound (40 mg, 95% purity). MS m/z [M+H]$^+$ calc'd for $C_{27}H_{32}N_2O_5$, 465.23; found 465.4.

Example 9

Following the procedures described in the examples herein, and substituting the appropriate starting materials and reagents, compounds having formula IVa-1, were also prepared:

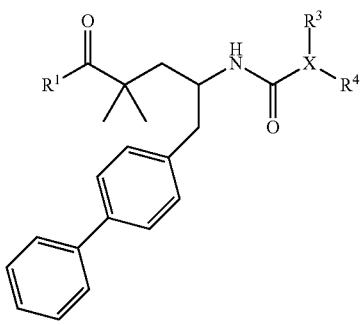

(IVa-1)

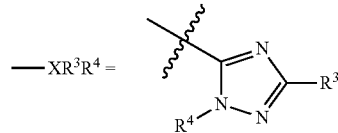

| Ex. | R¹ | R³ | R⁴ | Formula | MS m/z: [M + H]⁺ calcd | found |
|---|---|---|---|---|---|---|
| 3 | —OH | —OH | H | $C_{22}H_{24}N_4O_4$ | 409.18 | 409.4 |
| 4 | —OH | H | H | $C_{22}H_{24}N_4O_3$ | 393.19 | 393.2 |

3. (R)-5-Biphenyl-4-yl-4-[(5-hydroxy-2H-[1,2,4]triazole-3-carbonyl)-amino]-2,2-dimethyl-pentanoic acid
4. (R)-5-Biphenyl-4-yl-2,2-dimethyl-4-[(2H-[1,2,4]triazole-3-carbonyl)-amino]-pentanoic acid

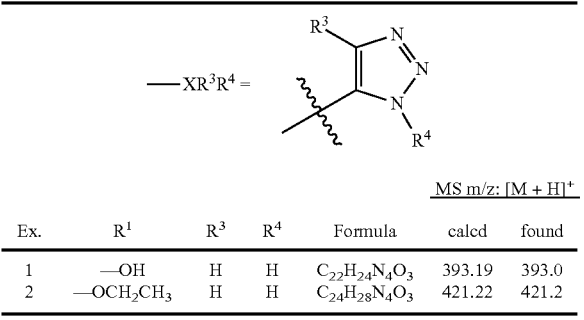

| Ex. | R¹ | R³ | R⁴ | Formula | MS m/z: [M + H]⁺ calcd | found |
|---|---|---|---|---|---|---|
| 1 | —OH | H | H | $C_{22}H_{24}N_4O_3$ | 393.19 | 393.0 |
| 2 | —OCH₂CH₃ | H | H | $C_{24}H_{28}N_4O_3$ | 421.22 | 421.2 |

1. (R)-5-Biphenyl-4-yl-2,2-dimethyl-4-[(3H-[1,2,3]triazole-4-carbonyl)-amino]-pentanoic acid
2. (R)-5-Biphenyl-4-yl-2,2-dimethyl-4-[(3H-[1,2,3]triazole-4-carbonyl)-amino]-pentanoic acid ethyl ester

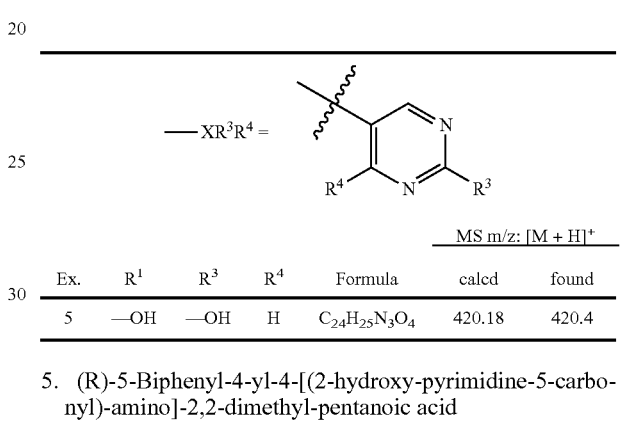

| Ex. | R¹ | R³ | R⁴ | Formula | MS m/z: [M + H]⁺ calcd | found |
|---|---|---|---|---|---|---|
| 5 | —OH | —OH | H | $C_{24}H_{25}N_3O_4$ | 420.18 | 420.4 |

5. (R)-5-Biphenyl-4-yl-4-[(2-hydroxy-pyrimidine-5-carbonyl)-amino]-2,2-dimethyl-pentanoic acid

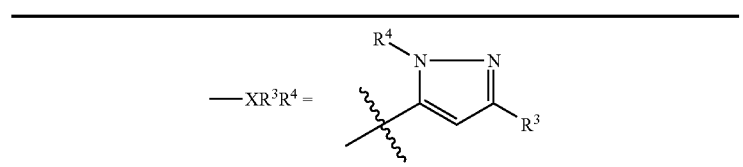

| Ex. | R¹ | R³ | R⁴ | Formula | MS m/z: [M + H]⁺ calcd | found |
|---|---|---|---|---|---|---|
| 6 | —OH | —COOH | H | $C_{24}H_{25}N_3O_5$ | 436.18 | 436.2 |
| 7 | —OCH₂CH₃ | —COOH | H | $C_{26}H_{29}N_3O_5$ | 464.21 | 464.2 |

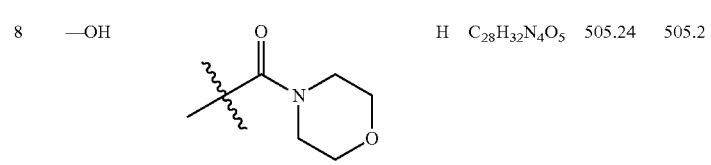

| 8 | —OH | | H | $C_{28}H_{32}N_4O_5$ | 505.24 | 505.2 |

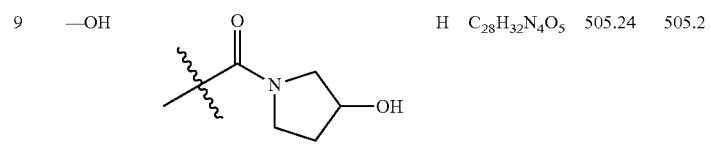

| 9 | —OH | | H | $C_{28}H_{32}N_4O_5$ | 505.24 | 505.2 |

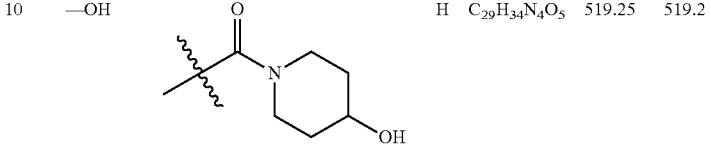

| 10 | —OH | | H | $C_{29}H_{34}N_4O_5$ | 519.25 | 519.2 |

-continued

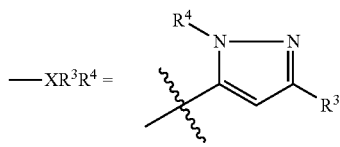

| Ex. | R¹ | R³ | R⁴ | Formula | MS m/z: [M + H]⁺ calcd | found |
|---|---|---|---|---|---|---|
| 11 | —OH | (pyrrolidine-2-carboxylic acid acyl) | H | $C_{29}H_{32}N_4O_6$ | 533.23 | 533.2 |
| 12 | —OH | —C(O)—NH(CH₃) | H | $C_{25}H_{28}N_4O_4$ | 449.21 | 449.2 |
| 13 | —OH | —C(O)N(CH₃)₂ | H | $C_{26}H_{30}N_4O_4$ | 463.23 | 463.2 |
| 14 | —OH | —C(O)N(CH₃)—CH₂—CH(CH₃)₂ | H | $C_{29}H_{36}N_4O_4$ | 505.27 | 505.2 |
| 15 | —OH | —C(O)N(CH₃)—(CH₂)₂OCH₃ | H | $C_{28}H_{34}N_4O_5$ | 507.25 | 507.2 |
| 16 | —OCH₂CH₃ | —C(O)N(CH₃)—(CH₂)₂OCH₃ | H | $C_{30}H_{38}N_4O_5$ | 535.28 | 535.2 |
| 17 | —OH | —C(O)NH—(CH₂)₂-imidazole | H | $C_{29}H_{32}N_6O_4$ | 529.25 | 529.2 |
| 18 | —OH | —COCH₃ | H | $C_{25}H_{27}N_3O_4$ | 434.20 | 434.2 |

6. 5-((R)-1-Biphenyl-4-ylmethyl-3-carboxy-3-methyl-butyl-carbamoyl)-1H-pyrazole-3-carboxylic acid 7. 5-((R)-1-Biphenyl-4-ylmethyl-3-ethoxycarbonyl-3-methyl-butylcarbamoyl)-1H-pyrazole-3-carboxylic acid 8. (R)-5-Biphenyl-4-yl-2,2-dimethyl-4-{[5-(morpholine-4-carbonyl)-2H-pyrazole-3-carbonyl]-amino}-pentanoic acid 9. (R)-5-Biphenyl-4-yl-4-{[5-(3-hydroxy-pyrrolidine-1-carbonyl)-2H-pyrazole-3-carbonyl]-amino}-2,2-dimethyl-pentanoic acid 10. (R)-5-Biphenyl-4-yl-4-{[5-(4-hydroxy-piperidine-1-carbonyl)-2H-pyrazole-3-carbonyl]-amino}-2,2-dimethyl-pentanoic acid 11. (S)-1-[5-((R)-1-Biphenyl-4-ylmethyl-3-carboxy-3-methyl-butylcarbamoyl)-1H-pyrazole-3-carbonyl]-pyrrolidine-2-carboxylic acid 12. (R)-5-Biphenyl-4-yl-2,2-dimethyl-4-[(5-methylcarbamoyl-2H-pyrazole-3-carbonyl)-amino]-pentanoic acid 13. (R)-5-Biphenyl-4-yl-4-[(5-dimethylcarbamoyl-2H-pyrazole-3-carbonyl)-amino]-2,2-dimethyl-pentanoic acid 14. (R)-5-Biphenyl-4-yl-4-{[5-(isobutyl-methyl-carbamoyl)-2H-pyrazole-3-carbonyl]-amino}-2,2-dimethyl-pentanoic acid 15. (R)-5-Biphenyl-4-yl-4-({5-[(2-methoxy-ethyl)-methyl-carbamoyl]-2H-pyrazole-3-carbonyl}-amino)-2,2-dimethyl-pentanoic acid 16. (R)-5-Biphenyl-4-yl-4-({5-[(2-methoxy-ethyl)-methyl-carbamoyl]-2H-pyrazole-3-carbonyl}-amino)-2,2-dimethyl-pentanoic acid ethyl ester 17. (R)-5-Biphenyl-4-yl-4-({5-[2-(1H-imidazol-4-yl)-ethyl-carbamoyl]-2H-pyrazole-3-carbonyl}-amino)-2,2-dimethyl-pentanoic acid 18. (R)-4-[(5-Acetyl-2H-pyrazole-3-carbonyl)-amino]-5-biphenyl-4-yl-2,2-dimethyl-pentanoic acid Preparation 9

1-((R)-2-Amino-3-biphenyl-4-yl-propyl)-cyclopropanecarboxylic Acid

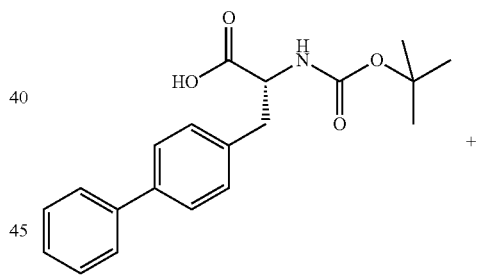

(1)

Into a flask containing BOC-D-4,4'-biphenylalanine (11.3 g, 33.1 mmol, 1.0 eq.), 4-dimethylaminopyridine (6.5 g, 53.0 mmol, 1.6 eq.), 2,2-dimethyl-1,3-dioxane-4,6-dione (5.3 g, 36.4 mmol, 1.1 eq.) in DCM (100 mL) was added 1 M of DCC in DCM (38.1 mL) at 0° C. over 30 minutes. The mixture was maintained at 0° C. for 6 hours and the resulting precipitate was filtered off. The filtrate was washed with aqueous 10% $KHSO_4$ (2×50 mL) then dried. The solution was acidified with AcOH (20 mL) at 0° C. and sodium borohydride (3.1 g, 82.7 mmol, 2.5 eq.) was added over 30 minutes in 3 portions. The mixture was maintained at 0° C. for 3 hours, washed with water and dried, then concentrated under vacuum. The crude material was purified by chromatography (0-40% EtOAc/hexanes gradient). Eschenmoser's salt (15.9 g, 86.0 mmol) in t-butyl alcohol (70 mL) was added and the resulting mixture was stirred at 65° C. overnight. The mixture was concentrated and $Et_2O$ (10 mL) was added. The organic solution was then washed with saturated aqueous $NaHCO_3$ (10 mL) and 10% $KHSO_4$ (10 mL). The organic solution was dried over $Na_2SO_4$ and concentrated. The crude product was purified by chromatography (0-40% EtOAc/hexanes gradient) to yield compound 1 (3.3 g).

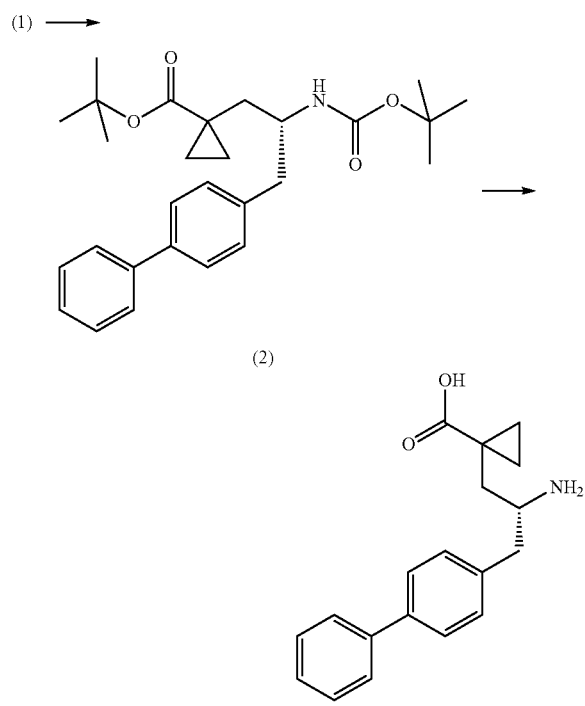

Trimethylsufoxonium iodide (2.0 g, 9.2 mmol, 1.0 eq.) in dimethyl sulfoxide (50 mL) was combined with NaH (366 mg, 9.2 mmol, 1.1 eq.) and stirred for 15 minutes at room temperature. To this was added compound 1 (3.6 g, 8.3 mmol, 1.0 eq) dissolved dimethyl sulfoxide (50 mL). The resulting mixture was stirred at room temperature overnight. The solution was mixed with saturated aqueous NaCl (50 mL) and extracted with EtOAc (3×10 mL), and the organic layer was washed with saturated aqueous NaCl (2×50 mL) and dried over anhydrous $Na_2SO_4$. After evaporation of the solvent, the crude reaction was purified by chromatography (0-40% EtOAc/hexanes gradient) to yield compound 2,1-((R)-3-biphenyl-4-yl-2-t-butoxycarbonylaminopropyl)cyclopropanecarboxylic acid t-butyl ester. TFA (200 µL) and DCM (500 µL) were added and the resulting mixture was stirred for 30 minutes. The solvent was evaporated under vacuum and azeotroped with toluene (2×) to obtain the title compound.

Example 10

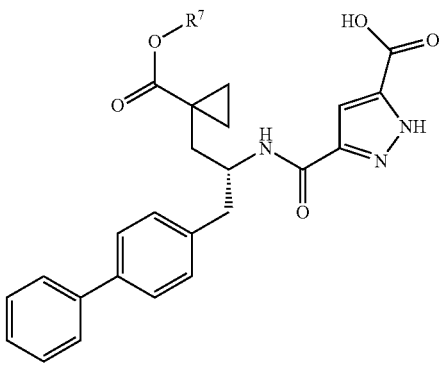

A. 5-[(R)-2-Biphenyl-4-yl-1-(1-carboxy-cyclopropylmethyl)-ethylcarbamoyl]-2H-pyrazole-3-carboxylic acid ($R^7$=H)

3,5-Pyrazoledicarboxylic acid (35.2 mg, 226 µmol, 1.0 eq.), DIPEA (126 µL) and HATU (85.9 mg, 226 µmol, 1.0 eq.) and DCM (5 mL) were combined and stirred for 5 minutes at room temperature. 1-((R)-2-Amino-3-biphenyl-4-yl-propyl)-cyclopropanecarboxylic acid (86.7 mg, 294 µmol, 2.3 eq,) and DIPEA (0.5 mL) in DCM (5 mL) was added, and the resulting mixture was stirred for 1 hour. The reaction was quenched with saturated aqueous $NH_4Cl$ and the product was extracted with DCM, dried and evaporated. The resulting product was combined with AcOH (1.5 mL) and purified with preparative HPLC to yield the title compound (21.4 mg; 93% purity). MS m/z [M+H]$^+$ calc'd for $C_{24}H_{23}N_3O_5$, 434.16; found 433.5.

B. 5-[(R)-1-Biphenyl-4-ylmethyl-2-(1-butoxycarbonyl-cyclopropyl)-ethylcarbamoyl]-1H-pyrazole-3-carboxylic acid ($R^7$=—$(CH_2)_3CH_2$)

1-((R)-3-Biphenyl-4-yl-2-t-butoxycarbonylaminopropyl) cyclopropanecarboxylic acid t-butyl ester (1.0 g, 2.2 mmol, 1.0 eq.), 1-butanol (5 mL) and 4 M of HCl in 1,4-dioxane (2 mL) were combined and stirred at 65° C. overnight. To this was added a mixture of 3,5-pyrazoledicarboxylic acid (34.6 µg, 221 µmol, 1.0 eq.), EDCI (39.2 µL, 221 µmol, 1.0 eq.) and HOBt (29.9 mg, 221 µmol, 1.0 eq.) that had been combined in DMF (0.2 mL) and stirred for 5 minutes at room temperature. The resulting mixture was stirred for 30 minutes. The reaction was then quenched with ACOH and the product was purified by preparative HPLC and lyophilized to yield the title compound (29 mg, 95% purity). MS m/z [M+H]$^+$ calc'd for $C_{28}H_{31}N_3O_5$, 490.23; found 490.6.

Note that as explained herein, compounds such as this can exist in a tautomer form, for example, as 5-[(R)-1-biphenyl-4-ylmethyl-2-(1-butoxycarbonyl-cyclopropyl)-ethylcarbamoyl]-2H-pyrazole-3-carboxylic acid.

Example 11

Following the procedures described in the examples herein, and substituting the appropriate starting materials and reagents, compounds having formula Va-1, were also prepared:

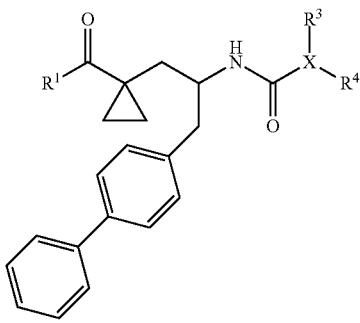

(Va-1)

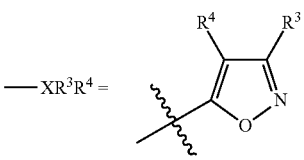

| Ex. | R¹ | R³ | R⁴ | Formula | MS m/z: [M + H]⁺ calcd | found |
|---|---|---|---|---|---|---|
| 5 | —OH | —OH | H | $C_{23}H_{22}N_2O_5$ | 407.15 | 407.4 |
| 6 | —OCH₂CH₃ | —OH | H | $C_{25}H_{26}N_2O_5$ | 435.18 | 435.4 |
| 7 | —O(CH₂)₃CH₃ | —OH | H | $C_{27}H_{30}N_2O_5$ | 463.22 | 463.4 |

5. 1-{(R)-3-Biphenyl-4-yl-2-[(3-hydroxy-isoxazole-5-carbonyl)-amino]-propyl}-cyclopropanecarboxylic acid
6. 1-{(R)-3-Biphenyl-4-yl-2-[(3-hydroxy-isoxazole-5-carbonyl)-amino]-propyl}-cyclopropanecarboxylic acid ethyl ester
7. 1-{(R)-3-Biphenyl-4-yl-2-[(3-hydroxy-isoxazole-5-carbonyl)-amino]-propyl}-cyclopropanecarboxylic acid butyl ester

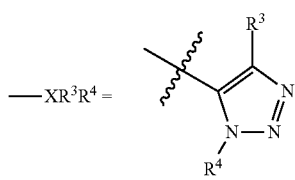

| Ex. | R¹ | R³ | R⁴ | Formula | MS m/z: [M + H]⁺ calcd | found |
|---|---|---|---|---|---|---|
| 1 | —OH | H | H | $C_{22}H_{22}N_4O_3$ | 391.17 | 391.4 |
| 2 | —OCH₂CH₃ | H | H | $C_{24}H_{26}N_4O_3$ | 419.20 | 419.2 |

1. 1-{(R)-3-Biphenyl-4-yl-2-[(3H-[1,2,3]triazole-4-carbonyl)-amino]-propyl}-cyclopropanecarboxylic acid
2. 1-{(R)-3-Biphenyl-4-yl-2-[(3H-[1,2,3]triazole-4-carbonyl)-amino]-propyl}-cyclopropanecarboxylic acid ethyl ester

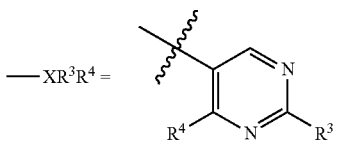

| Ex. | R¹ | R³ | R⁴ | Formula | MS m/z: [M + H]⁺ calcd | found |
|---|---|---|---|---|---|---|
| 8 | —OH | —OH | H | $C_{24}H_{23}N_3O_4$ | 418.17 | 418.4 |

8. 1-{(R)-3-Biphenyl-4-yl-2-[(2-hydroxy-pyrimidine-5-carbonyl)-amino]-propyl}-cyclopropanecarboxylic acid

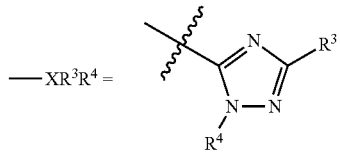

| Ex. | R¹ | R³ | R⁴ | Formula | MS m/z: [M + H]⁺ calcd | found |
|---|---|---|---|---|---|---|
| 3 | —OH | —OH | H | $C_{22}H_{22}N_4O_4$ | 407.16 | 407.4 |
| 4 | —O(CH₂)₃CH₃ | —OH | H | $C_{26}H_{30}N_4O_4$ | 463.23 | 463.4 |

3. 1-{(R)-3-Biphenyl-4-yl-2-[(5-hydroxy-2H-[1,2,4]triazole-3-carbonyl)-amino]-propyl}-cyclopropanecarboxylic acid
4. 1-{(R)-3-Biphenyl-4-yl-2-[(5-hydroxy-2H-[1,2,4]triazole-3-carbonyl)-amino]-propyl}-cyclopropanecarboxylic acid butyl ester

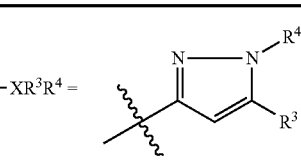

| Ex. | R¹ | R³ | R⁴ | Formula | MS m/z: [M + H]⁺ calcd | found |
|---|---|---|---|---|---|---|
| 9 | —OCH₂CH₃ | —COOCH₂CH₃ | H | $C_{28}H_{31}N_3O_5$ | 490.23 | 490.2 |

9. 5-[(R)-2-Biphenyl-4-yl-1-(1-ethoxycarbonyl-cyclopropylmethyl)-ethylcarbamoyl]-2H-pyrazole-3-carboxylic acid ethyl ester

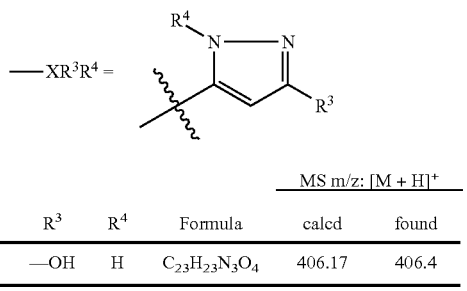

| Ex. | $R^1$ | $R^3$ | $R^4$ | Formula | MS m/z: $[M + H]^+$ calcd | found |
|---|---|---|---|---|---|---|
| 10 | —OH | —OH | H | $C_{23}H_{23}N_3O_4$ | 406.17 | 406.4 |

10. 1-{(R)-3-Biphenyl-4-yl-2-[(5-hydroxy-2H-pyrazole-3-carbonyl)-amino]-propyl}-cyclopropanecarboxylic acid

ASSAY 1

In Vitro Assays for the Quantitation of Inhibitor Potencies at Human and Rat NEP, and Human ACE The inhibitory activities of compounds at human and rat neprilysin (EC 3.4.24.11; NEP) and human angiotensin converting enzyme (ACE) were determined using in vitro assays as described below.

Extraction of NEP Activity from Rat Kidneys

Rat NEP was prepared from the kidneys of adult Sprague Dawley rats. Whole kidneys were washed in cold phosphate buffered saline (PBS) and brought up in ice-cold lysis buffer (1% Triton X-114, 150 mM NaCl, 50 mM tris(hydroxymethyl)aminomethane (Tris) pH 7.5; Bordier (1981) *J. Biol. Chem.* 256:1604-1607) in a ratio of 5 mL of buffer for every gram of kidney. Samples were homogenized on ice using a polytron hand held tissue grinder. Homogenates were centrifuged at 1000×g in a swinging bucket rotor for 5 minutes at 3° C. The pellet was resuspended in 20 mL of ice cold lysis buffer and incubated on ice for 30 minutes. Samples (15-20 mL) were then layered onto 25 mL of ice-cold cushion buffer (6% w/v sucrose, 50 mM pH 7.5 Tris, 150 mM NaCl, 0.06%, Triton X-114), heated to 37° C. for 3-5 minutes and centrifuged at 1000×g in a swinging bucket rotor at room temperature for 3 minutes. The two upper layers were aspirated off, leaving a viscous oily precipitate containing the enriched membrane fraction. Glycerol was added to a concentration of 50% and samples were stored at −20° C. Protein concentrations were quantitated using a BCA detection system with bovine serum albumin (BSA) as a standard.

Enzyme Inhibition Assays

Recombinant human NEP and recombinant human ACE were obtained commercially (R&D Systems, Minneapolis, Minn., catalog numbers 1182-ZN and 929-ZN, respectively). The fluorogenic peptide substrate Mca-D-Arg-Arg-Leu-Dap-(Dnp)-OH (Medeiros et al. (1997) *Braz. J. Med. Biol. Res.* 30:1157-62; Anaspec, San Jose, Calif.) and Abz-Phe-Arg-Lys(Dnp)-Pro-OH (Araujo et al. (2000) *Biochemistry* 39:8519-8525; Bachem, Torrance, Calif.) were used in the NEP and ACE assays respectively.

The assays were performed in 384-well white opaque plates at 37° C. using the fluorogenic peptide substrates at a concentration of 10 μM in Assay Buffer (NEP: 50 mM HEPES, pH 7.5, 100 mM NaCl, 0.01% polyethylene glycol sorbitan monolaurate (Tween-20), 10 μM $ZnSO_4$; ACE: 50 mM HEPES, pH 7.5, 100 mM NaCl, 0.01% Tween-20, 1 μM $ZnSO_4$). The respective enzymes were used at concentrations that resulted in quantitative proteolysis of 1 μM of substrate after 20 minutes at 37° C.

Test compounds were assayed over the range of concentrations from 10 μM to 20 pM. Test compounds were added to the enzymes and incubated for 30 minute at 37° C. prior to initiating the reaction by the addition of substrate. Reactions were terminated after 20 minutes of incubation at 37° C. by the addition of glacial acetic acid to a final concentration of 3.6% (v/v).

Plates were read on a fluorometer with excitation and emission wavelengths set to 320 nm and 405 nm, respectively Inhibition constants were obtained by nonlinear regression of the data using the equation (GraphPad Software, Inc., San Diego, Calif.):

$$v=v_0/[1+(I/K')]$$

where v is the reaction rate, $v_0$ is the uninhibited reaction rate, I is the inhibitor concentration and K' is the apparent inhibition constant.

Compounds of the invention were tested in this assay and found to have $pK_i$ values at human NEP as follows. In general, either the prodrug compounds did not inhibit the enzyme in this in vitro assay, or the prodrugs were not tested (n.d.) since activity would not be expected.

| Ex. | $pK_i$ |
|---|---|
| 1A | n.d. |
| 1B | 8.0-8.9 |
| 2-1 | 7.0-7.9 |
| 2-2 | 7.0-7.9 |
| 2-3 | 7.0-7.9 |
| 2-4 | 8.0-8.9 |
| 2-5 | 8.0-8.9 |
| 2-6 | 7.0-7.9 |
| 2-7 | ≧9.0 |
| 2-8 | n.d. |
| 2-9 | ≧9.0 |
| 2-10 | 8.0-8.9 |
| 2-11 | 8.0-8.9 |
| 2-12 | 8.0-8.9 |
| 2-13 | ≧9.0 |
| 3A | n.d. |
| 3B | 8.0-8.9 |
| 4-1 | 7.0-7.9 |
| 4-2 | 6.0-6.9 |
| 4-3 | 6.0-6.9 |
| 4-4 | 7.0-7.9 |
| 4-5 | 7.0-7.9 |
| 4-6 | 8.0-8.9 |
| 4-7 | 7.0-7.9 |
| 4-8 | 7.0-7.9 |
| 5 | 8.0-8.9 |
| 6A | ≧9.0 |
| 6B | n.d. |
| 6C | n.d. |
| 6D | n.d. |
| 7-1 | 8.0-8.9 |
| 7-2 | 8.0-8.9 |
| 7-3 | ≧9.0 |
| 7-4 | n.d. |
| 7-5 | n.d. |
| 7-6 | n.d. |
| 7-7 | n.d. |
| 7-8 | 7.0-7.9 |
| 7-9 | 7.0-7.9 |
| 7-10 | ≧9.0 |
| 7-11 | ≧9.0 |

-continued

| Ex. | $pK_i$ |
|---|---|
| 7-12 | ≥9.0 |
| 7-13 | 7.0-7.9 |
| 7-14 | 8.0-8.9 |
| 7-15 | 7.0-7.9 |
| 7-16 | 8.0-8.9 |
| 7-17 | 8.0-8.9 |
| 7-18 | 8.0-8.9 |
| 7-19 | ≥9.0 |
| 7-20 | 8.0-8.9 |
| 7-21 | 8.0-8.9 |
| 7-22 | 8.0-8.9 |
| 7-23 | 8.0-8.9 |
| 7-24 | 8.0-8.9 |
| 7-25 | 8.0-8.9 |
| 7-26 | ≥9.0 |
| 8A | ≥9.0 |
| 8B | n.d. |
| 8C | n.d. |
| 9-1 | 8.0-8.9 |
| 9-2 | n.d. |
| 9-3 | 8.0-8.9 |
| 9-4 | 7.0-7.9 |
| 9-5 | 8.0-8.9 |
| 9-6 | ≥9.0 |
| 9-7 | n.d. |
| 9-8 | 7.0-7.9 |
| 9-9 | 7.0-7.9 |
| 9-10 | 7.0-7.9 |
| 9-11 | 8.0-8.9 |
| 9-12 | 7.0-7.9 |
| 9-13 | 7.0-7.9 |
| 9-14 | 7.0-7.9 |
| 9-15 | 8.0-8.9 |
| 9-16 | n.d. |
| 9-17 | 7.0-7.9 |
| 9-18 | 7.0-7.9 |
| 10A | ≥9.0 |
| 10B | n.d. |
| 11-1 | 7.0-7.9 |
| 11-2 | n.d. |
| 11-3 | 8.0-8.9 |
| 11-4 | n.d. |
| 11-5 | ≥9.0 |
| 11-6 | n.d. |
| 11-7 | n.d. |
| 11-8 | 8.0-8.9 |
| 11-9 | n.d. |
| 11-10 | 7.0-7.9 | n.d. = not determined

ASSAY 2

Pharmacodynamic (PD) assay for ACE and NEP Activity in Anesthetized Rats

Male, Sprague Dawley, normotensive rats are anesthetized with 120 mg/kg (i.p.) of inactin. Once anesthetized, the jugular vein, carotid artery (PE 50 tubing) and bladder (flared PE 50 tubing) catheters are cannulated and a tracheotomy is performed (Teflon Needle, size 14 gauge) to faciliate spontaneous respiration. The animals are then allowed a 60 minute stabilization period and kept continuously infused with 5 mL/kg/h of saline (0.9%) throughout, to keep them hydrated and ensure urine production. Body temperature is maintained throughout the experiment by use of a heating pad. At the end of the 60 minute stabilization period, the animals are dosed intravenously (i.v.) with two doses of AngI (1.0 µg/kg, for ACE inhibitor activity) at 15 minutes apart. At 15 minutes post-second dose of AngI, the animals are treated with vehicle or test compound. Five minutes later, the animals are additionally treated with a bolus i.v. injection of atrial natriuretic peptide (ANP; 30 µg/kg). Urine collection (into pre-weighted eppendorf tubes) is started immediately after the ANP treatment and continued for 60 minutes. At 30 and 60 minutes into urine collection, the animals are re-challenged with AngI. Blood pressure measurements are done using the Notocord system (Kalamazoo, Mich.). Urine samples are frozen at −20° C. until used for the cGMP assay. Urine cGMP concentrations are determined by Enzyme Immuno Assay using a commercial kit (Assay Designs, Ann Arbor, Mich., Cat. No. 901-013). Urine volume is determined gravimetrically. Urinary cGMP output is calculated as the product of urine output and urine cGMP concentration. ACE inhibition is assessed by quantifying the % inhibition of pressor response to AngI. NEP inhibition is assessed by quantifying the potentiation of ANP-induced elevation in urinary cGMP output.

ASSAY 3

In Vivo Evaluation of Antihypertensive Effects in the Conscious SHR Model of Hypertension Spontaneously hypertensive rats (SHR, 14-20 weeks of age) are allowed a minimum of 48 hours acclimation upon arrival at the testing site with free access to food and water. For blood pressure recording, these animals are surgically implanted with small rodent radiotransmitters (telemetry unit; DSI Models TA11PA-C40 or C50-PXT, Data Science Inc., USA). The tip of the catheter connected to the transmitter is inserted into the descending aorta above the iliac bifurcation and secured in place with tissue adhesive. The transmitter is kept intraperitoneally and secured to the abdominal wall while closing of the abdominal incision with a non-absorbable suture. The outer skin is closed with suture and staples. The animals are allowed to recover with appropriate post operative care. On the day of the experiment, the animals in their cages are placed on top of the telemetry receiver units to acclimate to the testing environment and baseline recording. After at least of 2 hours baseline measurement is taken, the animals are then dosed with vehicle or test compound and followed out to 24 hours post-dose blood pressure measurement. Data is recorded continuously for the duration of the study using Notocord software (Kalamazoo, Mich.) and stored as electronic digital signals. Parameters measured are blood pressure (systolic, diastolic and mean arterial pressure) and heart rate.

ASSAY 4

In Vivo Evaluation of Antihypertensive Effects in the Conscious DOCA-Salt Rat Model of Hypertension CD rats (male, adult, 200-300 grams, Charles River Laboratory, USA) are allowed a minimum of 48 hours acclimation upon arrival at the testing site before they are placed on a high salt diet. One week after the start of the high salt diet (8% in food or 1% NaCl in drinking water), a deoxycorticosterone acetate (DOCA) pellet (100 mg, 90 days release time, Innovative Research of America, Sarasota, Fla.) is implanted subcutaneously and unilateral nephrectomy is performed. At this time, the animals are also surgically implanted with small rodent radiotransmitters for blood pressure measurement (see Assay 3 for details). The animals are allowed to recover with appropriate post operative care. Study design, data recording, and parameters measured is similar to that described for Assay 3.

ASSAY 5

In Vivo Evaluation of Antihypertensive Effects in the Conscious Dahl/SS Rat Model of Hypertension Male, Dahl salt sensitive rats (Dahl/SS, 6-7 weeks of age from Charles River Laboratory, USA) are allowed at least 48 hours of acclimation upon arrival at the testing site before they were placed on a 8% NaCl high salt diet (TD.92012, Harlan, USA) then surgically implanted with small rodent radiotransmitters for blood pressure measurement (see Assay 3 for details). The animals are allowed to recover with appropriate post operative care. At approximately 4 to 5 weeks from the start of high salt diet, these animals are expected to become hypertensive. Once the hypertension level is confirmed, these animals are used for the study while continued with the high salt diet to maintain their hypertension level. Study design, data recording, and parameters measured is similar to that described in Assay 3.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:
1. A compound of formula I:

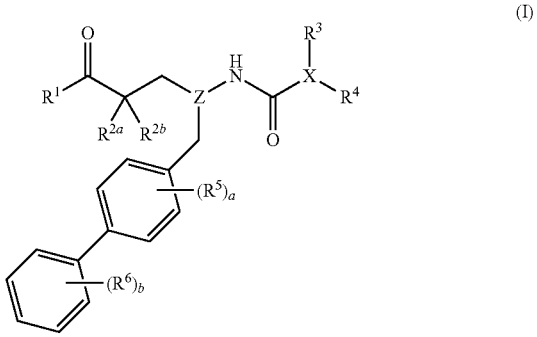

(I)

where:
$R^1$ is selected from —$OR^7$ and —$NR^8R^9$;
$R^{2a}$ is selected from —OH, —OP(O)(OH)$_2$, and —OC(O)CH($R^{37}$)NH$_2$, and $R^{2b}$ is —CH$_3$; or $R^{2a}$ and $R^{2b}$ are taken together to form —CH$_2$—CH$_2$—; or $R^{2a}$ is taken together with $R^7$ to form —OCR$^{18}R^{19}$— or is taken together with $R^8$ to form —OC(O)—;
Z is selected from —CH— and —N—;
X is a —$C_{1-9}$heteroaryl;
$R^3$ is absent or is selected from H; halo; —$C_{0-5}$alkylene-OH; —NH$_2$; —$C_{1-6}$alkyl; —CF$_3$; —$C_{3-7}$cycloalkyl; —$C_{0-2}$alkylene-O—$C_{1-6}$alkyl; —C(O)R$^{20}$; —$C_{0-1}$alkylene-COOR$^{21}$; —C(O)NR$^{22}R^{23}$; —NHC(O)R$^{24}$; =O; —NO$_2$; —C(CH$_3$)=N(OH); phenyl optionally substituted with one or two groups independently selected from halo, —OH, —CF$_3$, —OCH$_3$, —NHC(O)CH$_3$, and phenyl; naphthalenyl; pyridinyl; pyrazinyl; pyrazolyl optionally substituted with methyl; thiophenyl optionally substituted with methyl or halo; furanyl; and —CH$_2$-morpholinyl; and $R^3$, when present, is attached to a carbon atom;
$R^4$ is absent or is selected from H; —OH; —$C_{1-6}$alkyl; —$C_{1-2}$alkylene-COOR$^{35}$; —CH$_2$OC(O)CH(R$^{36}$)NH$_2$; —OCH$_2$OC(O)CH(R$^{36}$)NH$_2$; —OCH$_2$OC(O)CH$_3$; —CH$_2$OP(O)(OH)$_2$; —CH$_2$CH(OH)CH$_2$OH; —CH[CH(CH$_3$)$_2$]—NHC(O)O—$C_{1-6}$alkyl; pyridinyl; and phenyl or benzyl optionally substituted with one or more groups selected from halo, —COOR$^{35}$, —OCH$_3$, —OCF$_3$, and —SCF$_3$; and $R^4$, when present, is attached to a carbon or nitrogen atom;
or $R^3$ and $R^4$ are taken together to form -phenylene-O—(CH$_2$)$_{1-3}$— or -phenylene-O—CH$_2$—CHOH—CH$_2$—;
a is 0 or 1; $R^5$ is selected from halo, —CH$_3$, —CF$_3$, and —CN;
b is 0 or an integer from 1 to 3; each $R^6$ is independently selected from halo, —OH, —CH$_3$, —OCH$_3$, and —CF$_3$;
$R^7$ is selected from H; —$C_{1-8}$alkyl; —$C_{1-3}$alkylene-$C_{6-10}$aryl; —$C_{1-3}$alkylene-$C_{1-9}$heteroaryl; —$C_{3-7}$cycloalkyl; —[(CH$_2$)$_2$O]$_{1-3}$CH$_3$; —$C_{1-6}$alkylene-OC(O)R$^{10}$; —$C_{1-6}$alkylene-NR$^{12}R^{13}$; —$C_{1-6}$alkylene-C(O)R$^{31}$; —$C_{0-6}$alkylenemorpholinyl; —$C_{1-6}$alkylene-SO$_2$—$C_{1-6}$alkyl;

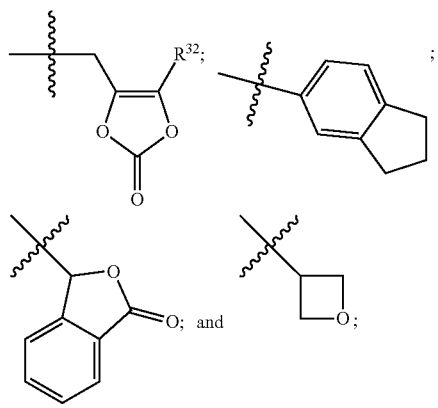

$R^{10}$ is selected from —$C_{1-6}$alkyl, —O—$C_{1-6}$alkyl, —$C_{3-7}$cycloalkyl, —O—$C_{3-7}$cycloalkyl, phenyl, —O-phenyl, —NR$^{12}R^{13}$, —CH[CH(CH$_3$)$_2$]—NH$_2$, —CH[CH(CH$_3$)$_2$]—NHC(O)O—$C_{1-6}$alkyl, and —CH(NH$_2$)CH$_2$COOCH$_3$; and $R^{12}$ and $R^{13}$ are independently selected from H, —$C_{1-6}$alkyl, and benzyl, or $R^{12}$ and $R^{13}$ are taken together as —(CH$_2$)$_{3-6}$—, —C(O)—(CH$_2$)$_3$—, or —(CH$_2$)$_2$O(CH$_2$)$_2$—; $R^{31}$ is selected from —O—$C_{1-6}$alkyl, —O-benzyl, and —NR$^{12}R^{13}$; and $R^{32}$ is —$C_{1-6}$alkyl or —$C_{0-6}$alkylene-$C_{6-10}$aryl;

$R^8$ is selected from H, —OH, —OC(O)R$^{14}$, —CH$_2$COOH, —O-benzyl, pyridyl, and —OC(S)NR$^{15}R^{16}$; $R^{14}$ is selected from H, —$C_{1-6}$alkyl, —$C_{6-10}$aryl, —OCH$_2$—$C_{6-10}$aryl, —CH$_2$O—$C_{6-10}$aryl, and —NR$^{15}R^{16}$; and $R^{15}$ and $R^{16}$ are independently selected from H and —$C_{1-4}$alkyl;

$R^9$ is selected from H, —$C_{1-6}$alkyl, and —C(O)R$^{17}$; and $R^{17}$ is selected from H, —$C_{1-6}$alkyl, —$C_{3-7}$cycloalkyl, —$C_{6-10}$aryl, and —$C_{1-9}$heteroaryl;

$R^{18}$ and $R^{19}$ are independently selected from H, —$C_{1-6}$alkyl, and —O—$C_{3-7}$cycloalkyl, or $R^{18}$ and $R^{19}$ are taken together to form =O;

$R^{20}$ is selected from H and —$C_{1-6}$alkyl;

$R^{21}$ and $R^{35}$ are independently selected from H, —$C_{1-6}$alkyl, —$C_{1-3}$alkylene-$C_{6-10}$aryl, —$C_{1-3}$alkylene-$C_{1-9}$heteroaryl, —$C_{3-7}$cycloalkyl, —[(CH$_2$)$_2$O]$_{1-3}$CH$_3$, —$C_{1-6}$alkylene-OC(O)R$^{25}$, —$C_{1-6}$alkylene-NR$^{27}R^{28}$, —$C_{1-6}$alkylene-C(O)R$^{33}$, —$C_{0-6}$alkylenemorpholinyl, —$C_{1-6}$alkylene-SO$_2$—$C_{1-6}$alkyl,

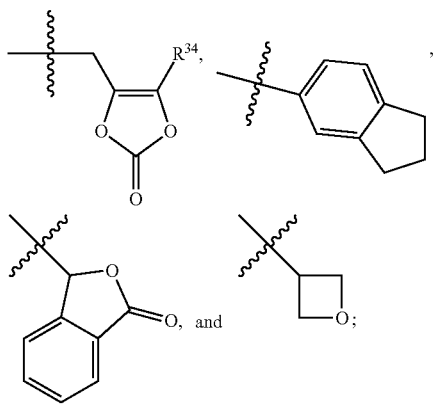

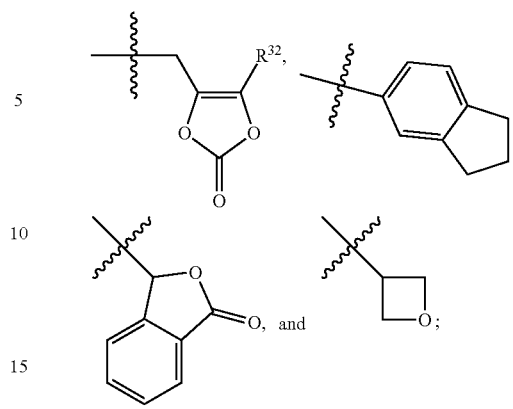

R$^{25}$ is selected from —C$_{1-6}$alkyl, —O—C$_{1-6}$alkyl, —C$_{3-7}$cycloalkyl, —O—C$_{3-7}$cycloalkyl, phenyl, —O-phenyl, —NR$^{27}$R$^{28}$, —CH[CH(CH$_3$)$_2$]—NH$_2$, —CH[CH(CH$_3$)$_2$]—NHC(O)O—C$_{1-6}$alkyl, and —CH(NH$_2$)CH$_2$COOCH$_3$; and R$^{27}$ and R$^{28}$ are independently selected from H, —C$_{1-6}$alkyl, and benzyl, or R$^{27}$ and R$^{28}$ are taken together as —(CH$_2$)$_{3-6}$—, —C(O)—(CH$_2$)$_3$—, or —(CH$_2$)$_2$O(CH$_2$)$_2$—; R$^{33}$ is selected from —O—C$_{1-6}$alkyl, —O-benzyl, and —NR$^{27}$R$^{28}$; and R$^{34}$ is —C$_{1-6}$alkyl or —C$_{0-6}$alkylene-C$_{6-10}$aryl;

R$^{22}$ and R$^{23}$ are independently selected from H, —C$_{1-6}$alkyl, —CH$_2$COOH, —(CH$_2$)$_2$OH, —(CH$_2$)$_2$OCH$_3$, —(CH$_2$)$_2$SO$_2$NH$_2$, —(CH$_2$)$_2$N(CH$_3$)$_2$, —C$_{0-1}$alkylene-C$_{3-7}$cycloalkyl, and —(CH$_2$)$_2$-imidazolyl; or R$^{22}$ and R$^{23}$ are taken together to form a saturated or partially unsaturated —C$_{3-5}$heterocycle optionally substituted with halo, —OH, —COOH, or —CONH$_2$; and optionally containing an oxygen atom in the ring;

R$^{24}$ is selected from —C$_{1-6}$alkyl; —C$_{0-1}$alkylene-O—C$_{1-6}$alkyl; phenyl optionally substituted with halo or —OCH$_3$; and —C$_{1-9}$heteroaryl;

R$^{36}$ is selected from H, —CH(CH$_3$)$_2$, phenyl, and benzyl; and

R$^{37}$ is selected from H, —CH(CH$_3$)$_2$, phenyl, and benzyl;

where each alkyl group in R$^1$, R$^3$, and R$^4$ is optionally substituted with 1 to 8 fluoro atoms; and;

where the methylene linker on the biphenyl is optionally substituted with one or two —C$_{1-6}$alkyl groups or cyclopropyl;

or a pharmaceutically acceptable salt thereof.

2. The compound of claim 1, where X is selected from pyrazole, imidazole, triazole, benzotriazole, furan, pyrrole, tetrazole, pyrazine, thiophene, oxazole, isoxazole, thiazole, isothiazole, oxadiazole, thiadiazole, pyridazine, pyridine, pyrimidine, pyran, benzimidazole, benzoxazole, benzothiazole, pyridylimidazole, and pyridyltriazole.

3. The compound of claim 2, wherein X is selected from pyrazole, triazole, benzotriazole, tetrazole, oxazole, isoxazole, pyrimidine, and pyridyltriazole.

4. The compound of claim 1, where R$^1$ is selected from —OR$^7$ and —NR$^8$R$^9$; R$^7$ is H; R$^8$ is H or —OH; and R$^9$ is H.

5. The compound of claim 1, where:
R$^1$ is —OR$^7$; and R$^7$ is selected from —C$_{1-8}$alkyl, —C$_{1-3}$alkylene-C$_{6-10}$aryl, —C$_{1-3}$alkylene-C$_{1-9}$heteroaryl, —C$_{3-7}$cycloalkyl, —[(CH$_2$)$_2$O]$_{1-3}$CH$_3$, —C$_{1-6}$alkylene-OC(O)R$^{16}$, —C$_{1-6}$alkylene-NR$^{12}$R$^{13}$, —C$_{1-6}$alkylene-C(O)R$^{31}$, —C$_{0-6}$alkylenemorpholinyl, —C$_{1-6}$alkylene-SO$_2$—C$_{1-6}$alkyl, R$^1$ is —NR$^8$R$^9$; R$^8$ is selected from —OC(O)R$^{14}$, —CH$_2$COOH, —O-benzyl, pyridyl, and —OC(S)NR$^{15}$R$^{16}$; and R$^9$ is H; or R$^1$ is —NR$^8$R$^9$; R$^8$ is selected from —OC(O)R$^{14}$, —CH$_2$COOH, —O-benzyl, pyridyl, and —OC(S)NR$^{15}$R$^{16}$; and R$^9$ is —C$_{1-6}$alkyl or —C(O)R$^{17}$;

R$^1$ is —NR$^8$R$^9$; R$^8$ is selected from H or —OH; and R$^9$ is —C$_{1-6}$alkyl or —C(O)R$^{17}$;

R$^1$ is —OR$^7$ and R$^{2a}$ is taken together with R$^7$ to form —OCR$^{18}$R$^{19}$—; or R$^1$ is —NR$^8$R$^9$ and R$^{2a}$ is taken together with R$^8$ to form —OC(O)—.

6. The compound of claim 1, where R$^1$ is —OR$^7$ and R$^7$ is H or —C$_{1-8}$alkyl.

7. The compound of claim 1, where R$^{2a}$ is —OH and R$^{2b}$ is —CH$_3$.

8. The compound of claim 1, where R$^{2a}$ and R$^{2b}$ are taken together to form —CH$_2$—CH$_2$—.

9. The compound of claim 1, where Z is —CH—.

10. The compound of claim 1, where Z is —N—.

11. The compound of claim 1, where R$^3$ is absent or is selected from H; halo; —C$_{0-5}$alkylene-OH; —NH$_2$; —C$_{1-6}$alkyl; —CF$_3$; —C$_{3-7}$cycloalkyl; —C$_{0-2}$alkylene-O—C$_{1-6}$alkyl; —C(O)R$^{20}$; —C$_{0-1}$alkylene-COOR$^{21}$; —C(O)NR$^{22}$R$^{23}$; —NHC(O)R$^{24}$; =O; —NO$_2$; —C(CH$_3$)=N(OH); phenyl optionally substituted with one or two groups independently selected from halo, —OH, —CF$_3$, —OCH$_3$, —NHC(O)CH$_3$, and phenyl; naphthalenyl; pyridinyl; pyrazinyl; pyrazolyl optionally substituted with methyl; thiophenyl optionally substituted with methyl or halo; furanyl; and —CH$_2$-morpholinyl; and R$^{21}$ is H.

12. The compound of claim 1, where R$^3$ is —C$_{0-1}$alkylene-COOR$^{21}$; and R$^{21}$ is selected from —C$_{1-6}$alkyl, —C$_{1-3}$alkylene-C$_{6-10}$aryl, —C$_{1-3}$alkylene-C$_{1-9}$heteroaryl, —C$_{3-7}$cycloalkyl, —[(CH$_2$)$_2$O]$_{1-3}$CH$_3$, —C$_{1-6}$alkylene-OC(O)R$^{25}$, —C$_{1-6}$alkylene-NR$^{27}$R$^{28}$, C$_{1-6}$alkylene-C(O)R$^{33}$, —C$_{0-6}$alkylenemorpholinyl, —C$_{1-6}$alkylene-SO$_2$—C$_{1-6}$alkyl,

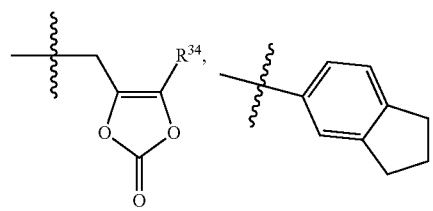

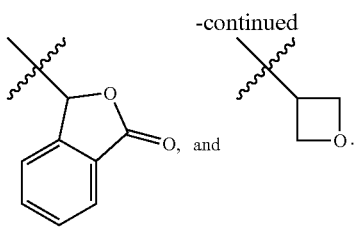

13. The compound of claim 1, where $R^3$ is absent or is selected from H, halo, —$C_{0-5}$alkylene-OH, —$C_{0-1}$alkylene-O—$C_{1-6}$alkyl, —C(O)$R^{20}$, —$C_{0-1}$alkylene-COOR$^{21}$, —C(O)NR$^{22}$R$^{23}$, =O, and pyrazinyl; $R^{20}$ is —$C_{1-6}$alkyl; $R^{21}$ is H or —$C_{1-6}$alkyl; $R^{22}$ and $R^{23}$ are independently selected from H, —$C_{1-6}$alkyl, —(CH$_2$)$_2$OCH$_3$, and —(CH$_2$)$_2$-imidazolyl; or $R^{22}$ and $R^{23}$ are taken together to form a saturated —$C_{3-5}$heterocycle optionally substituted with —OH or —COOH, and optionally containing an oxygen atom in the ring.

14. The compound of claim 1, where $R^4$ is absent or is selected from H; —OH; —$C_{1-6}$alkyl; —$C_{1-2}$alkylene-COOR$^{35}$; —CH$_2$OC(O)CH(R$^{36}$)NH$_2$; —CH$_2$CH(OH)CH$_2$OH; pyridinyl; and phenyl or benzyl optionally substituted with one or more groups selected from halo, —COOR$^{35}$, —OCH$_3$, —OCF$_3$, and —SCF$_3$; and $R^{35}$ is H.

15. The compound of claim 1, where $R^4$ is selected from —OCH$_2$OC(O)CH$_3$; —CH$_2$OP(O)(OH)$_2$; —$C_{1-2}$alkylene-COOR$^{35}$; and phenyl or benzyl substituted with at least one —COOR$^{35}$ group; where $R^{35}$ is selected from —$C_{1-6}$alkyl, —$C_{1-3}$alkylene-$C_{6-10}$aryl, —$C_{1-3}$alkylene-$C_{1-9}$heteroaryl, —$C_{3-7}$cycloalkyl, —[(CH$_2$)$_2$O]$_{1-3}$CH$_3$, —$C_{1-6}$alkylene-OC(O)R$^{25}$, —$C_{1-6}$alkylene-NR$^{27}$R$^{28}$, —$C_{1-6}$alkylene-C(O)R$^{33}$, —$C_{0-6}$alkylenemorpholinyl, —$C_{1-6}$alkylene-SO$_2$—$C_{1-6}$alkyl,

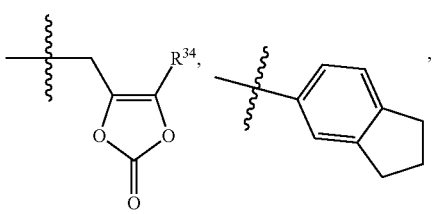

16. The compound of claim 1, where $R^4$ is selected from H and —OH.

17. The compound of claim 1, where a is 0.

18. The compound of claim 1, where b is 0; or b is 1 and $R^6$ is selected from halo, —OH, and —OCH$_3$; or b is 2 and each $R^6$ is independently selected from halo and —CH$_3$.

19. The compound of claim 1, where $R^1$ is —OR$^7$; $R^7$ is H or —$C_{1-8}$alkyl; X is selected from pyrazole, triazole, benzotriazole, tetrazole, oxazole, isoxazole, pyrimidine, and pyridyltriazole; $R^3$ is absent or is selected from H, halo, —$C_{0-5}$ alkylene-OH, —$C_{0-1}$alkylene-O—$C_{1-6}$alkyl, —C(O)R$^{20}$, —$C_{0-1}$alkylene-COOR$^{21}$, —C(O)NR$^{22}$R$^{23}$, =O, and pyrazinyl; $R^{20}$ is —$C_{1-6}$alkyl; $R^{21}$ is H or —$C_{1-6}$alkyl; $R^{22}$ and $R^{23}$ are independently selected from H, —$C_{1-6}$alkyl, —(CH$_2$)$_2$OCH$_3$, and —(CH$_2$)$_2$-imidazolyl; or $R^{22}$ and $R^{23}$ are taken together to form a saturated —$C_{3-5}$heterocycle optionally substituted with —OH or —COOH, and optionally containing an oxygen atom in the ring; $R^4$ is selected from H and —OH; a is 0; and b is 0; or b is 1 and $R^6$ is selected from halo, —OH, and —OCH$_3$; or b is 2 and each $R^6$ is independently selected from halo and —CH$_3$.

20. The compound of claim 1, where $R^1$ is —OR$^7$; $R^{2a}$ is —OH and $R^{2b}$ is —CH$_3$; or $R^{2a}$ and $R^{2b}$ are taken together to form —CH$_2$—CH$_2$—; X is selected from pyrazole, triazole, isoxazole, and pyrimidine; $R^3$ is selected from H, —$C_{0-5}$alkylene-OH, and —$C_{0-1}$alkylene-COOR$^{21}$; $R^{21}$ is H or —$C_{1-6}$alkyl; $R^4$ is selected from H and —OH; a is 0; and b is 0; or b is 1 and $R^6$ is halo; or b is 2 and each $R^6$ is independently selected from halo and —CH$_3$.

21. A process for preparing the compound of claim 1, comprising the step of coupling a compound of formula 1 with a compound of formula 2:

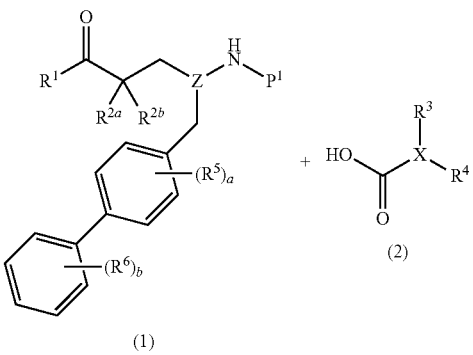

to produce a compound of formula I; where $P^1$ is H or an amino-protecting group selected from t-butoxycarbonyl, trityl, benzyloxycarbonyl, 9-fluorenylmethoxycarbonyl, formyl, trimethylsilyl, and t-butyldimethylsilyl; and where the process further comprises deprotecting the compound of formula 1 when $P^1$ is an amino protecting group.

22. A process for preparing the compound of claim 1, comprising the step of deprotecting a compound selected from:

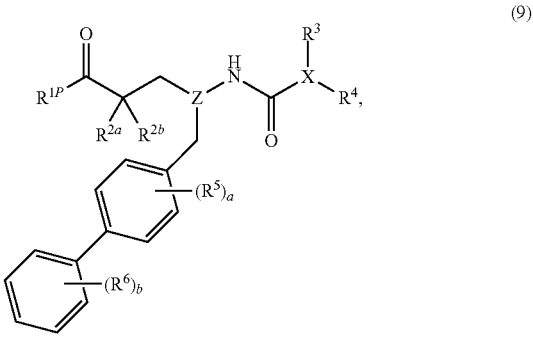

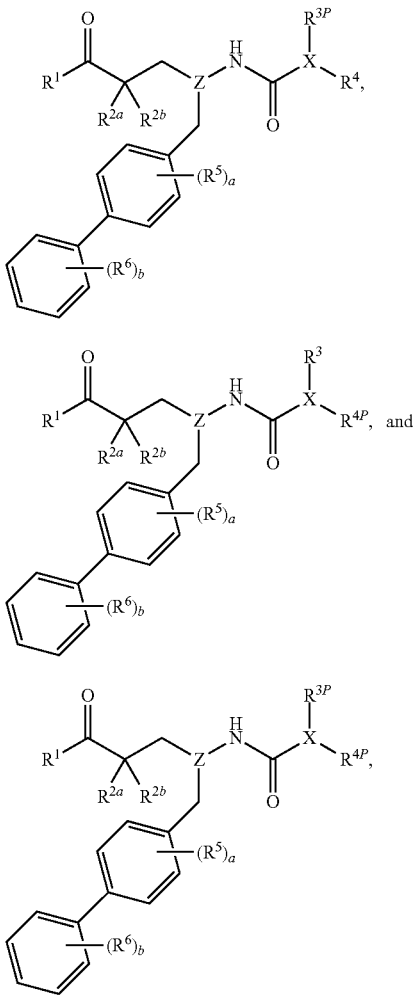

or a salt thereof; where $R^{1P}$ is selected from —O—$P^3$, —NH$P^2$, and —NH(O—$P^4$); $R^{3P}$ is selected from —$C_{0-5}$alkylene-O—$P^4$, —$C_{0-1}$alkylene-COO—$P^3$, and phenyl substituted with —O—$P^4$; $R^{4P}$ is selected from —O—$P^4$; —$C_{1-2}$alkylene-COO—$P^3$; and phenyl or benzyl substituted with —COO—$P^3$; $P^2$ is an amino-protecting group selected from t-butoxycarbonyl, trityl, benzyloxycarbonyl, 9-fluorenyl- methoxycarbonyl, formyl, trimethylsilyl, and t-butyldimethylsilyl; $P^3$ is a carboxy-protecting group selected from methyl, ethyl, t-butyl, benzyl, p-methoxybenzyl, 9-fluorenylmethyl, trimethylsilyl, t-butyldimethylsilyl, and diphenylmethyl; and $P^4$ is a hydroxyl-protecting group selected from —$C_{1-6}$alkyl, tri$C_{1-6}$alkylsilyl, —$C_{1-6}$alkanoyl, benzoyl, benzyl, p-methoxybenzyl, 9-fluorenylmethyl, and diphenylmethyl.

23. A pharmaceutical composition comprising the compound of claim 1 and a pharmaceutically acceptable carrier.

24. The pharmaceutical composition of claim 23, further comprising a therapeutic agent selected from adenosine receptor antagonists, α-adrenergic receptor antagonists, $β_1$-adrenergic receptor antagonists, $β_2$-adrenergic receptor agonists, dual-acting β-adrenergic receptor antagonists/$α_1$-receptor antagonists, advanced glycation end product breakers, aldosterone antagonists, aldosterone synthase inhibitors, aminopeptidase N inhibitors, androgens, angiotensin-converting enzyme inhibitors and dual-acting angiotensin-converting enzyme/neprilysin inhibitors, angiotensin-converting enzyme 2 activators and stimulators, angiotensin-II vaccines, anticoagulants, anti-diabetic agents, antidiarrheal agents, anti-glaucoma agents, anti-lipid agents, antinociceptive agents, anti-thrombotic agents, $AT_1$ receptor antagonists and dual-acting $AT_1$ receptor antagonist/neprilysin inhibitors and multifunctional angiotensin receptor blockers, bradykinin receptor antagonists, calcium channel blockers, chymase inhibitors, digoxin, diuretics, dopamine agonists, endothelin converting enzyme inhibitors, endothelin receptor antagonists, HMG-CoA reductase inhibitors, estrogens, estrogen receptor agonists and/or antagonists, monoamine reuptake inhibitors, muscle relaxants, natriuretic peptides and their analogs, natriuretic peptide clearance receptor antagonists, neprilysin inhibitors, nitric oxide donors, non-steroidal anti-inflammatory agents, N-methyl d-aspartate receptor antagonists, opioid receptor agonists, phosphodiesterase inhibitors, prostaglandin analogs, prostaglandin receptor agonists, renin inhibitors, selective serotonin reuptake inhibitors, sodium channel blocker, soluble guanylate cyclase stimulators and activators, tricyclic antidepressants, vasopressin receptor antagonists, and combinations thereof.

25. The pharmaceutical composition of claim 24, wherein the therapeutic agent is an $AT_1$ receptor antagonist.

26. A method for treating hypertension, comprising administering to a patient a therapeutically effective amount of the compound of claim 1.

* * * * *

UNITED STATES PATENT AND TRADEMARK OFFICE
CERTIFICATE OF CORRECTION

PATENT NO. : 8,449,890 B2
APPLICATION NO. : 13/398027
DATED : May 28, 2013
INVENTOR(S) : Melissa Fleury et al.

It is certified that error appears in the above-identified patent and that said Letters Patent is hereby corrected as shown below:

In the Claims:

At Column 123, lines 64-65,

"-$C_{1-6}$alkylene-OC(O)$R^{16}$" should be "-$C_{1-6}$alkylene-OC(O)$R^{10}$".

Signed and Sealed this
First Day of October, 2013

Teresa Stanek Rea
*Deputy Director of the United States Patent and Trademark Office*